US006748900B2

(12) United States Patent
Harris, Jr. et al.

(10) Patent No.: US 6,748,900 B2
(45) Date of Patent: Jun. 15, 2004

(54) METHODS FOR GROWING AND IMPRINTING FISH USING AN ODORANT

(75) Inventors: H. William Harris, Jr., Portland, ME (US); Steven Jury, Milton, NY (US); David R. Russell, Alfred, ME (US); Jacqueline Nearing, N. Yarmouth, ME (US); Marlies Betka, Portland, ME (US); Timothy Linley, East Parsonsfield, ME (US); Edward M. Brown, Milton, MA (US)

(73) Assignee: MariCal, Inc., Portland, ME (US)

( * ) Notice: Subject to any disclaimer, the term of this patent is extended or adjusted under 35 U.S.C. 154(b) by 0 days.

(21) Appl. No.: 10/268,051

(22) Filed: Oct. 8, 2002

(65) Prior Publication Data

US 2003/0124090 A1 Jul. 3, 2003

Related U.S. Application Data

(60) Provisional application No. 60/328,464, filed on Oct. 11, 2001.

(51) Int. Cl.[7] .................... A01K 61/00

(52) U.S. Cl. .................... 119/231

(58) Field of Search .................... 119/231, 215, 119/204, 212, 230, 242, 234; 435/375; 426/2

(56) References Cited

U.S. PATENT DOCUMENTS

| | | | | |
|---|---|---|---|---|
| 3,406,662 A | * 10/1968 | Vik et al. | 119/217 |
| 3,777,709 A | * 12/1973 | Anderson et al. | 119/217 |
| 5,651,651 A | * 7/1997 | Spencer | 411/372.6 |
| 5,823,142 A | * 10/1998 | Cardinale et al. | 119/212 |
| 5,827,551 A | * 10/1998 | Prochnow et al. | 426/1 |
| 6,016,770 A | * 1/2000 | Fisher | 119/215 |
| 6,269,586 B1 | * 8/2001 | Jones | 43/42.06 |
| 6,410,249 B1 | * 6/2002 | Ngai et al. | 435/7.21 |
| 6,463,882 B1 | * 10/2002 | Harris et al. | 119/230 |
| 6,463,883 B1 | * 10/2002 | Harris et al. | 119/230 |
| 6,475,792 B1 | * 11/2002 | Harris et al. | 435/375 |
| 6,481,379 B1 | * 11/2002 | Harris et al. | 119/230 |
| 6,564,747 B2 | * 5/2003 | Harris et al. | 119/230 |

FOREIGN PATENT DOCUMENTS

| | | |
|---|---|---|
| JP | 57-64601 | * 4/1982 |
| JP | 61145196 | * 7/1986 |

* cited by examiner

*Primary Examiner*—Yvonne R. Abbott
(74) *Attorney, Agent, or Firm*—Hamilton, Brook, Smith & Reynolds, P.C.

(57) ABSTRACT

The present invention relates to methods of imprinting fish in freshwater with at least one odorant for the fish and causing the imprinted fish to react to the odorant in seawater, wherein the fish are maintained in freshwater prior to transfer to seawater. The method includes: adding at least one Polyvalent Cation Sensing Receptor (PVCR) modulator to the freshwater in an amount sufficient to modulate expression and/or sensitivity of at least one PVCR, the PVCR modulator being one which alters olfactory sensing of the fish to the odorant; adding feed for fish consumption to the freshwater, the feed containing the odorant and an amount of NaCl sufficient to contribute to a significantly increased level of the PVCR modulator in serum of the fish upon consumption of the feed, whereby the fish are imprinted with the odorant; transferring the imprinted fish to seawater; and providing a source of said odorant in the seawater to which the imprinted fish are transferred, thereby causing the imprinted fish to react to said odorant. The present invention also includes methods of homing or attracting fish, as well as methods for repelling fish by modulating the expression and/or sensitivity of the PVCR in the olfactory apparatus of the fish.

36 Claims, 22 Drawing Sheets

```
cttggcatta tgctctgtgc tgggggtatt cttgacagca ttcgtgatgg gagtgtttat 60
caaatttcgc aacaccccaa ttgttaaggc cacaaacaga gagctatcct acctcctcct 120
gttctcactc atctgctgtt tctccagttc cctcatcttc attggtgaac cccaggactg 180
gacatgccgt ctacgccagc ctgcattcgg gataagtttt gttctctgca tctcctgcat 240
cctggtaaaa actaaccgag tacttctagt gttcgaagcc aagatcccca ccagtctcca 300
tcgtaagtgg tgggggctaa acttgcagtt cctgttagtg ttcctgttca catttgtgca 360
agtgatgata tgtgtggtct ggctttacaa tgctcctccg gcgagctaca ggaaccatga 420
cattgatgag ataattttca ttacatgcaa tgagggctct atgatggcgc ttggcttcct 480
aattgggtac acatgcctgc tggcagccat atrcttcttc tttgcattta aatcacgaaa 540
actgccagag aactttactg aggctaagtt catcaccttc agcatgctca tctt       594
                                                        (SEQ ID NO: 1)

Leu Ala Leu Cys Ser Val Leu Gly Val Phe Leu Thr Ala Phe Val Met
 1               5                  10                  15
Gly Val Phe Ile Lys Phe Arg Asn Thr Pro Ile Val Lys Ala Thr Asn
            20                  25                  30
Arg Glu Leu Ser Tyr Leu Leu Leu Phe Ser Leu Ile Cys Cys Phe Ser
        35                  40                  45
Ser Ser Leu Ile Phe Ile Gly Glu Pro Gln Asp Trp Thr Cys Arg Leu
    50                  55                  60
Arg Gln Pro Ala Phe Gly Ile Ser Phe Val Leu Cys Ile Ser Cys Ile
65                  70                  75                  80
Leu Val Lys Thr Asn Arg Val Leu Leu Val Phe Glu Ala Lys Ile Pro
                85                  90                  95
Thr Ser Leu His Arg Lys Trp Trp Gly Leu Asn Leu Gln Phe Leu Leu
            100                 105                 110
Val Phe Leu Phe Thr Phe Val Gln Val Met Ile Cys Val Val Trp Leu
        115                 120                 125
Tyr Asn Ala Pro Pro Ala Ser Tyr Arg Asn His Asp Ile Asp Glu
    130                 135                 140
Ile Ile Phe Ile Thr Cys Asn Glu Gly Ser Met Met Ala Leu Gly Phe
    145                 150                 155
Leu Ile Gly Tyr Thr Cys Leu Leu Ala Ala Ile Xaa Phe Phe Phe Ala
160                 165                 170                 175
Phe Lys Ser Arg Lys Leu Pro Glu Asn Phe Thr Glu Ala Lys Phe Ile
                180                 185                 190
Thr Phe Ser Met Leu Ile
            195         (SEQ ID NO: 2)

Xaa=any amino acid
```

```
cttggcatta tgctctgtgc tgggggtatt cttgacagca ttcgtgatgg gagtgtttat 60
caaatttcgc aacaccccaa ttgttaaggc cacaaacaga gagctatcct acctcctcct 120
gttctcactc atctgctgtt tctccagttc cctcatcttc attggtgaac cccaggactg 180
gacatgccgt ctacgccagc ctgcattcgg gataagtttt gttctctgca tctcctgcat 240
cctggtaaaa actaaccgag tacttctagt gttcgaagcc aagatcccca ccagtctcca 300
tcgtaagtgg tgggggctaa acttgcagtt cctgttagtg ttcctgttca catttgtgca 360
agtgatgata tgtgtggtct ggctttacaa tgctcctccg gcgagctaca ggaaccatga 420
cattgatgag ataattttca ttacatgcaa tgagggctct atgatggcgc ttggcttcct 480
aattgggtac acatgcctgc tggcagccat atrcttcttc tttgcattta aatcacgaaa 540
actgccagag aactttactg aggctaagtt catcaccttc agcatgctca tctt       594
                                                   (SEQ ID NO: 1)
```

```
Leu Ala Leu Cys Ser Val Leu Gly Val Phe Leu Thr Ala Phe Val Met
 1               5                  10                  15
Gly Val Phe Ile Lys Phe Arg Asn Thr Pro Ile Val Lys Ala Thr Asn
            20                  25                  30
Arg Glu Leu Ser Tyr Leu Leu Leu Phe Ser Leu Ile Cys Cys Phe Ser
        35                  40                  45
Ser Ser Leu Ile Phe Ile Gly Glu Pro Gln Asp Trp Thr Cys Arg Leu
    50                  55                  60
Arg Gln Pro Ala Phe Gly Ile Ser Phe Val Leu Cys Ile Ser Cys Ile
65                  70                  75                  80
Leu Val Lys Thr Asn Arg Val Leu Leu Val Phe Glu Ala Lys Ile Pro
                85                  90                  95
Thr Ser Leu His Arg Lys Trp Trp Gly Leu Asn Leu Gln Phe Leu Leu
            100                 105                 110
Val Phe Leu Phe Thr Phe Val Gln Val Met Ile Cys Val Val Trp Leu
        115                 120                 125
Tyr Asn Ala Pro Pro Ala Ser Tyr Arg Asn His Asp Ile Asp Glu
    130                 135                 140
Ile Ile Phe Ile Thr Cys Asn Glu Gly Ser Met Met Ala Leu Gly Phe
    145                 150                 155
Leu Ile Gly Tyr Thr Cys Leu Leu Ala Ala Ile Xaa Phe Phe Phe Ala
160                 165                 170                 175
Phe Lys Ser Arg Lys Leu Pro Glu Asn Phe Thr Glu Ala Lys Phe Ile
                180                 185                 190
Thr Phe Ser Met Leu Ile
            195         (SEQ ID NO: 2)
```

Xaa=any amino acid

FIG. 1

```
cttggcatta tgctctgtgc tgggggtatt cttgacagca ttcgtgatgg gagtgtttat 60
cagatttcgc aacaccccaa ttgttaaggc cacaaacaga gagctatcct acctcctcct 120
gttctcactc atctgctgtt tctccagctc cctcatcttc attggtgaac cccaggactg 180
gacatgccgt ctacgccagc ctgcattcgg gataagtttt gttctctgca tctcctgcat 240
cctggtcaaa actaaccgag tacttctagt gttcgaagcc aagatcccca ccagtctcca 300
tcgtaagtgg tgggggctaa acttgcagtt cctgttggtg ttcctgttca catttgtgca 360
agtgatgata tgtgtggtct ggctttacaa tgctcctccg gcgagctaca ggaaccatga 420
cattgatgag ataattttca ttacatgcaa tgagggctct atgatggcgc tcggcttcct 480
aattgggtac acatgcctgc tggcagccat atgcttcttc tttgcattta aatcacgaaa 540
actgccagag aactttaccg aggctaagtt catcaccttc agcatgctca tctt      594
                                                      (SEQ ID NO: 3)
```

```
Leu Ala Leu Cys Ser Val Leu Gly Val Phe Leu Thr Ala Phe Val Met
 1               5                  10                  15
Gly Val Phe Ile Arg Phe Arg Asn Thr Pro Ile Val Lys Ala Thr Asn
            20                  25                  30
Arg Glu Leu Ser Tyr Leu Leu Leu Phe Ser Leu Ile Cys Cys Phe Ser
        35                  40                  45
Ser Ser Leu Ile Phe Ile Gly Glu Pro Gln Asp Trp Thr Cys Arg Leu
    50                  55                  60
Arg Gln Pro Ala Phe Gly Ile Ser Phe Val Leu Cys Ile Ser Cys Ile
65                  70                  75                  80
Leu Val Lys Thr Asn Arg Val Leu Leu Val Phe Glu Ala Lys Ile Pro
                85                  90                  95
Thr Ser Leu His Arg Lys Trp Trp Gly Leu Asn Leu Gln Phe Leu Leu
            100                 105                 110
Val Phe Leu Phe Thr Phe Val Gln Val Met Ile Cys Val Val Trp Leu
        115                 120                 125
Tyr Asn Ala Pro Pro Ala Ser Tyr Arg Asn His Asp Ile Asp Glu
    130                 135                 140
Ile Ile Phe Ile Thr Cys Asn Glu Gly Ser Met Met Ala Leu Gly Phe
    145                 150                 155
Leu Ile Gly Tyr Thr Cys Leu Leu Ala Ala Ile Cys Phe Phe Phe Ala
160                 165                 170                 175
Phe Lys Ser Arg Lys Leu Pro Glu Asn Phe Thr Glu Ala Lys Phe Ile
                180                 185                 190
Thr Phe Ser Met Leu Ile
            195         (SEQ ID NO: 4)
```

Xaa = Any amino acid

FIG. 2

```
ttggcattat gctctgtgct gggggtattc ttgacagtat tcgtgatggg agtgtttatc 60
agatttcgca acaccccaat tgttaaggcc acaaacagag agctatccta cctcctcctg 120
ttctcactta tctgctgttt ctccagctcc ctcatcttca ttggtgaacc ccaggactgg 180
acatgccgtc tacgccagcc tgcattcggg ataagttttg ttctctgcat ctcctgcatc 240
ctggtcaaaa ctaaccgagt acttctagtg ttcgaagcaa agatccccac cagtctccat 300
cgtaagtggt gggggctaaa cttgcagttc ctgttggtgt tcctgttcac atttgtgcaa 360
gtgatgatat gtgtggtctg gctttacaat gctcctccgg cgagctacag gaaccatgac 420
attgatgaga tcattttcat tacatgcaat gagggctcta tgatggcgct tggcttccta 480
attgggtaca catgcctgct ggcagccata tgcttcttct ttgcatttaa atcacgaaaa 540
ctgccagaga attttaccga ggctaagttc atcaccttca gcatgctcat ctt        593
                                                   (SEQ ID NO: 5)
```

```
Leu Ala Leu Cys Ser Val Leu Gly Val Phe Leu Thr Val Phe Val Met
 1               5                  10                  15
Gly Val Phe Ile Arg Phe Arg Asn Thr Pro Ile Val Lys Ala Thr Asn
            20                  25                  30
Arg Glu Leu Ser Tyr Leu Leu Leu Phe Ser Leu Ile Cys Cys Phe Ser
        35                  40                  45
Ser Ser Leu Ile Phe Ile Gly Glu Pro Gln Asp Trp Thr Cys Arg Leu
    50                  55                  60
Arg Gln Pro Ala Phe Gly Ile Ser Phe Val Leu Cys Ile Ser Cys Ile
65                  70                  75                  80
Leu Val Lys Thr Asn Arg Val Leu Leu Val Phe Glu Ala Lys Ile Pro
                85                  90                  95
Thr Ser Leu His Arg Lys Trp Trp Gly Leu Asn Leu Gln Phe Leu Leu
            100                 105                 110
Val Phe Leu Phe Thr Phe Val Gln Val Met Ile Cys Val Val Trp Leu
        115                 120                 125
Tyr Asn Ala Pro Pro Ala Ser Tyr Arg Asn His Asp Ile Asp Glu
    130                 135                 140
Ile Ile Phe Ile Thr Cys Asn Glu Gly Ser Met Met Ala Leu Gly Phe
    145                 150                 155
Leu Ile Gly Tyr Thr Cys Leu Leu Ala Ala Ile Cys Phe Phe Phe Ala
160                 165                 170                 175
Phe Lys Ser Arg Lys Leu Pro Glu Asn Phe Thr Glu Ala Lys Phe Ile
                180                 185                 190
Thr Phe Ser Met Leu Ile
            195          (SEQ ID NO: 6)
```

Xaa = Any amino acid

FIG. 3

```
aattccgttg ctgtcggttc agtccaagtc tcctccagtg caaaatgaga aatggtggtc 60
gccattacag gaacatgcac tacatctgtg ttaatgaaat attgtcagtt atctgaaggt 120
tattaaaatg tttctgcaag gatggcttca cgagaaatca attctgcacg ttttcccatt 180
gtcattgtat gaataactga ccaaagggat gtaacaaaat ggaacaaagc tgaggaccac 240
gttcaccctt tcttggagca tacgatcaac cctgaaggag atggaagact tgaggaggaa 300
atggggattg atcttccagg agttctgctg taaagcgatc cctcaccatt acaaagataa 360
gcagaaatcc tccaggcatc ctctgtaaac gggctggcgt agtgtggctt ggtcaaggaa 420
cagagacagg gctgcaca atg gct cag ctt cac tgc caa ctc tta ttc ttg   471
                   Met Ala Gln Leu His Cys Gln Leu Leu Phe Leu
                    1               5                  10

gga ttt aca ctc cta cag tcg tac aat gtc tca ggg tat ggt cca aac   519
Gly Phe Thr Leu Leu Gln Ser Tyr Asn Val Ser Gly Tyr Gly Pro Asn
            15                  20                  25

caa agg gcc cag aag aaa gga gac atc ata ctg gga ggt ctc ttc cca   567
Gln Arg Ala Gln Lys Lys Gly Asp Ile Ile Leu Gly Gly Leu Phe Pro
        30                  35                  40

ata cac ttt gga gta gcc gcc aag gat cag gac tta aaa tcg aga ccg   615
Ile His Phe Gly Val Ala Ala Lys Asp Gln Asp Leu Lys Ser Arg Pro
    45                  50                  55

gag gcg aca aaa tgt att cgg tac aat ttt cga ggc ttc cga tgg ctc   663
Glu Ala Thr Lys Cys Ile Arg Tyr Asn Phe Arg Gly Phe Arg Trp Leu
60                  65                  70                  75

cag gcg atg ata ttc gca att gaa gag att aac aac agt atg act ttc   711
Gln Ala Met Ile Phe Ala Ile Glu Glu Ile Asn Asn Ser Met Thr Phe
                80                  85                  90

ctg ccc aat atc acc ctg gga tat cgc ata ttt gac acg tgt aac acc   759
Leu Pro Asn Ile Thr Leu Gly Tyr Arg Ile Phe Asp Thr Cys Asn Thr
            95                 100                 105

gtg tcc aag gcg cta gag gca aca ctc agc ttt gtg gcc cag aac aaa   807
Val Ser Lys Ala Leu Glu Ala Thr Leu Ser Phe Val Ala Gln Asn Lys
        110                 115                 120

atc gac tcg ctg aac tta gat gag ttc tgt aac tgc tct gac cat atc   855
Ile Asp Ser Leu Asn Leu Asp Glu Phe Cys Asn Cys Ser Asp His Ile
    125                 130                 135

cca tcc aca ata gca gtg gtc ggg gca acc ggg tca gga atc tcc acg   903
Pro Ser Thr Ile Ala Val Val Gly Ala Thr Gly Ser Gly Ile Ser Thr
140                 145                 150                 155

gct gtg gcc aat cta ttg gga tta ttt tac att cca cag gtc agc tat   951
Ala Val Ala Asn Leu Leu Gly Leu Phe Tyr Ile Pro Gln Val Ser Tyr
                160                 165                 170

gcc tcc tcg agc agg ctg ctc agc aac aag aat gag tac aag gcc ttc   999
Ala Ser Ser Ser Arg Leu Leu Ser Asn Lys Asn Glu Tyr Lys Ala Phe
            175                 180                 185

ctg agg acc atc ccc aat gat gag caa cag gcc acg gcc atg gcc gag   1047
Leu Arg Thr Ile Pro Asn Asp Glu Gln Gln Ala Thr Ala Met Ala Glu
        190                 195                 200
```

FIG. 4A

```
atc atc gag cac ttc cag tgg aac tgg gtg gga acc ctg gca gcc gac     1095
Ile Ile Glu His Phe Gln Trp Asn Trp Val Gly Thr Leu Ala Ala Asp
    205                 210                 215

gat gac tat ggc cgc cca ggc att gac aag ttc cgg gag gag gcc gtt     1143
Asp Asp Tyr Gly Arg Pro Gly Ile Asp Lys Phe Arg Glu Glu Ala Val
220                 225                 230                 235

aag agg gac atc tgt att gac ttc agt gag atg atc tct cag tac tac     1191
Lys Arg Asp Ile Cys Ile Asp Phe Ser Glu Met Ile Ser Gln Tyr Tyr
                240                 245                 250

acc cag aag cag ttg gag ttc atc gcc gac gtc atc cag aac tcc tcg     1239
Thr Gln Lys Gln Leu Glu Phe Ile Ala Asp Val Ile Gln Asn Ser Ser
            255                 260                 265

gcc aag gtc atc gtg gtc ttc tcc aat ggc ccc gac ctg gag ccg ctc     1287
Ala Lys Val Ile Val Val Phe Ser Asn Gly Pro Asp Leu Glu Pro Leu
        270                 275                 280

atc cag gag ata gtt cgg aga aac atc acc gat cgg atc tgg ctg gcc     1335
Ile Gln Glu Ile Val Arg Arg Asn Ile Thr Asp Arg Ile Trp Leu Ala
    285                 290                 295

agc gag gct tgg gcc agc tct tcg ctc att gcc aag cca gag tac ttc     1383
Ser Glu Ala Trp Ala Ser Ser Ser Leu Ile Ala Lys Pro Glu Tyr Phe
300                 305                 310                 315

cac gtg gtc ggc ggc acc atc ggc ttc gct ctc agg gcg ggg cgt atc     1431
His Val Val Gly Gly Thr Ile Gly Phe Ala Leu Arg Ala Gly Arg Ile
                320                 325                 330

cca ggg ttc aac aag ttc ctg aag gag gtc cac ccc agc agg tcc tcg     1479
Pro Gly Phe Asn Lys Phe Leu Lys Glu Val His Pro Ser Arg Ser Ser
            335                 340                 345

gac aat ggg ttt gtc aag gag ttc tgg gag gag acc ttc aac tgc tac     1527
Asp Asn Gly Phe Val Lys Glu Phe Trp Glu Glu Thr Phe Asn Cys Tyr
        350                 355                 360

ttc acc gag aag acc ctg acg cag ctg aag aat tcc aag gtg ccc tcg     1575
Phe Thr Glu Lys Thr Leu Thr Gln Leu Lys Asn Ser Lys Val Pro Ser
    365                 370                 375

cac gga ccg gcg gct caa ggg gac ggc tcc aag gcg ggg aac tcc aga     1623
His Gly Pro Ala Ala Gln Gly Asp Gly Ser Lys Ala Gly Asn Ser Arg
380                 385                 390                 395
cgg aca gcc cta cgc cac ccc tgc act ggg gag gag aac atc acc agc     1671
Arg Thr Ala Leu Arg His Pro Cys Thr Gly Glu Glu Asn Ile Thr Ser
                400                 405                 410

gtg gag acc ccc tac ctg gat tat aca cac ctg agg atc tcc tac aat     1719
Val Glu Thr Pro Tyr Leu Asp Tyr Thr His Leu Arg Ile Ser Tyr Asn
            415                 420                 425

gta tac gtg gcc gtc tac tcc att gct cac gcc ctg caa gac atc cac     1767
Val Tyr Val Ala Val Tyr Ser Ile Ala His Ala Leu Gln Asp Ile His
        430                 435                 440
```

FIG. 4B

```
tct tgc aaa ccc ggc acg ggc atc ttt gca aac gga tct tgt gca gat    1815
Ser Cys Lys Pro Gly Thr Gly Ile Phe Ala Asn Gly Ser Cys Ala Asp
    445                 450                 455

att aaa aaa gtt gag gcc tgg cag gtc ctc aac cat ctg ctg cat ctg    1863
Ile Lys Lys Val Glu Ala Trp Gln Val Leu Asn His Leu Leu His Leu
460                 465                 470                 475

aag ttt acc aac agc atg ggt gag cag gtt gac ttt gac gat caa ggt    1911
Lys Phe Thr Asn Ser Met Gly Glu Gln Val Asp Phe Asp Asp Gln Gly
                480                 485                 490

gac ctc aag ggg aac tac acc att atc aac tgg cag ctc tcc gca gag    1959
Asp Leu Lys Gly Asn Tyr Thr Ile Ile Asn Trp Gln Leu Ser Ala Glu
            495                 500                 505

gat gaa tcg gtg ttg ttc cat gag gtg ggc aac tac aac gcc tac gct    2007
Asp Glu Ser Val Leu Phe His Glu Val Gly Asn Tyr Asn Ala Tyr Ala
        510                 515                 520

aag ccc agt gac cga ctc aac atc aac gaa aag aaa atc ctc tgg agt    2055
Lys Pro Ser Asp Arg Leu Asn Ile Asn Glu Lys Lys Ile Leu Trp Ser
    525                 530                 535

ggc ttc tcc aaa gtg gtt cct ttc tcc aac tgc agt cga gac tgt gtg    2103
Gly Phe Ser Lys Val Val Pro Phe Ser Asn Cys Ser Arg Asp Cys Val
540                 545                 550                 555

ccg ggc acc agg aag ggg atc atc gag ggg gag ccc acc tgc tgc ttt    2151
Pro Gly Thr Arg Lys Gly Ile Ile Glu Gly Glu Pro Thr Cys Cys Phe
                560                 565                 570

gaa tgc atg gca tgt gca gag gga gag ttc agt gat gaa aac gat gca    2199
Glu Cys Met Ala Cys Ala Glu Gly Glu Phe Ser Asp Glu Asn Asp Ala
            575                 580                 585

agt gcg tgt aca aag tgc ccg aat gat ttc tgg tcg aat gag aac cac    2247
Ser Ala Cys Thr Lys Cys Pro Asn Asp Phe Trp Ser Asn Glu Asn His
        590                 595                 600

acg tcg tgc atc gcc aag gag atc gag tac ctg tcg tgg acg gag ccc    2295
Thr Ser Cys Ile Ala Lys Glu Ile Glu Tyr Leu Ser Trp Thr Glu Pro
    605                 610                 615

ttc ggg atc gct ctg acc atc ttc gcc gta ctg ggc atc ctg atc acc    2343
Phe Gly Ile Ala Leu Thr Ile Phe Ala Val Leu Gly Ile Leu Ile Thr
620                 625                 630                 635

tcc ttc gtg ctg ggg gtc ttc atc aag ttc agg aac act ccc atc gtg    2391
Ser Phe Val Leu Gly Val Phe Ile Lys Phe Arg Asn Thr Pro Ile Val
                640                 645                 650

aag gcc acc aac cgg gag ttg tcc tac ctg ctg ctc ttc tcc ctc atc    2439
Lys Ala Thr Asn Arg Glu Leu Ser Tyr Leu Leu Leu Phe Ser Leu Ile
            655                 660                 665

tgc tgc ttc tcc agc tcg ctc atc ttc atc ggc gag ccc agg gac tgg    2487
Cys Cys Phe Ser Ser Ser Leu Ile Phe Ile Gly Glu Pro Arg Asp Trp
        670                 675                 680
```

FIG. 4C

```
acc tgt cgg ctc cgc caa ccg gcc ttt ggc atc agc ttc gtc ctg tgc    2535
Thr Cys Arg Leu Arg Gln Pro Ala Phe Gly Ile Ser Phe Val Leu Cys
    685                 690                 695

atc tcc tgc atc ctg gtg aag acc aac cgg gtg ctg ctg gtc ttc gag    2583
Ile Ser Cys Ile Leu Val Lys Thr Asn Arg Val Leu Leu Val Phe Glu
700                 705                 710                 715

gcc aag atc ccc acc agc ctc cac cgc aag tgg gtg ggc ctc aac ctg    2631
Ala Lys Ile Pro Thr Ser Leu His Arg Lys Trp Val Gly Leu Asn Leu
                720                 725                 730

cag ttc ctc ctg gtc ttc ctc tgc atc ctg gtg caa atc gtc acc tgc    2679
Gln Phe Leu Leu Val Phe Leu Cys Ile Leu Val Gln Ile Val Thr Cys
            735                 740                 745

atc atc tgg ctc tac acc gcg cct ccc tcc agc tac agg aac cat gag    2727
Ile Ile Trp Leu Tyr Thr Ala Pro Pro Ser Ser Tyr Arg Asn His Glu
        750                 755                 760

ctg gag gac gag gtc atc ttc atc acc tgc gac gag ggc tcg ctc atg    2775
Leu Glu Asp Glu Val Ile Phe Ile Thr Cys Asp Glu Gly Ser Leu Met
    765                 770                 775

gcg ctg ggc ttc ctc atc ggc tac acc tgc ctc ctc gcc gcc atc tgc    2823
Ala Leu Gly Phe Leu Ile Gly Tyr Thr Cys Leu Leu Ala Ala Ile Cys
780                 785                 790                 795

ttc ttc ttc gcc ttc aag tcc cgt aag ctg ccg gag aac ttc aac gag    2871
Phe Phe Phe Ala Phe Lys Ser Arg Lys Leu Pro Glu Asn Phe Asn Glu
                800                 805                 810

gct aag ttc atc acc ttc agc atg ttg atc ttc ttc atc gtc tgg atc    2919
Ala Lys Phe Ile Thr Phe Ser Met Leu Ile Phe Phe Ile Val Trp Ile
            815                 820                 825

tcc ttc atc ccc gcc tat gtc agc acc tac ggc aag ttt gtg tcg gcc    2967
Ser Phe Ile Pro Ala Tyr Val Ser Thr Tyr Gly Lys Phe Val Ser Ala
        830                 835                 840

gtg gag gtg att gcc atc ctg gcc tcc agc ttc ggg ctg ctg ggc tgc    3015
Val Glu Val Ile Ala Ile Leu Ala Ser Ser Phe Gly Leu Leu Gly Cys
    845                 850                 855

att tac ttc aac aag tgt tac atc atc ctg ttc aag ccg tgc cgt aac    3063
Ile Tyr Phe Asn Lys Cys Tyr Ile Ile Leu Phe Lys Pro Cys Arg Asn
860                 865                 870                 875

acc atc gag gag gtg cgc tgc agc acg gcg gcc cac gcc ttc aag gtg    3111
Thr Ile Glu Glu Val Arg Cys Ser Thr Ala Ala His Ala Phe Lys Val
                880                 885                 890

gcg gcc cgg gcc acc ctc cgg cgc agc gcc gcg tct cgc aag cgc tcc    3159
Ala Ala Arg Ala Thr Leu Arg Arg Ser Ala Ala Ser Arg Lys Arg Ser
            895                 900                 905

agc agc ctg tgc ggc tcc acc atc tcc tcg ccc gcc tcg tcc acc tgc    3207
Ser Ser Leu Cys Gly Ser Thr Ile Ser Ser Pro Ala Ser Ser Thr Cys
        910                 915                 920
```

FIG. 4D 01-24-2003)

```
ggg ccg ggc ctc acc atg gag atg cag cgc tgc agc acg cag aag gtc    3255
Gly Pro Gly Leu Thr Met Glu Met Gln Arg Cys Ser Thr Gln Lys Val
    925                 930                 935

agc ttc ggc agc ggc acc gtc acc ctg tcg ctc agc ttc gag gag aca    3303
Ser Phe Gly Ser Gly Thr Val Thr Leu Ser Leu Ser Phe Glu Glu Thr
940                 945                 950                 955

ggc cga tac gcc acc ctc agc cgc acg gcc cgc agc agg aac tcg gcg    3351
Gly Arg Tyr Ala Thr Leu Ser Arg Thr Ala Arg Ser Arg Asn Ser Ala
                960                 965                 970

gat ggc cgc agc ggc gac gac ctg cca tct aga cac cac gac cag ggc    3399
Asp Gly Arg Ser Gly Asp Asp Leu Pro Ser Arg His His Asp Gln Gly
            975                 980                 985

ccg cct cag aaa tgc gag ccc cag ccc gcc aac gat gcc cga tac aag    3447
Pro Pro Gln Lys Cys Glu Pro Gln Pro Ala Asn Asp Ala Arg Tyr Lys
        990                 995                 1000

gcg gcg ccg acc aag ggc acc cta gag tcg ccg ggc ggc agc aag gag    3495
Ala Ala Pro Thr Lys Gly Thr Leu Glu Ser Pro Gly Gly Ser Lys Glu
    1005                1010                1015

cgc ccc aca act atg gag gaa acc taa tccaactcct ccatcaaccc          3542
Arg Pro Thr Thr Met Glu Glu Thr  *
1020                1025           (SEQ ID NO: 7)

caagaacatc ctccacggca gcaccgtcga caactgacat caactcctaa ccggtggctg 3602
cccaacctct cccctctccg gcactttgcg ttttgctgaa gattgcagca tctgcagttc 3662
cttttatccc tgattttctg acttggatat ttactagtgt gcgatggaat atcacaacat 3722
aatgagttgc acaattaggt gagcagagtt gtgtcaaagt atctgaacta tctgaagtat 3782
ctgaactact ttattctctc gaattgtatt acaaacattt gaagtatttt tagtgacatt 3842
atgttctaac attgtcaaga taatttgtta caacatataa ggtaccacct gaagcagtga 3902
ctgagattgc cactgtgatg acagaactgt tttataacat ttatcattga aacctggatt 3962
gcaacaggaa tataatgact gtaacaaaaa aattgttgat tatcttaaaa atgcaaattg 4022
taatcagatg tgtaaaattg gtaattactt ctgtacatta aatgcatatt tcttgataaa 4082
aaaaaaaaaa aaaaaaaaaa aaaaaaaaaa aaaagcggcc cgacagcaac gg         4134

                                                      (SEQ ID NO: 8)
```

FIG. 4E

FIG. 7
Panel A
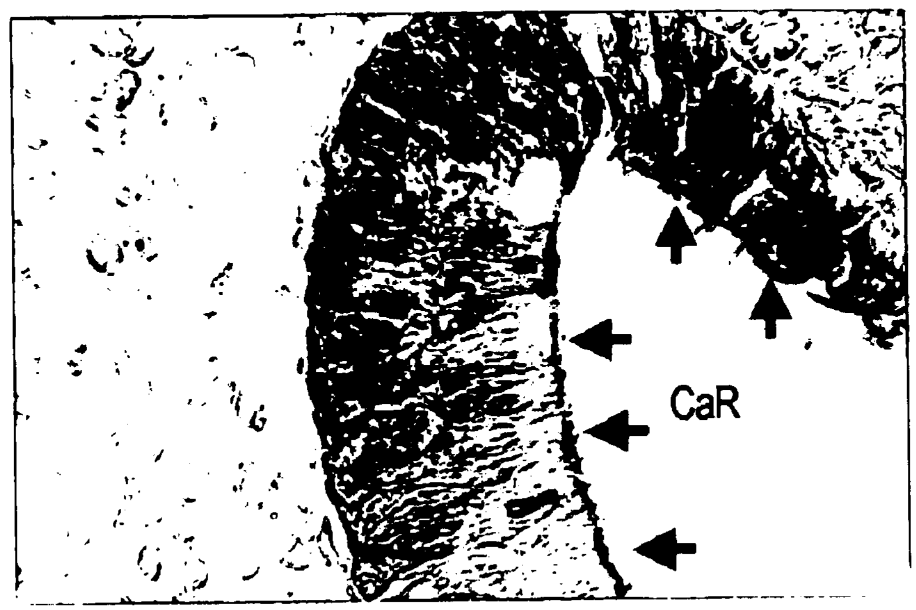
Panel B
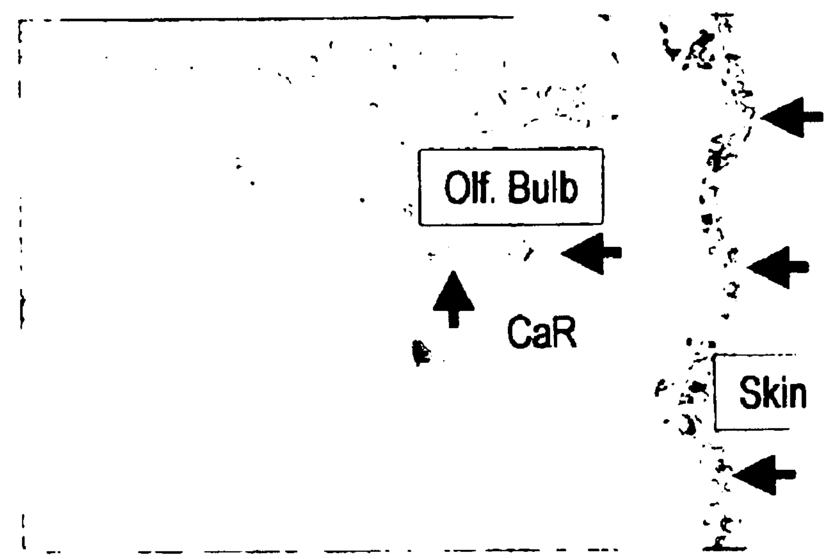

Atlantic Salmon Tissues

Repeated Stimulation of Preparation with Single Continuous Recording

METHODS FOR GROWING AND IMPRINTING FISH USING AN ODORANT

RELATED APPLICATION

This application claims the benefit of U.S. Provisional Application No. 60/328,464, filed Oct. 11, 2001. The entire teachings of the above application are incorporated herein by reference.

BACKGROUND OF THE INVENTION

Although great advantages exist in being able to attract or repel fish, such methods have not yet been well developed or understood. Hence, improved methods for attracting or repelling fish are needed.

SUMMARY OF THE INVENTION

The present invention relates to a discovery that fish can be imprinted with an odorant (e.g., an attractant or repellant) so that, when the fish are later exposed to the odorant, they can react to the odorant e.g., distinguish the odorant or be sensitized to the odorant through manipulating fundamental biological mechanisms of the fish. In particular, the present invention encompasses the discovery that a protein, called a Polyvalent Cation Sensing Receptor (PVCR), has a role in allowing fish to "sense" ions and amino acids, and works with odorant receptors, under certain conditions, to imprint fish with an odorant. The PVCR interacts with odorant receptors to alter olfactory sensing capabilities of the fish.

The present invention applies to several types of aquatic species including freshwater fish, marine fish and anadromous fish. In one embodiment, anadromous fish can be imprinted during various phases including the larval stage (e.g., yolk sac larvae, or first feeding larvae) or the smoltification stage. In nature, many anadromous fish live most of their adulthood in seawater, but swim upstream to freshwater for the purpose of breeding. As a result, anadromous fish hatch from their eggs in freshwater. As these fish grow, they swim downstream and gradually adapt to the seawater. To raise these fish, fish hatcheries transfer these fish from freshwater to seawater when they undergo smoltification. Smoltification is the stage at which fish become able to adapt from freshwater to seawater. Accordingly, while fish are being imprinted to an odorant, they are maintained in freshwater, and subsequently transferred to seawater.

The present invention relates to methods of imprinting fish to at least one fish odorant (e.g., fish attractant or fish repellant) by adding at least one PVCR modulator to a first body of water (e.g., freshwater) in an amount sufficient to modulate expression and/or sensitivity of at least one PVCR; and adding feed for fish consumption to the water. The feed contains at least one odorant and an amount of NaCl sufficient to contribute to a significantly increased level of the PVCR modulator in serum of the fish. The PVCR modulator alters olfactory sensing of fish to the odorant. Modulated expression of at least one PVCR can be maintained until the fish are transferred to a second body of water. In one embodiment, fish (e.g., marine fish or anadromous fish) can be transferred to seawater, and in another embodiment fish (e.g., freshwater fish) can be transferred to freshwater without the PVCR modulator added to it. In yet another embodiment, fish can be transferred to freshwater having the PVCR modulator, but without the odorant added to it. The present invention also includes providing a source of said odorant after fish have been transferred to the second body of water. When the fish are transferred to the second body of water, the olfactory sensing apparatus of the fish can distinguish the odorant or are sensitized to the odorant. Altering olfactory sensing of fish to the odorant further includes generating an olfactory nerve impulse after binding of the odorant to the olfactory lamellae in the fish. The methods also include adding a PVCR modulator to the feed. Examples of fish attractants are amino acids, nucleotides, organic compounds, and combination thereof. Compounds derived from performing a mammalian finger rinse, for example, can be used as a fish repellant.

In another embodiment, the present invention relates to methods of imprinting fish to at least one odorant for fish by adding at least one PVCR modulator to the first body of water (e.g., freshwater) in an amount sufficient to modulate expression and/or sensitivity of at least one PVCR; adding at least one odorant to the water; and adding feed for fish consumption to the water, wherein the feed contains an amount of NaCl sufficient to contribute to a significantly increased level of the PVCR modulator in serum of the fish. The PVCR modulator alters olfactory sensing of fish to the odorant. The present invention also includes providing a source of said odorant after fish have been transferred to a second body of water. When the fish are transferred to the second body of water, the olfactory sensing apparatus of the fish can distinguish the odorant or are sensitized to the odorant.

The present invention also includes methods for growing anadromous fish so that the anadromous fish are sensitized to at least one fish odorant by imprinting the anadromous fish with the fish attractant in freshwater during smoltification, as described herein; transferring anadromous fish to seawater; and adding feed for fish consumption to the seawater, wherein the feed contains a source of nutrition and the attractant used for imprinting. When transferred to seawater, the olfactory sensing apparatus of these imprinted fish can distinguish the attractant or are sensitized to the attractant.

The invention also embodies feed for consumption by anadromous fish in freshwater. The feed comprises one or more sources of nutrition; an amount of NaCl between about 10,000 mg/kg and about 100,000 mg/kg; and at least one fish attractant. The feed can further include adding a PVCR modulator such as tryptophan in an amount between about 1 and about 10 gm/kg. Similarly, the present invention includes feeds for consumption by anadromous fish in seawater. This seawater feed comprises a source of nutrition; and the fish attractant to which fish have been imprinted.

The present invention also relates to methods of identifying a fish odorant and its modulation by at least one PVCR present in the olfactory system of fish, by exposing the odorant to be tested to the tissue of fish, wherein at least one odorant receptor and at least one PVCR are present in tissue; and assessing the magnitude or characteristics of an olfactory nerve response. The presence of an olfactory nerve impulse indicates the compound is an odorant or PVCR modulator in the water in contact with the fish olfactory epithelium. The absence of a olfactory nerve impulse indicates the compound is not an odorant or PVCR modulator in the water in contact with the fish olfactory epithelium. Alterations in the magnitude or characteristics of the olfactory nerve impulse upon exposure of the olfactory epithelium to various combinations of odorants and PVCR modulators indicates modifications of the olfactory nerve signals from odorant receptors and/or PVCR proteins present in this tissue. Such assays can be further modified by exposure of the fish to a PVCR modulator present in freshwater as well as feed added to the freshwater before assay using these methods. Assays known in the art such as behavioral attractant assays or behavioral avoidance assays can be performed to determine whether the odorant is an attractant or repellant, respectively.

The present invention includes methods of increasing food consumption of anadromous fish, methods of increasing the growth rate of one or more anadromous fish, methods of increasing survival of anadromous fish after their transfer to seawater, and methods for improving the feed conversion ratio (FCR) for anadromous fish. These methods are accomplished with knowledge of the roles of PVCR proteins in various organs including the olfactory lamellae, brain and gastrointestinal tract. In the fish olfactory system, it has been discovered that PVCR proteins perform controlling functions enabling fish to "smell" the ionic composition of the surrounding water as well as integrate specific attractants with water salinity. In the fish gastrointestinal tract, it has been discovered that PVCR proteins act as dual sensors for both the ionic and nutrient composition of intestinal contents. These dual functions of PVCRs permit cells lining the fish G.I. tract to integrate information on the ionic composition of water and the amino acid consumption derived from food to optimally utilize nutrients for growth. These methods can be performed by subjecting the anadromous fish to at least one PVCR modulator in the freshwater in an amount sufficient to modulate expression and/or sensitivity of at least one PVCR; adding feed for fish consumption to the freshwater, wherein the feed contains an amount of NaCl sufficient to contribute to a significantly increased level of the PVCR modulator in serum of the anadromous fish and at least one fish attractant; transferring the anadromous fish to seawater; and adding feed for fish consumption to the seawater. The PVCR modulator alters olfactory sensing of fish to the attractant. The seawater feed contains a source of nutrition and the attractant used during imprinting in an amount sufficient to modulate the PVCR in olfactory tissue of the fish The present invention also relates to methods of attracting or homing anadromous fish that have been imprinted. The anadromous fish were imprinted to at least one attractant in freshwater during smoltification, as described herein, whereby the olfactory sensing apparatus of fish can distinguish the attractant or are sensitized to the attractant; transferring anadromous fish to seawater; and exposing the fish to the attractant used during the imprinting process in a sufficient amount to modulate the PVCR in the olfactory sensing apparatus of the fish. In seawater, the fish can be exposed to the attractant by adhering the attractant to an object (e.g., netting or fish lure) and placing the object having the attractant adhered thereto in the seawater.

In another embodiment, the present invention pertains to methods of repelling anadromous fish that have been imprinted, as described herein, so that the fish are sensitized to at least one fish repellant. The method includes imprinting the anadromous fish to at least one repellant in freshwater during smoltification, whereby the olfactory sensing apparatus of fish can distinguish the repellant or are sensitized to the repellant; transferring anadromous fish to seawater; and exposing the fish to the same repellant used during the imprinting process in a sufficient amount to modulate the PVCR in the olfactory sensing apparatus of the fish. The repellant can be adhered to an object that is placed in the seawater.

The present invention provides numerous advantages including, for example: allowing hatcheries to increase food consumption of fish so that they grow faster; allowing for the homing of fish for improved breeding; allowing one to more easily attract fish into a net or by a lure; and allowing fish to be repelled from dangerous areas.

BRIEF DESCRIPTION OF THE DRAWINGS

FIG. 1 is a diagram illustrating the partial nucleotide (SEQ ID NO:1) and amino acid (SEQ ID NO:2) sequences of the polyvalent cation-sensing receptor (PVCR) of Atlantic salmon (*Salmo salar*).

FIG. 2 is a diagram illustrating the partial nucleotide (SEQ ID NO:3) and amino acid (SEQ ID NO:4) sequences of the PVCR of arctic char (*Salvelinus alpinus*).

FIG. 3 is a diagram illustrating the partial nucleotide (SEQ ID NO:5) and amino acid (SEQ ID NO:6) sequences of the PVCR of rainbow trout (*Onchorhynchus mykiss*).

FIGS. 4A–E are diagrams illustrating full length nucleic acid (SEQ ID NO.: 7) and amino acid (SEQ ID NO.: 8) sequence of the shark kidney cation receptor ("SKCaR").

FIG. 7 are photographs of immunocytochemistry showing the PVCR protein expression in the developing nasal lamellae and olfactory bulb after hatching of Atlantic salmon using an anti-PVCR antibody.

Figure 13:
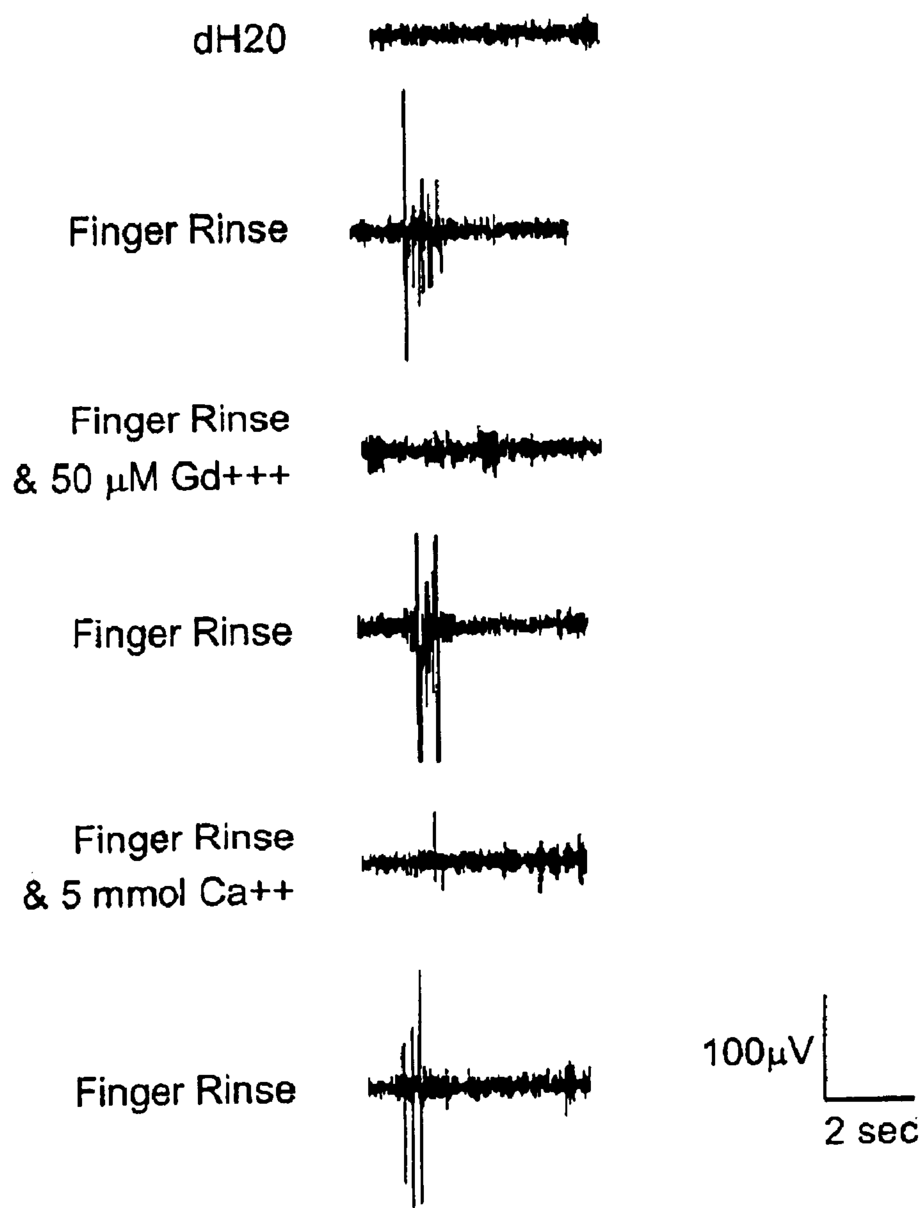

FIG. 13 shows raw recording from high resistance electrodes of olfactory nerve impulse in the presence of a repellant (finger rinse) and in the presence of a PVCR agonist (gadolinium) and a repellant (finger rinse). The figure shows that the olfactory nerve impulse to the repellant is reversibly altered in the presence of a PVCR agonist.

Figure 14:
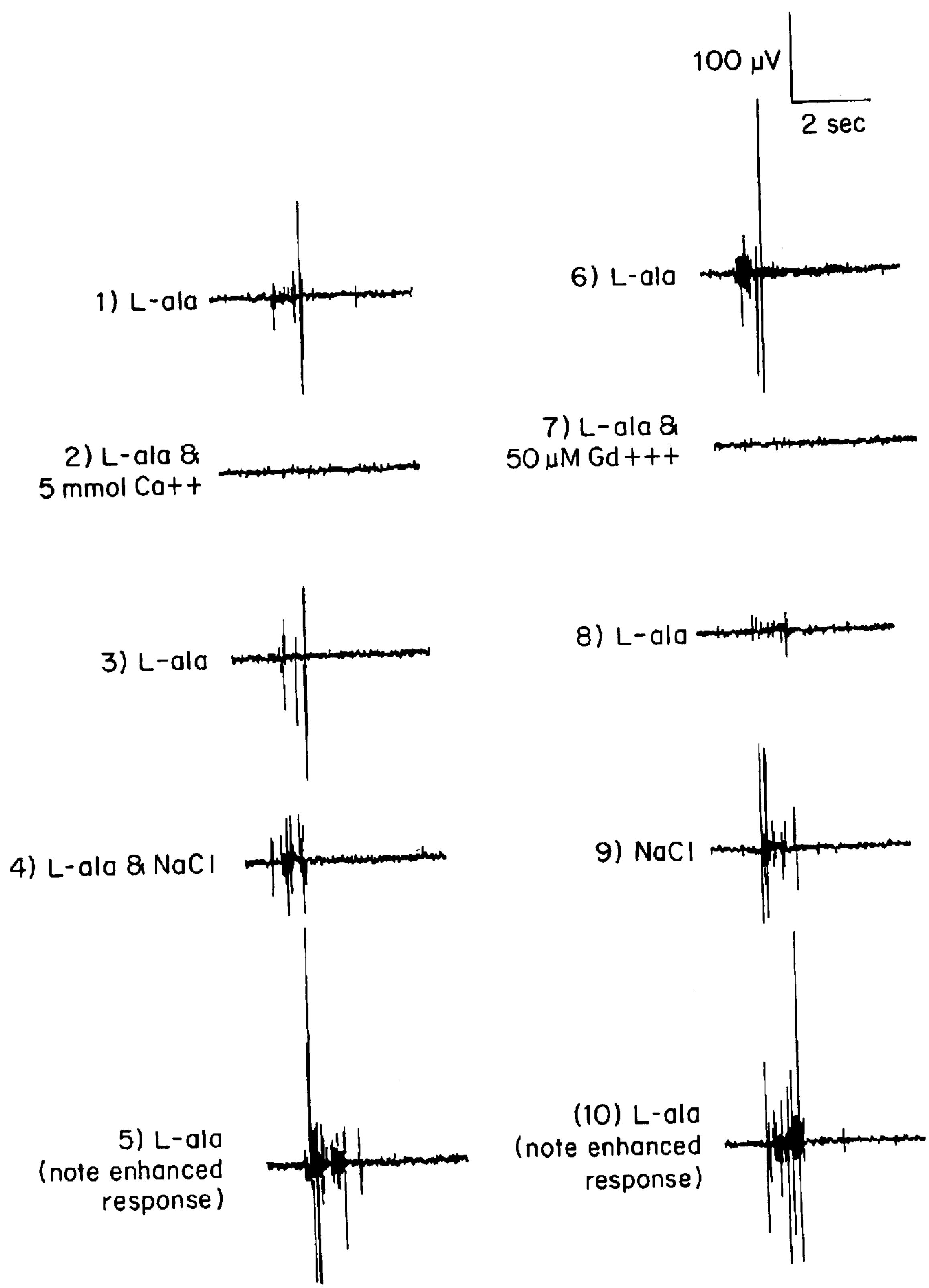
Figure 15:
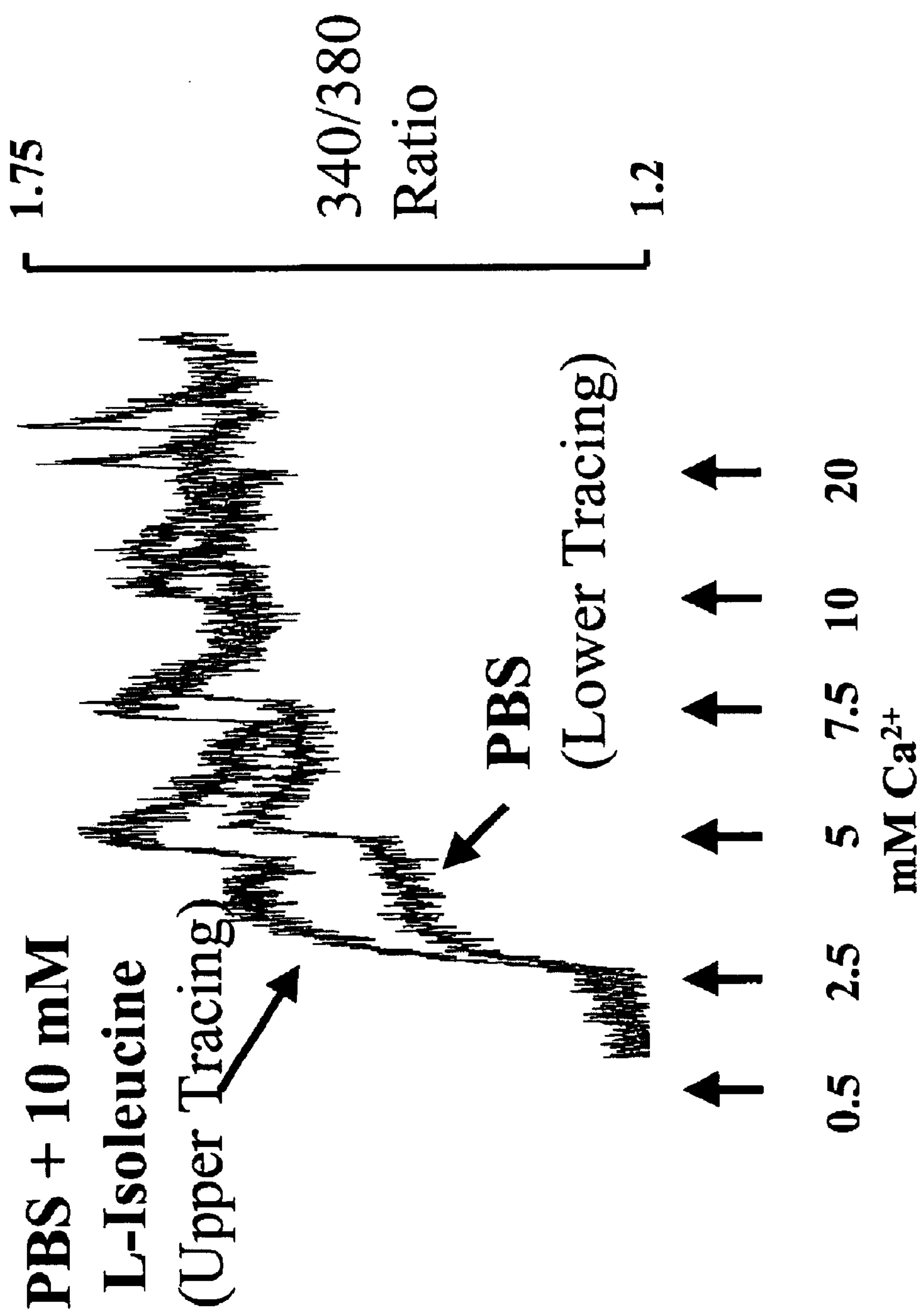

FIG. 14 shows the raw recordings from high resistance electrodes of freshwater adapted Atlantic Salmon in response to a series of repeated stimuli (L-alanine or NaCl) in 2 minute intervals. The figure shows that the olfactory nerve impulse to the attractant is reversibly altered in the presence of a PVCR agonist FIG. 15 is a graphical representation of the ratio from FURA-2 cells expressing a PVCR in the presence or absence of 10 mM L-Isoleucine in various concentrations (0.5, 2.5, 5.0, 7.5, 10.0 and 20.0 mM) of extracellular calcium ($Ca^{2+}$).

Figure 16:
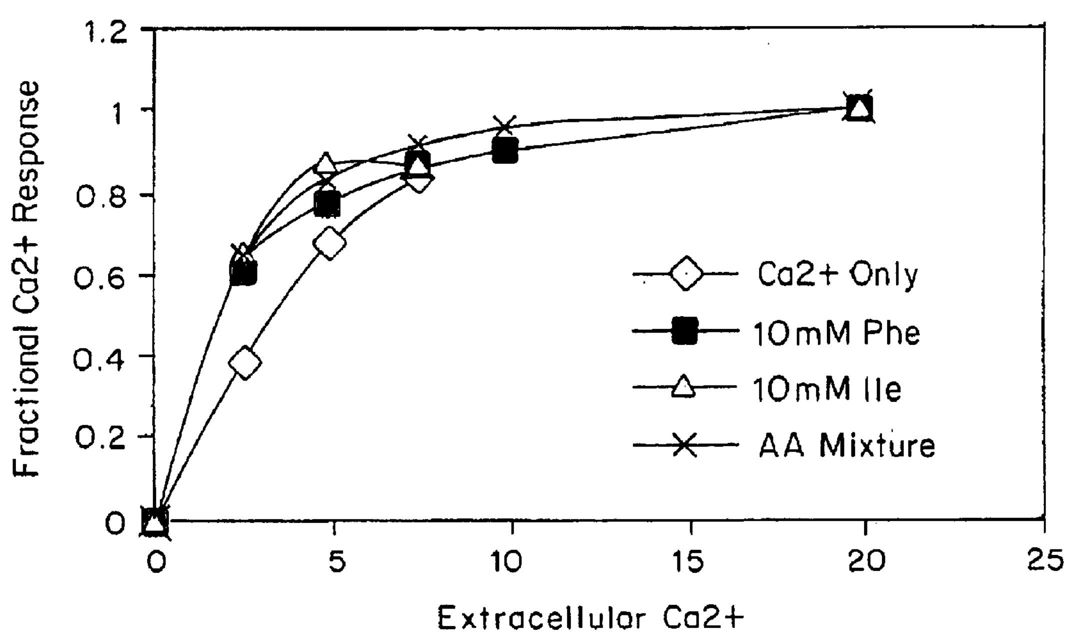

FIG. 16 is a graphical representation of the fractional $Ca^{2+}$ response, as compared to the extracelluar $Ca^{2+}$ (mM) for the PVCR in $Ca^{2+}$ only, Phenylalanine, Isoleucine, or AA Mixture (a variety of L-isomers in various concentrations).

Figure 17:
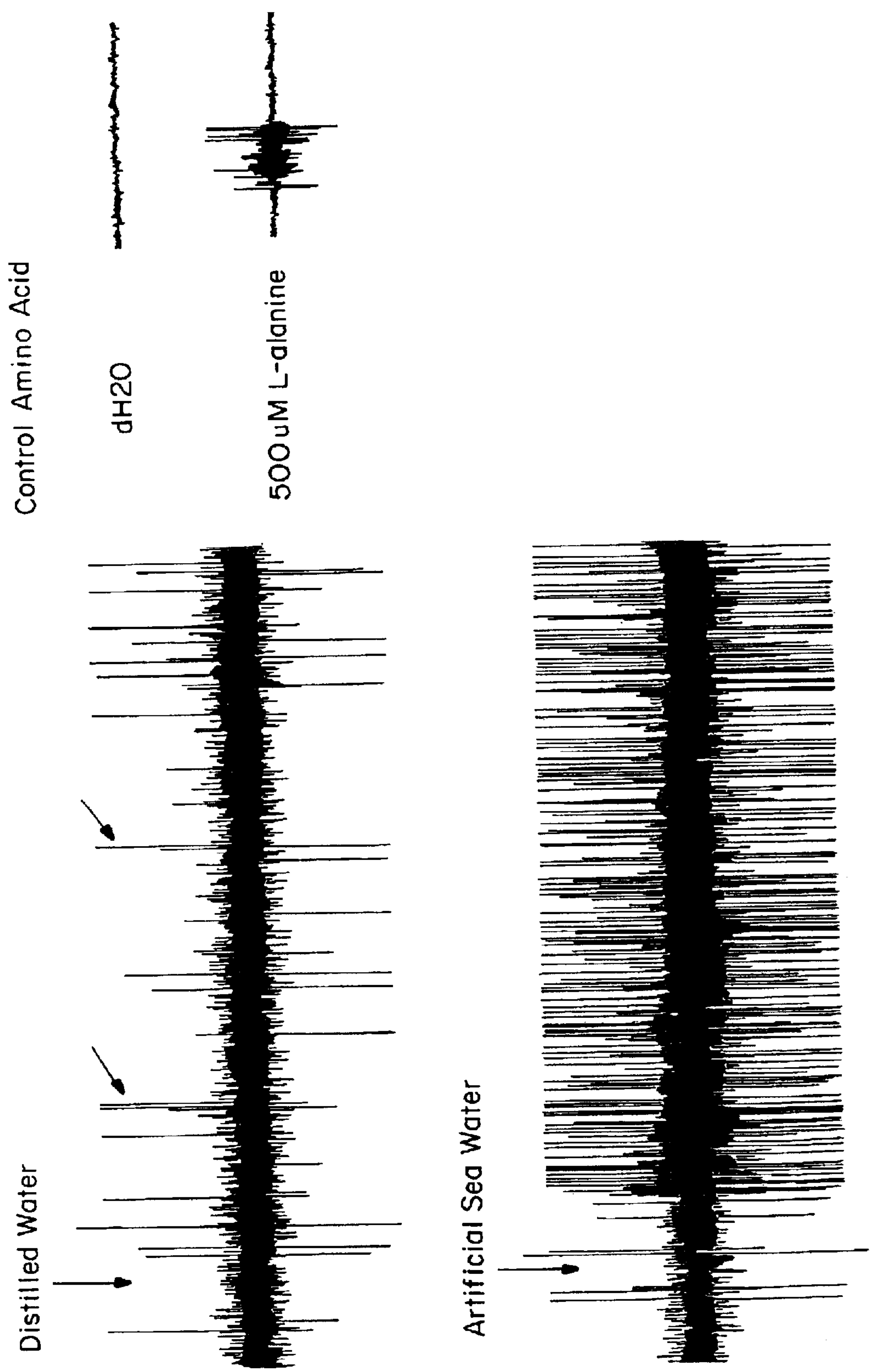

FIG. 17 is a graphical representation of olfactory nerve recordings of freshwater Atlantic Salmon smolt olfactory epithelia in distilled water, ASW, and control amino acid (500 $\mu$M L-alanine).

DETAILED DESCRIPTION OF THE INVENTION

The present invention relates to the fundamental discovery that fish can be imprinted with an odorant (e.g., an attractant or repellant) during certain stages of development, and later when the fish are exposed to that same odorant, they can readily distinguish the odorant or are sensitized to the odorant. In particular, the present invention encompasses the newly discovered understanding that a Polyvalent Cation Sensing Receptor (PVCR), has a role in allowing fish to "sense" both ions and amino acids. The PVCR proteins permit fish to "sense" both water salinity (e.g., ion concentrations) and concentrations of amino acids in the water that surrounds them, in their bodily fluids and in the contents of their gastrointestinal tract. The PVCR works with odorant receptors to imprint fish to an odorant, so that modulators of the PVCR alter olfactory sensing capabilities of the fish.

The methods of the present invention pertain to all types of aquatic species including freshwater fish, marine fish, anadromous fish, crustations, molusks and echinoderms.

Marine fish are fish that live, at least for most of their adult lives, in seawater. Marine fish include, for example, Cod, Haddock, Hake, Halibut, Mackerel, Pollock, Sea Bass, Swordfish, Tuna, Winter Flounder, and Summer Flounder. Freshwater fish are fish that live, at least for the most of their adult lives, in freshwater. The terms "marine fish" and "freshwater fish" are understood by one of skill in the art.

Anadromous fish are fish that swim from seawater to freshwater to breed. Anadromous fish include, for example, salmon (e.g, Atlantic Salmon (*Salmo salar*), Coho Salmon (*Oncorhynchus kisutch*), Chum Salmon (*Oncorhynchus keta*), Chinook Salmon (*Oncorhynchus tshawytscha*), Pink Salmon (*Oncorhynchus gorbuscha*), Sockeye Salmon (*Oncorhynchus nerka*)), char (e.g., Arctic Char (*Salveninus alpinus*)) and trout (e.g., Rainbow Trout (*Oncorhynchus mykiss*)). Anadromous fish also include fish that are unable to swim to seawater (e.g., landlocked), but have the physiological mechanisms to adapt to seawater. The term "pre-adult anadromous fish," as used herein, refers to anadromous fish that have not yet adapted to seawater. These fish are generally juvenile fish. Pre-adult anadromous fish include, but are not limited to fish that are fingerlings, parr or smolts. As used herein, "smolt" refers to fish undergoing physiological changes that allows the fish to adapt to seawater, or survive upon subsequent transfer to seawater. The term, "smolt," also refers to a fish that is not at the precise developmental stage to survive uninjured upon transfer to seawater, but rather is one of a population of fish wherein, based on a statistical sampling and evaluation, the population of fish is determined to be at a physiological stage ready for transfer to seawater.

Anadromous fish such as salmon are capable of returning to a specific site in a freshwater stream where they were hatched despite years of travel and residence in large tracts of the ocean during their adulthood. To accomplish this feat, anadromous fish undergo imprinting during various phases of their lifecycle that enables them to recognize and return to a specific site. One such phase is during their larval stage of life when they are hatching in a streambed and the another phase is during smoltification in the river when they adapt for life in seawater. While it has been demonstrated that exposure of salmon to a specific odorant during smoltification imprints the corresponding adult salmon to return to the site containing that odorant, until the discovery of the present invention it was unclear exactly how these fish accomplish this task with either natural or artificial odorants. Spawning migrations by fish to specific areas of estuaries or rivers are not restricted to anadromous fish species. Marine flatfish such as flounder migrate from deep ocean water to specific estuaries near coastal rivers to spawn and then return to the ocean.

An improved ability to attract or repel fish would greatly aid hatchery producers in the breeding and production of fish for both restocking of depleted natural populations as well as commercial production in ocean netpens or by ocean ranching. Present day methods include restocking of wild fish populations via the production of a large numbers of juvenile fish in hatcheries followed by their release into the wild at the mouths of rivers or estuaries. Use of attractants for these fish might aid in their efficient harvesting by fishermen using either hooks or nets. In a similar manner, commercial production of large numbers of juvenile salmon for ocean ranching occurs in regions such as Alaska and the Pacific Northwest. However, such methods are not efficient in that large numbers of fish do not survive their transfer to the wild and thus huge numbers of fish are raised and released to provide for returns to the freshwater site of 1–20% depending on the specific species. Restocking efforts in wild fish populations are hampered by the straying of large number of juvenile fish into water intakes of power plants and dam turbines. Successful aversion of such juvenile fish after their release from the hatchery by repellants would effectively increase the efficiency of these restocking efforts, and/or prevent problems caused by the fish with respect to the operation of the power plants or turbines. Moreover, large numbers of salmon and trout are produced in freshwater hatcheries whereupon they are transferred directly to ocean netpens for growout within a confined space. Prior to the present invention, salmon smolt produced by this direct transfer method encounter multiple problems adapting to their new seawater environment. Delays in feeding after seawater transfer and remodeling of gut function for seawater life presently reduce the growth of these fish after seawater transfer.

The present invention relates to methods of growing fish. Fish hatcheries have experienced difficulty in raising anadromous fish because the window of time in which the pre-adult fish adapts to seawater (e.g., undergoes smoltification) is short-lived, and can be difficult to pinpoint. So, when the fish are transferred to seawater, they often experience stress (e.g., osmotic shock) and eat poorly. Several of the fish that are transferred die as a result. The present invention provides methods and compositions that allow fish to better adapt to seawater and to increase food consumption by imprinting the fish with an attractant in freshwater having a PVCR modulator, and after the transfer to seawater, providing fish with a feed that has the same attractant.

The PVCR modulator alters the olfactory sensing of the fish to the odorant. In some cases, the presence of a (e.g., at least one) PVCR modulator in freshwater reversibly reduces or ablates the fish's ability to sense certain odorants. In other cases it can be heightened or increased. By exposing the fish (e.g., anadromous fish) in freshwater having a PVCR modulator to an odorant, the fish have a decreased or dulled response to an odorant. The PVCR allows fish to "sense" various types of modulators, which are further defined herein. The term "sense" or "sensing" refers to the PVCR's ability to alter its expression and/or sensitivity in response to a PVCR modulator. In addition to modulating the PVCR, the sensing of an odorant can involve altering one or more olfactory receptors. The PVCR can work, for example, with one or more olfactory receptors to generate of the nerve impulse during sensing of an odorant. Generation of this nerve impulse occurs upon binding of the odorant to the olfactory lamellae in the fish.

The fish olfactory system consists of the olfactory epithelium, olfactory nerve and olfactory bulb of the brain. Using methods of the present invention, anti-PVCR antiserum and RT-PCR show that each component of the fish olfactory system contains at least one PVCR protein. The present invention relates to methods that demonstrate that at least one PVCR functions to allow fish to "smell" the salinity of surrounding water via sensing of ionic concentrations of $Ca^{2+}$, $Mg^{2+}$ and $Na^{+}$ by PVCRs. The present invention further relates to methods whereby exposure of fish olfactory epithelium to PVCR modulators such as $Ca^{2+}$, $Mg^{2+}$, $Gd^{3+}$ and neomycin produce a concentration-dependent olfactory nerve impulse in concentration ranges that correspond to those occurring in salinity ranges encountered by wild salmon. These data verify the presence of functional PVCR proteins in olfactory epithelial cells and their key role in salinity sensing by fish.

These same methods were used to demonstrate that simultaneous exposure of the olfactory epithelium to an odorant (such as amino acid attractant or repellant) and a PVCR agonist (Ca2+ or Gd3+) alters the magnitude and/or characteristics of the resulting olfactory nerve impulse. This alteration is produced by interactions between the signals produced by the odorant receptor (sensing specific odorant molecules) and the PVCR (sensing both salinity and amino acids if present). The PVCR modulates or alters odorant receptors and their ability to generate a nerve impulse.

The presence of both PVCR proteins (sensing salinity and selected amino acids) together with odorant receptors (sensing specific odorant molecules) provides an explanation for how salmon can sense both the odor of specific rivers or streams as well as their salinity profile as they return home to spawn.

Freshwater and marine fish sense odorants in aquatic environments that vary widely in their ionic composition. PVCRs in olfactory epithelial cells play a significant role in allowing olfactory cells to provide for a meaningful response to odorants over a wide range of ionic environments. Moreover, PVCRs in specific olfactory cells permit freshwater and marine fish to "smell" or sense water salinity. PVCRs can sense various modulators, as described herein, and in particular amino acids and divalent cations.

The presence of PVCR modulators in the surrounding freshwater as well as serum of the fish alter the expression and/or sensitivity of at least one PVCR in a manner similar to that which normally occurs only after the fish has been transferred to seawater. Thus, instead of imprinting on odorants present in food or water after their transfer to seawater, anadromous fish imprint on odorants in a manner identical to that occurring in seawater but surprisingly the fish remain in freshwater. When the fish are transferred to seawater, the olfactory sensing apparatus of the fish has already fully adapted and imprinted to a seawater environment and the fish can readily distinguish and recall the odorant in seawater.

An odorant is a compound that binds to olfactory receptors and causes fish to sense odorants. Generation of an olfactory nerve impulse occurs upon binding of the odorant to the olfactory lamellae. A fish odorant is either a fish attractant or fish repellant. A fish attractant is a compound to which fish are attracted. The sensitivity of the attractant is modulated, at least in part, by the sensitivity and/or expression of the PVCR in the olfactory apparatus of the fish in response to a PVCR modulator. Examples of attractants include amino acids (e.g., L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine), nucleotides (e.g., inosine monophosphate), organic compounds (e.g., glycine-betaine and trimethylamine oxide), or a combination thereof. Similarly, a fish repellant is a compound that fish are repelled by, and the sensitivity of the fish to the repellant is altered through expression and/or sensitivity of a PVCR in the olfactory apparatus of the fish in the presence of a PVCR modulator. An example of a repellant is a "finger rinse" which is a mixture of mammalian oils and fatty acids produce by the epidermal cells of the skin, and is left behind after human fingers are rinsed with an aqueous solution. Methods for performing a finger rinse is known in the art and is described in more detailed in the Exemplification Section.

During the time the fish are exposed to a PVCR modulator and an odorant in freshwater, they become "imprinted" with the odorant. The process of imprinting the fish with an odorant refers to creating a lasting effect or impression on the fish so that the fish can "react" to the odorant, e.g., they are sensitized to the odorant or can distinguish the odorant. Being sensitized to the odorant refers to the fish's ability to more easily recognize or recall the odorant. Distinguishing an odorant refers to the fish's ability to differentiate among one or more odorants, or have a preference for one odorant over another. In one embodiment, the invention pertains to methods of imprinting the fish with an attractant and modulating the PVCR, as further described herein, and then providing a unique feed composition that has the same attractant.

In particular, the methods of growing an fish include imprinting the fish to the attractant by adding at least one PVCR modulator (e.g., calcium and magnesium) to the freshwater, and adding a specially made or modified feed to the freshwater for consumption by the fish. The feed contains a sufficient amount of sodium chloride (NaCl) (e.g., between about 1% and about 10% by weight, or about 10,000 mg/kg to about 100,000 mg/kg) to significantly increase levels of the PVCR modulator in the serum and an attractant (e.g., between trace amounts and about 100 mg/kg). This amount of NaCl in the feed causes or induces the anadromous fish to drink more freshwater. Since the freshwater contains a PVCR modulator and the fish ingest increased amounts of it, the serum level of the PVCR modulator significantly increases in the fish, and causes modulated (e.g., increased and/or decreased) PVCR expression and/or altered PVCR sensitivity. The PVCR modulator alters the olfactory sensing of the fish to the attractant, as described herein.

In another embodiment, the fish (e.g., anadromous fish) are imprinted, not by adding the odorant to the feed, but by adding an odorant to the freshwater having a PCVR modulator (the PVCR modulator environment) e.g., while the fish are undergoing smoltification or are in certain larval stages. The fish are subjected to the same steps, as described herein. Namely, the fish are in the PVCR modulator environment and fed a diet having NaCl and, optionally, a PVCR modulator (such as tryptophan), except the odorant is added the freshwater water rather than the feed. The odorant is added to the freshwater in an amount between about 1 nanomolar and about 500 millimolar. This process imprints the fish with the odorant by modulating the expression and/or sensitivity of the PVCR in the olfactory apparatus, such that the olfactory sensing apparatus of the fish can distinguish the odorant or are sensitized to the odorant.

The present invention, in yet another embodiment, includes introduction of the PVCR modulator and odorant in a first body of water. After the fish are imprinted, they are transferred to a second body of water. Depending on the type of fish being subjected to the steps of the present invention, the fish can come from freshwater or seawater. For example, pre-adult anadromous fish are maintained in freshwater prior to carrying out the steps of the present invention. During smoltification, as described herein, the fish are subjected to the PVCR modulator and the odorant, thereby imprinting the fish. The anadromous fish are then transferred to seawater, where they can more easily distinguish the odorant. In the case of freshwater fish, for example, the fish can be maintained in freshwater, and the PVCR modulator and odorant can be introduced to the freshwater. Once the imprinting phase occurs, then the fish can be transferred back to freshwater without PVCR modulators added to it. In yet another example, marine fish, can be transferred from seawater directly to freshwater having the PVCR modulator and odorant added to it. Alternatively, since marine fish can also be grown in freshwater having PVCR modulators add to it, the present invention can be practiced by introducing an odorant to this PVCR environment, as described herein. Methods for growing marine fish in freshwater is described in detail in U.S. Pat. No. 6,463,882. After the marine fish are imprinted, they can then be transferred to seawater, or if desirable, back to freshwater having the PVCR modulator added to it (e.g., water without the odorant).

Once fish are imprinted, they can be transferred from the freshwater environment having the PVCR modulator and odorant, to a second body of water (e.g., seawater, freshwater or freshwater having a PVCR modulator). The present invention includes providing a source of the odorant after fish have been transferred. The source can be virtually any thing or composition that allows the fish to be exposed to the odorant. This odorant is the same odorant to which the fish have been imprinted. Examples, which are further described herein, include objects, compositions, suspensions, sprays, etc. When the fish are exposed to the odorant after being transferred, the fish can react to the odorant, as described herein.

In the case of anadromous fish, once fish are imprinted with the odorant and have undergone the smoltification process, the fish are ready to be transferred to seawater. When the fish are transferred to seawater, the fish are provided with feed that contains not only a source of nutrition, but also the same attractant or combination of attractants that were imprinted on the fish while the fish were in freshwater and exposed to the process described herein. The fish consume more feed and do so earlier after transfer to seawater, than do fish who are not exposed to the methods of the present invention. Accordingly, fish acclimate to seawater better and grow faster. In one embodiment, fish prefer feed having the attractant that was imprinted on them, as compared to feed having an attractant that was not imprinted on them.

Smoltification is the stage at which a fish undergoes the acclimation or adaptation from freshwater to seawater. Smoltification also refers to a process occurring in pre-adult anadromous fish that is physiological pre-adaption to seawater while still in freshwater. The smolification process varies from species to species. Different species of anadromous fish can undergo smoltification at different sizes, weights, and times in the life of the fish. The present invention induces the vast majority or all of the pre-adult anadromous fish to undergo this process and prepares them for transfer to seawater. Fish can be imprinted with an odorant, as described herein, during this stage.

In addition to imprinting during smoltification, the imprinting process can also occur during other stages of development of fish. Odorants can also be imprinted on fish larvae. An initial larval stage, referred to as a "yolk-sac" larval stage, is one during which the fish's primary source of food comes from the yolk-sac. During this stage, the larvae can be exposed to a PVCR modulator and an odorant so that the odorant can be imprinted. The PVCR modulator and odorant are added to the freshwater, as further described herein, for a sufficient period of time to cause the imprinting to occur. Another developmental stage during which imprinting can occur is in the "first feeding" larval stage. In this stage, the fish gradually cease using the yolk-sac as a source of nutrition and begin ingesting feed. The first feeding larvae can be exposed to a PVCR modulator and odorant for imprinting. As described herein, the odorant can be added to the freshwater or to the feed. The imprinting process can occur at one, or a combination of these stages, namely, the yolk-sac larval stage, first feeding larval stage, and smoltification stage using the same odorant. Performing the imprinting process during more than one of these stages creates a stronger response to certain odorants when the fish is exposed to it after transfer to seawater.

The present invention can also be applied to other types of fish, namely, flounder that migrate to coastal estuaries possessing diluted seawater concentrations where they spawn. The resulting larval and juvenile stages of flounders develop in these estuaries before returning to the sea. Imprinting of flatfish via restocking programs currently underway would provide for an environment where the methods of the present invention can occur, as further described herein.

The anadromous fish are maintained in freshwater prior to adding the PVCR modulator. The term, "freshwater," means water that comes from, for example, a stream, river, ponds, public water supply, or from other non-marine sources having, for example, the following ionic composition: less than about 2 mM of magnesium, calcium and NaCl. The term “freshwater” also refers to freshwater to which at least one PVCR modulator has been added, as described herein.

The PVCR modulator is added to the freshwater in sufficient amounts to modulate expression or alter the sensitivity of the PVCR. A PVCR has been isolated from various tissue of several types of anadromous fish using molecular biology techniques, as described in the Exemplification Section. DNA was isolated from samples from various species of anadromous fish including Atlantic Salmon, Char, Chum Salmon, Coho Salmon, King or Chinook Salmon, Pink Salmon, Sockeye Salmon and Trout.

The PVCR, which is located in various tissues (e.g., gill, skin, olfactory lamellae, olfactory epithelium, intestine, kidney, urinary bladder, G.I. tract, brain or muscle) of the anadromous fish, senses alterations in PVCR modulators including various ions (e.g., divalent cations), for example, in the surrounding water, in their serum or in the luminal contents of tubules inside the body, such as kidney, urinary bladder, or intestine. The PVCR located in the olfactory apparatus of fish plays an important role in sensing PVCR modulators and/or odorants, as described herein. Its ability to sense these modulators increases and/or decreases expression of the PVCR, thereby allowing the fish to better adapt to seawater. Increased and/or decreased expression of the PVCR can occur, for example, in one or more tissues, or in all tissues. When modulation of the PVCR occurs in the olfactory apparatus of the fish, the fish are able to sense the PVCR modulator or ordorant, and in conjunction with receptors, send a nerve impulse to brain. The presence of a PVCR modulator reversibly reduces the expression, sensitivity and/or responsiveness of the PVCR to an odorant, thereby reducing, minimizing, or abating the olfactory nerve impulse.

Molecular cloning of PVCR proteins demonstrates these ion receptor belong to a large superfamily of GTP-binding protein coupled receptors that include odorant and pheromone receptors. Localization of PVCR (CaR) expression in the nervous system of mammals demonstrates abundant expression of CaR mRNA in olfactory lobes.

Molecular cloning of mammalian and fish odorant receptors have demonstrated that PVCRs (in mammals the calcium receptor or CaR) are structurally related to both odorant and pheromone receptors (that bind a wide variety of odorant molecules) as well as metabotropic glutamate receptors (mGluRs) that bind glutamate. Both odorant and PVCRs are both G-protein coupled receptors that interact with G-proteins to activate signal transduction molecules including adenylate cyclase and/or phospholipase $A_2$ to increase intracellular $Ca^{2+}$ concentrations within cells.

A “PVCR modulator” is defined herein to mean a compound which modulates (e.g., increases and/or decreases) expression of the PVCR, or alters the sensitivity or responsiveness of the PVCR. Such compounds include, but are not limited to, PVCR agonists (e.g., inorganic polycations, organic polycations and amino acids), Type II calcimimetics, and compounds that indirectly alter PVCR expression (e.g., 1,25 dihydroxyvitamin D in concentrations of about 3,000–10,000 International Units/kg feed), cytokines such as Interleukin Beta, and Macrophage Chemotatic Peptide-1 (MCP-1)). Examples of Type II calcimimetics, which increase and/or decrease expression, and/or sensitivity of the PVCR, are, for example, NPS-R-467 and NPS-R-568 from NPS Pharmaceutical Inc., (Salt Lake, Utah, U.S. Pat. Nos. 5,962,314; 5,763,569; 5,858,684; 5,981,599; 6,001,884) which can be administered in concentrations of between about 0.1 $\mu$M and about 100 $\mu$M feed or water. See Nemeth, E. F. et al., *PNAS* 95: 4040–4045 (1998). Examples of inorganic polycations are divalent cations including calcium at a concentration between about 2.0 and about 10.0 mM and magnesium at a concentration between about 0.5 and about 10.0 mM; and trivalent cations including, but not limited to, gadolinium (Gd3+) at a concentration between about 1 and about 500 $\mu$M. Organic polycations include, but are not limited to, aminoglycosides such as neomycin or gentamicin in concentrations of between about 1 and about 8 gm/kg feed as well as organic polycations including polyamines (e.g., polyarginine, polylysine, polyhistidine, polyornithine, spermine, cadaverine, putrescine, copolymers of poly arginine/histidine, poly lysine/arginine in concentrations of between about 10 $\mu$M and 10 mM feed). See Brown, E. M. et al., *Endocrinology* 128: 3047–3054 (1991); Quinn, S. J. et al., *Am. J. Physiol.* 273: C1315-1323 (1997). Additionally, PVCR agonists include amino acids such as L-Tryptophan L-Tyrosine, L-Phenylalanine, L-Alanine, L-Serine, L-Arginine, L-Histidine, L-Leucine, L-Isoleucine, L-Aspartic acid, L-Glutamic acid, L-Glycine, L-Lysine, L-Methionine, L-Asparagine, L-Proline, L-Glutamine, L-Threonine, L-Valine, and L-Cysteine at concentrations of between about 1 and about 10 gm/kg feed. See Conigrave, A. D., et al., *PNAS* 97: 4814–4819 (2000). Amino acids, in one embodiment, are also defined as those amino acids that can be sensed by at least one PVCR in the presence of low levels of extracellular calcium (e.g., between about 1 mM and about 10 mM). In the presence of extracellular calcium, the PVCR in organs or tissues such as the intestine, pyloric caeca, or kidney can better sense amino acids. See Exemplification Section. The molar concentrations refer to free or ionized concentrations of the PVCR modulator in the freshwater, and do not include amounts of bound PVCR modulator (e.g., PVCR modulator bound to negatively charged particles including glass, proteins, or plastic surfaces). Any combination of these modulators can be added to the water or to the feed (in addition to the NaCl, as described herein), so long as the combination modulates expression and/or sensitivity of the PVCR.

The PVCR modulator can be administered to the fish in a number of ways. The invention encompasses administration of the PVCR in any way that is sufficient to modulate the expression and/or alter the sensitivity of the PVCR. In one embodiment, the PVCR modulator is simply added to the freshwater in various concentrations, as described herein. A freshwater environment having at least one PVCR modulator is referred to herein as a “PVCR modulator environment.” PVCR modulators (e.g., calcium and magnesium) that are added to the water modulate expression and/or alter the sensitivity of the PVCR on the skin and gills of the fish, and can be ingested by the fish, in particular, when fish are fed feed having between about 1% and about 10% NaCl (e.g., in concentrations between about 10,000 mg/kg and about 100,000 mg/kg feed). In addition to adding NaCl to the feed, the PVCR modulator (e.g., an amino acid such as tryptophan) can also be added to the feed. Amounts and types of PVCR modulators added to the feed are also described herein. Other embodiments include subjecting the fish to the PVCR modulator by “dipping” the fish in the modulator, e.g., organic polycations. The organic polycations can be formulated in such a way as to allow the polycations to adhere to the skin and gills of the fish, in sufficient amounts to modulate expression of the PVCR.

In one preferred embodiment, the present invention is practiced by adding a combination of two PVCR agonists to the freshwater. In particular, calcium and magnesium are added to the freshwater to bring the concentrations of each to between about 2.0 mM and about 10.0 mM of calcium, and between about 0.5 mM and about 10.0 mM of magnesium. In addition to adding calcium and magnesium to the water, these ranges of ion concentrations can be achieved by providing a brackish water (e.g., diluted seawater) environment for the fish.

Calcium and magnesium can come from a variety of sources, that when added to the water, the calcium and/or magnesium levels modulate expression of the PVCR, and/or are within the stated ranges. Sources of calcium and magnesium can be a mixture of a variety of compounds, or each can come from a substantially uniform or pure compound. Sources of calcium include, for example, $Ca(CO_3)_2$, $CaCl_2$, $CaSO_4$, and $Ca(OH)_2$ and sources of magnesium include, for example, $MgCl_2$, $MgSO_4$, $MgBr_2$, and $MgCO_3$.

In one embodiment, the invention includes intermittent (e.g., interrupted) as well as continuous (e.g., non-interrupted) exposure to freshwater having at least one PVCR modulator, while on the NaCl diet. Intermittent exposure to the PVCR can occur so long as the PVCR expression and/or altered sensitivity remains modulated (e.g., increased and/or decreased in various tissues).

The process of the present invention prepares fish for transfer from freshwater to seawater. The pre-adult anadromous fish are maintained in a freshwater environment having a PVCR modulator long enough to sufficient imprint the odorant on the fish. The fish are exposed to the odorant while in the PVCR modulator environment for a period of time sufficient to imprint the odorant and modulate the PVCR so that generation of nerve impulses in the olfactory apparatus occur. The length of time depends on the physiological and physical maturity of the fish. Some fish will more readily adapt to the environment, and modulate their expression and/or alter the sensitivity of their PVCR, while others will need more time to do so. Factors that can influence the length of time necessary to modulate the expression and/or alter sensitivity of the PVCR include, but are not limited to, size of the fish, level of PVCR expression or sensitivity, if any, prior to addition of the PVCR modulator to the freshwater, the fish's ability to excrete the PVCR modulator and ions, the fish's surface to volume ratio, etc. Therefore, the length of time the fish is maintained can range from about 7 days to several months (e.g., 7, 14, 21, 30, 45, 90 and 120 days), and preferably between about 2 weeks and about 6 weeks.

The invention further includes adding feed to the freshwater. The frequency and amounts of feed that fish are fed, are taught in the art. Generally, the fish are fed 1–3 times a day, totaling about 0.25–5.0% body weight/day. The feed has enough NaCl to contribute to a significant increased level of the PVCR modulator in the serum of the pre-adult anadromous fish. More specifically, NaCl has at least two effects. The first occurs when sufficient amounts of NaCl is present in the feed. The presence of NaCl in the feed causes the pre-adult anadromous fish to drink more water from the surrounding environment. Second, NaCl is a direct negative PVCR modulator, and works to decreases PVCR sensitivity. Despite NaCl's effect in decreasing sensitivity, it surprisingly increases PVCR expression in certain tissues when fish are fed a NaCl diet and the surrounding freshwater environment has at least one PVCR modulator it in. The increase in the ingestion of freshwater having PVCR modulators causes an overall increase of the serum levels of PVCR modulators.

The present invention also relates to a fish feed. In one embodiment, the feed has an agent that is sufficient to contribute to a significantly increased level of the PVCR modulator in serum of the anadromous fish. Such an agent can be used in the methods of the present invention described herein. One example of an agent that significantly increases the level of the PVCR modulator in the serum of fish is NaCl. Accordingly, in another embodiment, the feed contains between about 1%–10% of NaCl by weight, or between about 10,000 mg of NaCl/kg of feed and about 100,000 mg of NaCl/kg of feed (e.g., 12,000 mg/kg). The feed also includes an attractant, as described herein. These feeds can be referred to herein as "NaCl/attractant diets." The odorant is present in the feed in an amount sufficient to alter the olfactory sensing of fish (e.g., trace amounts to about 100 mg/kg). In addition to the NaCl and odorant, a PVCR modulator, and in particular a PVCR agonist such as an amino acid, can optionally be added. In one embodiment, the feed has between about 1% and about 10% NaCl by weight, an odorant such as L-alanine, and an amino acid such as tryptophan in an amount between about 1 and about 10 gm/kg. In addition to the unique components of the present invention that comprise the feed, as described above, the feed can additionally comprise ingredients that are traditionally included in feed, e.g., for nutrition and/or palatability. For example, the feed can include fish components, such as flounder or squid meat, or fish oils. Such feeds can also be designed for specific life stages of fish including larval, juvenile and adult fish.

The feed can be made in a number of ways, so long as the proper concentration of NaCl is present. The feed can be made, for example, by reformulating the feed, or by allowing the feed to absorb a solution having the NaCl and optionally, adding an odorant and/or PVCR modulator. A top dressing can be added for palatability.

Another embodiment of the present invention includes feeding anadromous fish feed having between 1% and 10% NaCl by weight and an odorant when the fish are maintained in a freshwater environment having between about 2.0 and about 10.0 mM of calcium, and between about 0.5 mM and about 10.0 mM of magnesium.

In another embodiment, the fish, while in the freshwater having the PVCR modulator, are also exposed to a photoperiod. A photoperiod refers to exposing the fish to light (e.g., sunlight, incandescent light or fluorescent light). Preferably, the photoperiod is substantially continuous, or occurs long enough to increase growth, induce smotification and/or reduce mortality. The fish can be exposed to a continuous photoperiod while they are in freshwater and undergoing the steps of the present invention (e.g., in the PVCR modulator environment and being fed the NaCl/attractant diet), as well as after being exposed to this environment and then transferred to seawater. The photoperiod can occur for at least about 12 hours within a 24 hour interval, or for longer periods such as about 14, 16, 18, 20, 22 or preferably, about 24 hours. The number of days the fish is exposed to a photoperiod can range from about 1 day to several months (e.g., 1, 3, 7, 14, 21, 30, 45, 90 and 120 days). Preferably, the photoperiod while the fish are being maintained in the PVCR modulator environment and being fed the NaCl/attractant diet, is preferably between about 4 days and about 50 days. After being transferred to seawater, the photoperiod exposure is preferably between about 7 days and about 45 days. Methods for exposing fish to a photoperiod are known in the art, and are described for example, in Willoughby, S., Manual of Salmonid Farming, Blackwell Scientific, Oxford, UK, at 106, and 152–154 (1999).

The fish can also be exposed to a photoperiod after transfer to seawater. The benefits of exposure to a photoperiod include a dramatic decrease in the mortality of fish after transfer to seawater. Thus, in one embodiment, maintaining fish in a continuous photoperiod increases their survival during their adaptation to seawater.

The term, "seawater," means water that comes from the sea, or water which has been formulated to simulate the chemical and mineral composition of water from the sea. The major elemental composition of the prepared seawater preferably falls substantially within the range of the major elemental composition of the natural seawater (e.g., having the following ionic composition: greater than 30 mM of magnesium, greater than about 6 mM of calcium, and greater than about 300 mM NaCl). Methods of preparing artificial seawater are known in the art and are described in, for instance, U.S. Pat. No. 5,351,651.

When performing the methods of the present invention on pre-adult anadromous fish, the fish exhibit significantly increased growth (e.g., SGR), gut motility and/or food consumption, as compared to pre-adult anadromous fish that are not subjected to the present invention. The present invention allows for enhancements in growth, gut motility and/or food consumption prior to, during, and after seawater transfer. Upon transfer to seawater, fish that are not subjected to the steps of the present invention generally experience osmotic stress, reduced or no food consumption, and even death. Osmotic stress results from differences in the osmotic pressure between the surrounding environment and body compartments of the fish. This disturbs the homeostatic equilibrium of the fish and results in decreased growth, reproductive failure and reduced resistance to disease. As a result of osmotic stress, the fish also grow more slowly and take longer to reach market size. Additionally, the present invention allows increases in growth of fish of a variety of sizes. Growth increases are expected to be seen in smaller fish (e.g., about 15 gm), medium fish (e.g., 40 gm) as well as larger fish (e.g., 90–120 gm). Accordingly, the present invention pertains to methods of increasing growth of pre-adult anadromous fish having weights that range from about 15 gm to about 120 gm. Expression and/or sensitivity of the PVCR can be modulated, for example, in the olfactory apparatus of the fish, and can be modulated in other types of tissues such as in chloride cells of gill tissue, epithelial cells in the gasterointestinal tract (e.g., stomach, pyloric caeca, proximal or distal intestine), tubules of the kidney, skin or urinary bladder.

Also, elimination of non-feeding or poorly feeding osmotically stressed fish in a group improves the overall feed conversion ratio of the entire group. Optimal feeding and growth after seawater transfer by all members of the group of treated fish will permit better feed utilization and improve the overall yield of production when fish reach market size.

The present invention includes methods to increase effective utilization of food and increasing the growth of anadromous fish by optimization of the function or increasing the growth of the gastrointestinal tract of fish by exposure of fish to a PVCR agonist including a single or mixture of L-amino acids that are included in either the food or freshwater during the smoltification process. These methods can be accomplished by addition of at least one PVCR modulator to the food that is added to freshwater, ingested by the fish and thereby exposes PVCRs present in cells that line the lumen of various gastrointestinal tract segments of larval or juvenile fish to alterations by the modulator. Modulation of gastrointestinal tract PVCRs in fish optimizes their utilization of ingested food via PVCR mediated sensing of specific amino acids and the signaling of the cells that line the gastrointestinal tract and transport both ions and nutrients across this epithelium.

Cells lining the fish G.I. tract contain abundant PVCR protein that is exposed to both the luminal contents of the stomach, pyloric cecae and intestine as well as the microenvironment located immediately next to the basolateral membranes of these cells. The present invention relates to the finding that PVCR proteins possess the ability to sense both ionic and amino acid concentrations and signal cells containing PVCRs to respond appropriately. By sensing the local concentration of amino acids, PVCR-containing cells can constantly discern the presence of nutrients (proteins) that are being digested by intestinal proteases into amino acids that are absorbed by these epithelial cells. Thus, the PVCR protein in the intestinal epithelial cell is performing a function similar to that described for olfactory epithelial cells above but the signal generated by PVCRs is not transmitted by nerve signals. Instead, activation of PVCRs in the GI tract produce activation of transport processes, alter GI motility as well as produce proliferation and growth of intestinal epithelial cells. These 2 functions of PVCR proteins provide for the sensing of GI tract necessary for efficient growth and development of fish. Methods of the present invention permit remodeling and development of the GI tract for optimal function in seawater while the fish remains in freshwater.

Accordingly, the present invention includes methods for improving the FCR for anadromous fish that are being transferred to seawater that have been imprinted with an odorant. The feed conversion ratio or FCR is obtained by dividing the body weight gained by a group of fish into the amount of food fed to these group of fish. The more efficient the conversion of food into body weight growth by fish, the smaller the FCR (small amount of food/large weight gain of fish). A very small FCR number (less than 1) encompasses a highly efficient conversion of food into body weight growth and is what the industry is striving for. By contrast, a large FCR means an inefficient conversion of food into body weight growth and is generally undesirable. A large or poor FCR is undesirable because feed usually is expensive and more can be used to grow fish to a given weight. The FCR values for fish subjected to the methods of the present invention are expected to be generally smaller and more desirable, than most industry published values because the present invention eliminates the presence of osmotically damaged fish that tend to increase the overall FCR since they eat food but do not grow. As a consequence, by subjecting the fish to the methods of the present invention, the FCR, in one embodiment, decreases to thereby allow for optimal feeding and growth of most all of the fish. The FCR of fish subjected to the present invention is sufficient to maintain growth and feeding of the majority of fish, or preferably increase the growth and feed consumption of the majority of fish. When fish are subjected to the methods of the present invention, they exhibit ranges of FCRs, for example, would include values between about 0.7 and about 7.0. In particular, food consumption or food intake is improved because the fish "smell" or "sense" the food with the PVCR and odorant receptors in cells of the olfactory lamellae or olfactory bulb.

Similarly, the present invention allows for decreasing or reducing the time between generations of pre-adult anadromous fish. These fish begin breeding earlier because the present invention increases their growth, as described herein. Since 2–3 years are required to obtain sexually mature fish, attempts to engage in selective breeding of traits requires this 2–3 year interval before a given trait can be selected for and the fish exhibit that trait breed. Improvements in growth and time to reach maturity produced by the invention reduce the time interval required to reach sexual maturity in fish by as much as about 6 months to about 12 months. Reducing the interval for breeding allows for the production of more fish, and the improved selection of fish that possess traits other than those that are better able to adapt to seawater (e.g., select for fish that have improved taste, increased filet thickness, increased α3 omega fatty acid content, or fish that are more readily able to modulate PVCR expression).

Prior to the present invention, anadromous fish that are transferred from freshwater to seawater are generally transferred at a particular size, referred to as "critical size." The critical size varies from species to species, but generally refers to a minimum size at which a fish can be transferred to seawater. The critical size for salmon, trout and char is between about 50 and about 100 gms, between about 70 and about 120 gms, and greater than 100 gms, respectively. Critical sizes for Coho, King, and Sockeye Salmon are between about 10 and about 15 gms, between about 20 and 40 gms and between about 1 and about 2 gms, respectively. Chum and Pink Salmon each have a critical size about less than 3 gms.

Prior to the invention, a population of pre-adult anadromous fish having attained a mean critical size were transferred to seawater. Some of the fish are physiologically ready for the transfer, while others are not. This is one of the reasons for the increased mortality rate upon transfer to seawater. The methods of the present invention physiologically prepares all or mostly all of the fish for transfer to seawater by modulating PVCR expression and/or sensitivity in the olfactory apparatus and in other tissues, and/or by inducing smoltification. In one embodiment, essentially all fish weighing more than about 15 grams can be transferred with no mortalities. Hence, the methods of the present invention include methods of preparing pre-adult anadromous fish for transfer to seawater, as well as inducing smotification in pre-adult anadromous fish.

Since the methods of the present invention modulate the expression and/or sensitivity of the PVCR in anadromous fish and are imprinted with an odorant, they survive better when transferred to seawater because the seawater feed has the same odorant with which the fish were imprinted and this allows them to feed better. The reduced osmotic stress results in reduced mortality. This occurs because the fish treated with the method experience no osmotic shock when transferred to seawater which has a very different ionic composition than freshwater. Hence, the present invention embodies methods of reducing the mortality rate after pre-adult anadromous fish are transferred to seawater.

Not only is the present invention useful in reducing mortality rates after transfer to seawater, the present invention is also used to increase survival rates in freshwater prior to transfer. Prior to the discovery of the present invention, a "smolt window" existed in which the hatcheries transferred the pre-adult anadromous fish to seawater, or else the fish died if they continued to remain in freshwater after undergoing smoltification. The PVCR modulator environment and the NaCl/attractant diet of the present invention allow the fish to continue to thrive indefinitely. The fish continue to consume feed and grow. Accordingly, the methods of the present invention significantly increase the time period or window in which the fish can be transferred to seawater, or eliminate it altogether. Additionally, after these fish are transferred to seawater they consume more feed, and grow better, as compared to fish that do not undergo the steps of the present invention.

The present invention also includes methods for transferring to seawater pre-adult anadromous fish having smaller weights, as compared to the industry recognized critical size for the particular species of fish. The methods of the present invention, as described herein, modulate PVCR expression in fish that are smaller than those normally transferred to seawater, or those undergoing or about to undergo smoltification. These methods include transferring a parr, the stage of a juvenile fish prior to becoming a smolt, to seawater. Parr is a life stage of pre-adult anadromous fish that occurs after maturation of alevins or yolk sac fry. Parr or fingerlings display characteristic ovid stripes or parr marks along their flanks, and normally undergo growth and development in freshwater prior to smoltification. The term "parr" is a term that is known in the art. As yolk sac fry continue to feed, they grow into larger parr. Parr can possess a wide range of body weights depending on conditions under which they are grown. The weights of parr vary from species to species. Body weights for parr vary significantly with a range from about 0.5 gms to about 70 gms. Carrying out the present invention in one experiment, as described herein, results in a transfer of Atlantic Salmon parr weighing as little as between about 13% and about 18.5% of the critical size weight (between about 70 and about 100 gms), or about 13 gms. Accordingly, the present invention encompasses method for preparing anadromous fish for transfer to seawater wherein the fish weigh between about 15 grams and about 120 grams at the time of seawater transfer.

The present invention additionally provides methods for transferring pre-adult anadromous fish into seawater having warmer temperatures (e.g., 14° C. and 19° C.), as compared to water temperatures (6°–14° C.) into which these fish have been transferred in the past. Since the fish experience reduced or little osmotic stress when transferred to seawater using the methods of the present invention, the fish are able to withstand transfer into higher water temperatures without exhibiting an increase in mortality rates.

The methods of the present invention also decrease the incidence of disease among the smolts and the growing salmon. Because smolts treated with the methods of the present invention experience less stress upon transfer to seawater, their immune functions are stronger, and they are less susceptible to parasitic, viral, bacterial and fungal diseases. Fish not treated with the methods described herein are more susceptible to such diseases, and can serve as reservoirs of disease, capable of infecting healthy fish.

Methods of Assessment of the PVCR and Odorant

The present invention includes methods of detecting the level of the PVCR to determine whether fish are ready for transfer from freshwater to seawater after they have been imprinted with an odorant. Methods that measure PVCR levels include several suitable assays. Suitable assays encompass immunological methods, such as FACS analysis, radioimmunoassay, flow cytometry, immunocytochemistry, enzyme-linked immunosorbent assays (ELISA) and chemiluminescence assays. Any method known now or developed later can be used for measuring PVCR expression.

Antibodies reactive with the PVCR or portions thereof can be used. In a preferred embodiment, the antibodies specifically bind with the PVCR or a portion thereof The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

In several of the preferred embodiments, immunological techniques detect PVCR levels by means of an anti-PVCR antibody (i.e., one or more antibodies). The term "anti-PVCR" antibody includes monoclonal and/or polyclonal antibodies, and mixtures thereof.

Anti-PVCR antibodies can be raised against appropriate immunogens, such as isolated and/or recombinant PVCR or portion thereof (including synthetic molecules, such as synthetic peptides). In one embodiment, antibodies are raised against an isolated and/or recombinant PVCR or portion thereof (e.g., a peptide) or against a host cell which expresses recombinant PVCR. In addition, cells expressing recombinant PVCR, such as transfected cells, can be used as immunogens or in a screen for antibody which binds receptor.

Any suitable technique can prepare the immunizing antigen and produce polyclonal or monoclonal antibodies. The art contains a variety of these methods (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce them. Researchers can use suitable assays such as ELISA to select antibody producing cells with the desired specificity.

Other suitable methods can produce or isolate antibodies of the requisite specificity. Examples of other methods include selecting recombinant antibody from a library or relying upon immunization of transgenic animals such as mice.

According to the method, an assay can determine the level of PVCR in a biological sample. In determining the amounts of PVCR, an assay includes combining the sample to be tested with an antibody having specificity for the PVCR, under conditions suitable for formation of a complex between antibody and the PVCR, and detecting or measuring (directly or indirectly) the formation of a complex. The sample can be obtained directly or indirectly, and can be prepared by a method suitable for the particular sample and assay format selected.

In particular, tissue samples, e.g., from nasal lamallae, olfactory apparatus, or gill, can be taken from fish after they are anaesthetized with MS-222. The tissue samples are fixed by immersion in 2% paraformaldehyde in appropriate Ringers solution corresponding to the osmolality of the fish, washed in Ringers, then frozen in an embedding compound, e.g., O.C.T.™ (Miles, Inc., Elkahart, Ind., USA) using methylbutane cooled with liquid nitrogen. After cutting 8–10 $\mu$ tissue sections with a cryostat, individual sections are subjected to various staining protocols. For example, sections are: 1) blocked with goat serum or serum obtained from the same species of fish, 2) incubated with rabbit anti-CaR or anti-PVCR antiserum, and 3) washed and incubated with peroxidase-conjugated affinity-purified goat antirabbit antiserum. The locations of the bound peroxidase-conjugated goat antirabbit antiserum are then visualized by development of a rose-colored aminoethylcarbazole reaction product. Individual sections are mounted, viewed and photographed by standard light microscopy techniques. The anti-CaR antiserum used to detect fish PVCR protein is raised in rabbits using a 23-mer peptide corresponding to amino acids numbers 214-236 localized in the extracellular domain of the RaKCaR protein. The sequence of the 23-mer peptide is: ADDDYGRPGIEKFREEAEERDIC (SEQ ID NO.: 9) A small peptide with the sequence DDYGRPGIEKFREEAEERDICI (SEQ ID NO.: 10) or ARSRNSADGRSGDDLPC (SEQ ID NO.: 11) can also be used to make antisera containing antibodies to PVCRs. Such antibodies can be monoclonal, polyclonal or chimeric.

Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels and the like. The detection of antibodies in a complex can also be done immunologically with a second antibody which is then detected (e.g., by means of a label). Conventional methods or other suitable methods can directly or indirectly label an antibody.

In performing the method, the levels of PVCR in various tissues change in comparison to control. Modulated levels or the presence of PVCR expression in various tissues, as compared to a control, indicate that the fish or the population of fish from which a statistically significant amount of fish were tested, are ready for transfer to freshwater. A control refers to a level of PVCR, if any, from a fish that is not subjected to the steps of the present invention.

The PVCRs can also be assayed by Northern blot analysis of mRNA from tissue samples. Northern blot analysis from various shark tissues has revealed that the highest degree of PVCRs expression is in gill tissue, followed by the kidney and the rectal gland. There appear to be at least three distinct mRNA species of about 7 kb, 4.2 kb and 2.6 kb.

The PVCRs can also be assayed by hybridization, e.g., by hybridizing one of the PVCR sequences provided herein or an oligonucleotide derived from one of the sequences, to a DNA-containing tissue sample from a fish. Such a hybridization sequence can have a detectable label, e.g., radioactive, fluorescent, etc., attached to allow the detection of hybridization product. Methods for hybridization are well known, and such methods are provided in U.S. Pat. No. 5,837,490, by Jacobs et al., the entire teachings of which are herein incorporated by reference in their entirety. The design of the oligonucleotide probe should preferably follow these parameters: (a) it should be designed to an area of the sequence which has the fewest ambiguous bases ("N's"), if any, and (b) it should be designed to have a $T_m$ of approx. 80° C. (assuming 2° C. for each A or T and 4 degrees for each G or C).

Stringency conditions for hybridization refers to conditions of temperature and buffer composition which permit hybridization of a first nucleic acid sequence to a second nucleic acid sequence, wherein the conditions determine the degree of identity between those sequences which hybridize to each other. Therefore, "high stringency conditions" are those conditions wherein only nucleic acid sequences which are very similar to each other will hybridize. The sequences can be less similar to each other if they hybridize under moderate stringency conditions. Still less similarity is needed for two sequences to hybridize under low stringency conditions. By varying the hybridization conditions from a stringency level at which no hybridization occurs, to a level at which hybridization is first observed, conditions can be determined at which a given sequence will hybridize to those sequences that are most similar to it. The precise conditions determining the stringency of a particular hybridization include not only the ionic strength, temperature, and the concentration of destabilizing agents such as formamide, but also on factors such as the length of the nucleic acid sequences, their base composition, the percent of mismatched base pairs between the two sequences, and the frequency of occurrence of subsets of the sequences (e.g., small stretches of repeats) within other non-identical sequences. Washing is the step in which conditions are set so as to determine a minimum level of similarity between the sequences hybridizing with each other. Generally, from the lowest temperature at which only homologous hybridization occurs, a 1% mismatch between two sequences results in a 1° C. decrease in the melting temperature ($T_m$) for any chosen SSC concentration. Generally, a doubling of the concentration of SSC results in an increase in the $T_m$ of about 17° C. Using these guidelines, the washing temperature can be determined empirically, depending on the level of mismatch sought. Hybridization and wash conditions are explained in *Current Protocols in Molecular Biology* (Ausubel, F. M. et al., eds., John Wiley & Sons, Inc., 1995, with supplemental updates) on pages 2.10.1 to 2.10.16, and 6.3.1 to 6.3.6.

High stringency conditions can employ hybridization at either (1) 1×SSC (10×SSC=3 M NaCl, 0.3 M $Na_3$-citrate-$2H_2O$ (88 g/liter), pH to 7.0 with 1 M HCl), 1% SDS (sodium dodecyl sulfate), 0.1–2 mg/ml denatured calf thymus DNA at 65° C., (2) 1×SSC, 50% formamide, 1% SDS, 0.1–2 mg/ml denatured calf thymus DNA at 42° C., (3) 1% bovine serum albumin (fraction V), 1 mM $Na_2$.EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 μg/ml denatured calf thymus DNA at 65° C., or (6) 5×SSC, 5× Denhardt's solution, 50% fornamide, 1% SDS, 100 μg/ml denatured calf thymus DNA at 42° C., with high stringency washes of either (1) 0.3–0.1×SSC, 0.1% SDS at 65° C., or (2) 1 mM $Na_2EDTA$, 40 mM $NaHPO_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6 ($log_{10}$M)+0.41(% G+C)−0.61 (% formamide)−500/L), where "M" is the molarity of monovalent cations (e.g., $Na^+$), and "L" is the length of the hybrid in base pairs.

Moderate stringency conditions can employ hybridization at either (1) 4×SSC, (10×SSC=3 M NaCl, 0.3 M $Na_3$-citrate.$2H_2O$ (88 g/liter), pH to 7.0 with 1 M HCl), 1% SDS (sodium dodecyl sulfate), 0.1–2 mg/ml denatured calf thymus DNA at 65° C., (2) 4×SSC, 50% formamide, 1% SDS, 0.1–2 mg/ml denatured calf thymus DNA at 42° C., (3) 1% bovine serum albumin (fraction V), 1 mM $Na_2$.EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1–2 mg/ml denatured calf thymus DNA at 65° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 42° C., (5) 5×SSC, 5× Denhardt's solution, 1% SDS, 100 μg/ml denatured calf thymus DNA at 65° C., or (6) 5×SSC, 5× Denhardt's solution, 50% formamide, 1% SDS, 100 μg/ml denatured calf thymus DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6($log_{10}$M)+0.41(% G+C)−0.61 (% formamide)−500/L), where "M" is the molarity of monovalent cations (e.g., $Na^+$), and "L" is the length of the hybrid in base pairs.

Low stringency conditions can employ hybridization at either (1) 4×SSC, (10×SSC=3 M NaCl, 0.3 M $Na_3$-citrate.$2H_2O$ (88 g/liter), pH to 7.0 with 1 M HCl), 1% SDS (sodium dodecyl sulfate), 0.1–2 mg/ml denatured calf thymus DNA at 50° C., (2) 6×SSC, 50% formamide, 1% SDS, 0.1–2 mg/ml denatured calf thymus DNA at 40° C., (3) 1% bovine serum albumin (fraction V), 1 mM $Na_2$.EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1–2 mg/ml denatured calf thymus DNA at 50° C., (4) 50% formamide, 5×SSC, 0.02 M Tris-HCl (pH 7.6), 1× Denhardt's solution (100×=10 g Ficoll 400, 10 g polyvinylpyrrolidone, 10 g bovine serum albumin (fraction V), water to 500 ml), 10% dextran sulfate, 1% SDS, 0.1–2 mg/ml denatured calf thymus DNA at 40° C., (5) 5×SSC, 5× Denhardt's solution, 1% SDS, 100 μg/ml denatured calf thymus DNA at 50° C., or (6) 5×SSC, 5× Denhardt's solution, 50% formamide, 1% SDS, 100 μg/ml denatured calf thymus DNA at 40° C., with low stringency washes of either 2×SSC, 0.1% SDS at 50° C., or (2) 0.5% bovine serum albumin (fraction V), 1 mM $Na_2EDTA$, 40 mM $NaHPO_4$ (pH 7.2), 5% SDS. The above conditions are intended to be used for DNA—DNA hybrids of 50 base pairs or longer. Where the hybrid is believed to be less than 18 base pairs in length, the hybridization and wash temperatures should be 5–10° C. below that of the calculated $T_m$ of the hybrid, where $T_m$ in ° C.=(2×the number of A and T bases)+(4×the number of G and C bases). For hybrids believed to be about 18 to about 49 base pairs in length, the $T_m$ in ° C.=(81.5° C.+16.6($log_{10}$M)+0.41(% G+C)−0.61 (% formamide)−500/L), where "M" is the molarity of monovalent cations (e.g., $Na^+$), and "L" is the length of the hybrid in base pairs.

The present invention encompasses detection of PVCRs with PCR methods using primers disclosed or derived from sequences described herein. For example, PVCRs can be detected by PCR using the following primers:5'-TGT CKT GGA CGG AGC CCT TYG GRA TCG C-3' (SEQ ID NO: 12) and 5'-GGC KGG RAT GAA RGA KAT CCA RAC RAT GAA G-3' (SEQ ID NO: 13), where K is T or G, Y is C or T, and R is A or G. PCR is the selective amplification of a target sequence by repeated rounds of nucleic acid replication utilizing sequence-specific primers and a thermostable polymerase. PCR allows recovery of entire sequences between two ends of known sequence. Methods of PCR are described herein and are known in the art.

In particular, the level of aquatic PVCR can be determined in various tissues by Reverse Transcriptase-Polymerase Chain Reaction (RT-PCR) after isolation of poly A+ RNA from aquatic species. Methods of PCR and RT-PCR are well characterized in the art (See generally, PCR Technology: Principles and Applications for DNA Amplification (ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res., 19:4967 (1991); Eckert et al., PCR Methods and Applications, 1:17 (1991); PCR (eds. McPherson et al., IRL Press, Oxford); Ausebel, F. M. et al., Current Protocols in Molecular Biology, Greene Publishing Assoc. and Wiley-Interscience 1987, & Supp. 49, 2000; and U.S. Pat. No. 4,683,202). Briefly, mRNA is extracted from the tissue of interest and reverse transcribed. Subsequently, a PCR reaction is performed with PVCR-specific primers and the presence of the predicted PVCR product is determined, for example, by agarose gel electrophoresis. Examples of PVCR-specific primers are SEQ ID NO.: 12 and/or SEQ ID NO.: 13. The product of the RT-PCR reaction that is performed with PVCR-specific primers is referred to herein as a RT-PCR product. The RT-PCR product can include nucleic acid molecules having part or all of the PVCR sequence. The RT-PCR product can optionally be radioactively labeled and the presence or amount of PVCR product can be determined using autoradiography. Two examples of commercially available fluorescent probes that can be used in such an assay are Molecular Beacons (Stratagene) and Taqman® (Applied Biosystems). Alternative methods of labeling and quantifying the RT-PCR product are well known to one of skill in the art (see Ausebel, F. M. et al., Current Protocols in Molecular Biology, Greene Publishing Assoc. and Wiley-Interscience 1987, & Supp. 49, 2000. Poly A+ RNA can be isolated from any tissue which contains at least one PVCR by standard methods. Such tissues include, for example, gill, nasal lamellae, urinary bladder, kidney, intestine, stomach, liver and brain.

Hence, the present invention includes kits for the detection of the PVCR in the olfactory apparatus or the quantification of the PVCR in the olfactory apparatus having either antibodies specific for the PVCR or a portion thereof, or a nucleic acid sequence that can hybridize to the nucleic acid of the PVCR.

Alterations in the expression or sensitivity of PVCRs could also be accomplished by introduction of a suitable transgene. Suitable transgenes would include either the PVCR gene itself or modifier genes that would directly or indirectly influence PVCR gene expression in response to a PVCR modulator and/or odorant. Methods for successful introduction, selection and expression of the transgene in fish oocytes, embryos and adults are described in Chen, T T et al., Transgenic Fish, *Trends in Biotechnology* 8:209–215 (1990).

The present invention provides methods for identifying and/or quantifying the effects of PVCR modulators on olfactory receptor sensing and visa versa. The present invention also includes methods for determining whether a compound is an odorant. When fish are exposed to an odorant (e.g., the odorant binds to olfactory lamellae), the odorant binds to the olfactory epithelium of the fish, which leads to the generation of a nerve impulse. The electric potential of the impulse can be measured using methods known in the art, or those later developed. One example of a method that can be used to measure electric potential is an electroencephalogram, commonly referred to as an EEG. Example 3 describes in detail how to measure nerve impulse of fish, and in particular, as it relates to modulation of the PVCR in the olfactory apparatus of the fish. Briefly, the fish are anaesthetized and placed in V-clamp apparatus where its gills were irrigated continuously with aerated seawater and its nasal lamellae bathed continuously by a stream of distilled water via a tube held in position in the inhalant olfactory opening. The olfactory nerves of the fish were exposed by removal of overlying bony structures. Odorants to be tested can be delivered as boluses to the olfactory epithelium via a 3 way valve where 1 cc of water containing the stimulus was rapidly injected into the tube containing a continuously stream of distilled water. The electrical potentials are obtained using, for example, high resistance tungsten electrodes and can be recorded (Grass Amplifier Apparatus), digitized, displayed. The results can be analyzed by computer using compatible software. The presence of an electrical impulse indicates that the compound being tested is an odorant, and the absence of an electrical impulse indicates the absence of an odorant.

Scientific assays exist which determine whether a compound is a fish odorant. Examples of such tests are behavioral avoidance assays (e.g., to test if a compound is a repellant) and behavioral attractant assays (e.g., to test if a compound is an attractant). Methods for performing such behavioral assays are known in the art and are described, for example, in Royce-Malmgren et al., *J. Chemical ecology,* 13(3) 533, 546 (1987). Briefly, fish are placed in a maze along with the compound being tested. The fish have the option of swimming toward the compound being tested or swimming away from the compound being tested. If more fish swim toward the compound a statically significant number of times, as compared to a control, then the odorant is determined to be an attractant. Similarly, if more fish swim away from the odorant a statistically significant number of times, as compared to a control, then the odorant is determined to be a repellant. Assays that are later developed for determining whether a compound is a fish attractant or fish repellant can also be used.

Methods of Homing Fish and Repelling Fish

After being imprinted, the invention also embodies exposing the fish, after transfer to seawater, to the odorant. In addition to introducing the odorant by putting it in the feed, the odorant can be placed into the seawater, or adhered to an object that is placed into the seawater in the vicinity of the fish. Accordingly, the present invention pertains to methods of homing or luring fish by imprinting the fish to an attractant, as described herein, and after transferring the fish to seawater, placing the attractant used during the imprinting process on an object. "Homing or luring fish" refers to fish that are attracted to a particular odorant. Examples of such objects are netting or fishing lures. Accordingly, the present invention include methods for homing a fish using attractants that are adhered to netting or fishing lure, as well as the objects having the attractant that was used during the imprinting process. Fisherman or fish hatcheries can benefit from attracting fish for the purpose of catching them or breeding them. In particular, such attractants could be used for a wide variety of applications including methods for salmon homing which include improving the efficiency of ocean ranching of various species of anadromous fish such as salmon, novel species-specific baits for sports fishing, as well as methods to increase yields of commercial hook or net fishing or reduce the capture of valuable but undesired species (by-catch).

The imprinting of freshwater fish with an attractant for use in freshwater can be performed by exposure of the fish to the attractant in freshwater. The most important element of this task is identification of the appropriate odorant that is optimal for freshwater use. As shown in the examples provided, the olfactory nerve signal for certain odorants is diminished or ablated after simultaneous stimulation of an olfactory PVCR. Thus, methods of the present invention would be used to identify ideal freshwater odorants.

The present invention relates to methods for repelling fish in seawater. After being imprinted by the methods described herein, the fish have increased sensitivity to the repellant or combination of repellants used during the imprinting process. Consequently, the fish are sensitized to the repellant used during the imprinting process and are more likely to swim away from the repellant, as compared to repellants that were not imprinted on the fish. The fish are simply exposed to the repellant in any number of ways including placing the repellant used in the imprinting process into the seawater (e.g., by spraying, streaming or otherwise releasing the repellant into the seawater) or by placing the repellant on an object. One example of this method is applying the fish repellant to an object nearby or on an intake to a turbine, a condition that would otherwise pose a hazzard to the fish. Without the repellant, fish swim near the intake and get injured. The methods of repelling the fish, as described herein, allow fish to avoid such dangerous areas. Another example is to coat a barrier netting of ocean netpens that normally contain anadromous fish with a repellant. Coating the barrier netting would deter the escape of enclosed fish since they would avoid the netting due to its repellant content or surroundings.

Another example repelling fish using the methods described herein is for swimmers, surfers, divers, etc. to repel dangerous fish such as sharks. The repellant can consist of a PVCR antagonist that would antagonize or blunt the normal sensing of seawater by at least one PVCR in the olfactory apparatus thereby mimicking the stimulus that fish receive when they encounter freshwater. Since many marine species such as sharks that are restricted to seawater and avoid freshwater environments, the object or person coated with or surrounded by a PVCR antagonist would be avoided by the fish as he/she would be perceived by the fish as surrounded by freshwater.

In particular, the attractants or repellants adhered to these objects (e.g., netting or fishing lure) are those that comprise a PVCR modulator in an amount sufficient to modulate the PVCR in the olfactory sensing apparatus of the fish. The attractant or repellant can be adhered to the object, coated on the surface, impregnated within the object (e.g., rope or netting), or attached in any way to the object so long as the odorant is present in sufficient quantities to allow for the homing or repelling of fish by altering the PVCR in the olfactory sensing apparatus of the fish, as further described herein. The odorant can also be released directly into the seawater. The amount of the odorant will depend on a variety of factors, such as the method for attaching the odorant to the object (e.g., one may need more odorant if the odorant is impregnated into a netting or rope, as compared to simply adhering to the outside of an object), the distance of the fish from the object (e.g., you will need more odorant to attract or repel fish that are farther away), the desired effect of the odorant on the fish (e.g., a stronger odorant response will require more odorant than if one wanted to elicit a weaker response), characteristics of the fish (e.g., weight, size, type of anadromous fish), and the amounts of PVCR modulators that are present in the seawater (e.g., certain PVCR modulators will reduce the response to the odorant, as further described herein). In one experiment, the presence of certain amino acids, which can be odorants, either alone or in combination increase the sensitivity to calcium permitting PVCR to "sense" amino acids in the presence of physiological concentrations of calcium.

The present invention is further and more specifically illustrated by the following Examples, which are not intended to be limiting in any way.

Exemplification

The following examples refer to Process I and Process II throughout. Process I is also referred to herein as "SUPERSMOLT™ I Process." A "Process I" fish or smolt refers to a fish or smolt that has undergone the steps of Process I. A Process I smolt is also referred to as a "SUPERSMOLT™ I" smolt. Likewise, Process II is also referred to herein as "SUPERSMOLT™ II Process." A "Process H" fish or smolt refers to a fish or smolt that has undergone the steps of Process II. A Process II smolt is also referred to as a "SUPERSMOLT™ II" smolt.

Process I: Fish including, pre-adult anadromous fish (this includes both commercially produced S0, S1 or S2 smolts as well as smaller parr/smolt fish), are exposed to or maintained in freshwater containing either 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl. See Example 2 for further details regarding the feed. Fish are exposed to or maintained in this regimen of water mixture and feed for a total of 30–45 days, using standard hatchery care techniques. Water temperatures vary between 10–16° C. Fish are exposed to a constant photoperiod for the duration of Process I. A fluorescent light is used for the photoperiod.

Process II: Fish, including pre-adult anadromous fish (this includes both commercially produced S0, S1 or S2 smolts as well as smaller parr/smolt fish), are exposed to or maintained in freshwater containing 2.0–10.0 mM Calcium and 0.5–10.0 mM Magnesium ions. This water is prepared by addition of calcium carbonate and/or chloride and magnesium chloride to the freshwater. Fish are fed with feed pellets containing 7% (weight/weight) NaCl and either 2 gm or 4 gm of L-Tryptophan per kg of feed. See Example 2 for further details regarding the feed. Fish are exposed to or maintained in this regimen of water mixture and feed for a total of 30–45 days using standard hatchery care techniques. Water temperatures vary between 10–16° C. Fish are exposed to a constant photoperiod for the duration of Process II. A fluorescent light is used for the photoperiod.

EXAMPLE 1

Polyvalent Cation-Sensing Receptors (PVCRs) Serve as Salinity Sensors in Fish Polyvalent cation-sensing receptors (PVCRs) serve as salinity sensors in fish. These receptors are localized to the apical membranes of various cells within the fish's body (e.g., in the gills, intestine, kidney) that are known to be responsible for osmoregulation. A full-length cation receptor (CaR, also referred to as "PVCR") from the dogfish shark has been expressed in human HEK cells. This receptor was shown to respond to alterations in ionic compositions of NaCl, Ca2+ and Mg2+ in extracellular fluid bathing the HEK cells. The ionic concentrations responded to by this PVCR encompassed the range which includes the transition from freshwater to seawater. Expression of PVCR mRNA is also increased in fish after their transfer from freshwater to seawater, and is modulated by PVCR agonists. Partial genomic clones of PVCRs have also been isolated from other fish species, including winter and summer flounder as well as lumpfish, by using nucleic acid amplification with degenerate primers.

This method was also used to isolate partial genomic clones of PVCRs for Atlantic salmon (FIG. 1), arctic char (FIG. 2) and rainbow trout (FIG. 3). The degenerate oligonucleotide primers used were 5'-TGT CKT GGA CGG AGC CCT TYG GRA TCG C-3' (SEQ ID NO:12) and 5'-GGC KGG RAT GAA RGA KAT CCA RAC RAT GAA G-3' (SEQ ID NO:13), where K is T or G, Y is C or T, and R is A or G. The degenerate oligos were generated by standard methodologies (Preston, G. M., 1993, "Polymerase chain reaction with degenerate oligonucleotide primers to clone gene family members," in: Methods in Mol. Biol., vol. 58, ed. A. Harwood, Humana Press, pp. 303–312). Genomic bands from these three species were amplified, purified by agarose gel electrophoresis, ligated into an appropriate plasmid vector (salmon and arctic char species-pT7 Blue (Novagen, Madison, Wis.; trout used pGem-T (Promega Biotech. Madison, Wis.), and transformed into an appropriate bacterial host strain salmon and arctic char-pT7 vector with NovaBlue (Novagen, Madison, Wis.) and trout pGEM-T used JM-109 *E. coli* cell which was then grown in liquid medium. The plasmids and inserts were purified from the host cells, and sequenced. FIG. 4 shows the deduced amino acid sequences and alignment for the PVCRs from Atlantic salmon, arctic char and rainbow trout, relative to the PVCR from the kidney of the dogfish shark (*Squalus acanthias*). The SKCaR amino acid and nucleic acid sequences are shown in FIGS. 4A–H.

Additional PVCR sequences have been isolated and sequences in other species of fish. These sequences include, but are not limited to, PVCRs isolated in salmon (e.g, Coho Salmon (*Oncorhynchus kisutch*), Chum Salmon (*Oncorhynchus keta*), Chinook Salmon (*Oncorhynchus tshawytscha*), Pink Salmon (*Oncorhynchus gorbuscha*), Sockeye Salmon (*Oncorhynchus nerka*)). The sequences for these species can be found in patent application Ser. No. 09/687,477, filed on Oct. 12, 2000.

EXAMPLE 2

The Feed

There are two general methods to prepare feed for consumption by fish as part of Process I and II. These two processes involve either reformulation of feed or addition of a concentrated solution for absorption by the feed followed by a top dressing for palatability. This disclosure describes the methodology to prepare feed using each of these 2 methods.

Methods

Feed Manufacture for Salmon Experiments

To reformulate feed, the ingredients are as follows: Base Diet was made using the following ingredients and procedure: 30% Squid (liquefied in blender), 70% Corey Aquafeeds flounder diet (powderized in blender). Ingredients were blended into a semi moist "dough" ball. Other ingredients including NaCl or PVCR active compounds were blended into the base diet by weight according to what the experiment called for.

Moore Clark standard freshwater salmonid diet (sizes 1.2,1.5.2.0, 2.5, and 3.5 mm) can also be used. A top dressing was applied to the pellets such that top dressing is composed of 4% of the weight of the Base Diet. Top dressing is composed of 50% krill hydrolysate (Specialty Marine Products Ltd.) and 50% Menhaden fish oil. The top dressing is added for palatability and sealing of added ingredients.

Other ingredients can include NaCl, MgCl2, CaCl2 or L-Tryptophan that are added by weight to the base diet by weight.

Preparation of Feed Containing 7% (Weight/Weight) NaCl

For the Process I: Solid sodium chloride or NaCl apportioned at a ratio of 7% of the weight of the Moore Clark standard freshwater salmonid diet weight was added to a volume of tap water approximately 3–4 times the weight of NaCl. The mixture was heated to 60–70° C. with mixing via use of a magnetic stirring bar to dissolve salt. The NaCl solution was then poured into a hand held sprayer and applied to the Moore Clark standard freshwater salmonid diet that is tumbling inside of a 1.5 cubic meter motorized cement mixer. After absorption of the NaCl rich solution, the wetted Moore Clark standard freshwater salmonid diet is spread out thinly on window screening and placed in an enclosed rack system equipped with a fan and 1500 watt heater to expedite drying process. After drying for approximately 6 hr, the dried NaCl-rich pellets are returned to the cement mixer and a top dressing is applied. The feed is stored at room temperature until use.

Preparation of Feed Containing 7% (weight/weight) NaCl+PVCR Agonist (Tryptophan) For the Process II: Solid sodium chloride or NaCl apportioned at a ratio of 7% of the weight of the Moore Clark standard freshwater salmonid diet weight was added to a volume of tap water approximately 3–4 times the weight of NaCl. The mixture was heated to 60–70° C. with mixing via use of a magnetic stirring bar to dissolve salt. USP Grade L-Tryptophan was added to the water at either 2 grams or 4 grams for every kg of Moore Clark standard freshwater salmonid diet depending on formulation need. Dilute hydrochloric acid was added to the water with mixing until the tryptophan was dissolved and the pH of solution was approximately 4.0. The NaCl+Tryptophan solution was then poured into a hand held sprayer and was then applied to the Moore Clark standard freshwater salmonid diet tumbling inside a cement mixer. After absorption of the NaCl+Tryptophan solution, the wetted Moore Clark standard freshwater salmonid diet is then spread out thinly on window screening and placed in an enclosed rack system equipped with a fan and 1500-watt heater to expedite drying process. After drying for approximately 6 hr, the dried NaCl/Tryptophan-rich pellets are then returned to the cement mixer and a top dressing is applied. The feed is stored at room temperature until use. L-Tryptophan can be replaced with any amino acid, described herein, that modulates PVCR expression.

To make the feed for freshwater for use during the imprinting process that contains the odorant, the steps for making the feed for either Process I or II, as described above, can be followed, and the odorant is simply added to the feed. The amount of odorant added to the feed is between trace amounts to about 100 mg/kg (mg of odorant per kg of feed). The odorant used for the feed can be identified by the methods described herein.

Feed for seawater containing the odorant can be made, for example, by adding the odorant used during the imprinting process to feed typically provided to fish transferred to seawater.

EXAMPLE 3

Presence and Function of PVCR Protein in Nasal Lamellae and Olfactory Bulb as Well as GI Tract of Fish The data described herein illustrates the roles of PVCR proteins in the olfactory organs (nasal lamellae and olfactory bulb) of fish as it relates to the ability of fish to sense or "smell" both alterations in the water salinity and/or ionic composition as well as specific amino acids. These data are particularly applicable to anadromous fish (salmon, trout and char) that are either transferred from freshwater directly to seawater or exposed to Process I or Process II in freshwater and then transferred to seawater.

These data described herein were derived from a combination of sources including immunocytochemistry using anti-PVCR antisera, RT-PCR amplification of PVCRs from nasal lamellae tissue, studies of the function of recombinant aquatic PVCR proteins expressed in cultured cells where these proteins "sense" specific ions or amino acids as well as electrophysiological recordings of nerve cell electrical activity from olfactory nerves or bulb of freshwater salmon.

The combination of immunocytochemistry and RT-PCR data, described herein, reveal the presence of PVCR proteins in both major families of fish (elasmobranch-shark; teleost-salmon) in both larval, juvenile and adult life stages. Immunocytochemistry analyses reveal that one or more PVCR proteins are present both on portions of olfactory receptor cells located in the nasal lamellae of fish (where they are bathed in water from the surrounding environment) as well as on nerve cells that compose olfactory glomeruli present in the olfactory bulb of fish brain (where these cells are exposed to the interval ionic environment of the fish's body). Thus, from these locations fish are able to compare the ionic composition of the surrounding water with reference to their own internal ionic composition. Alterations in the expression and/or sensitivity of PVCR proteins provides the means to enable fish to determine on a continuous basis whether the water composition they encounter is different from that they have been adapted to or exposed to previously. This system is likely to be integral to both the control of internal body composition of fish as well as the homing of salmon from freshwater to seawater and visa versa. Thus, fish have the ability to "smell" changes in water salinity directly via PVCR proteins and respond appropriately to both regulate their body composition and remain in environments that are best for their survival in nature.

One feature of this biological system is alteration in the sensitivity of the PVCR protein for divalent cations such as $Ca^{2+}$ and $Mg^{2+}$ by changes in the NaCl concentration of the water. Thus, PVCRs in fish olfactory organs have different apparent sensitivity to $Ca^{2+}$ in either the presence or absence of NaCl. These data presented here are the first direct evidence for these functions via PVCR proteins present in the olfactory apparatus of fish.

Another feature of PVCR protein function in the olfactory apparatus of fish is to modulate responses of olfactory cells to specific odorants (attractants or repellants). Transduction of cellular signals resulting from the binding of specific odorants to olfactory cells occurs via changes in standing ionic gradients across the plasma membranes of these cells. The binding of specific odorants to olfactory cells results in electrical nerve conduction signals that can be recorded using standardize electrophysiological electrodes and equipment. Using this apparatus, the olfactory apparatus of freshwater adapted salmon:

1. responded to PVCR agonists in a concentration-dependent manner similar to that shown previously for other fish tissues including that shown for winter flounder urinary bladder. These data provide the functional evidence of the presence of a PVCR protein; and
2. that the presence of a PVCR agonist reduces or ablates the signal resulting from odorants including both attractants or repellants. Thus, PVCRs in the olfactory apparatus of salmon possess the capacity of modulating responses to various odorants.

Another feature of PVCR proteins is their ability to "sense" specific amino acids present in surrounding environment. Using the full-length recombinant SKCaR cDNA, functional SKCaR protein was expressed in HEK cells and shown to respond in a concentration-dependent manner to both single and mixtures of L-amino acids. Since PVCR agonists including amino acids as well as polyamines (putrescine, spermine and spermidine) are attractants to marine organisms including fish and crustaceans, these data provide for another means by which PVCR proteins would serve not only as modulators of olfaction in fish but also as sensors of amino acids and polyamines themselves. PVCR proteins in other organs of fish including G.I. tract and endocrine organs of fish also function to sense specific concentrations of amino acids providing for integration of a wide variety of cellular processes in epithelial cells (amino acid transport, growth, ion transport, motility and growth) with digestion and utilization of nutrients in fish.

Description of Experimental Results and Data Interpretation

Figure 5:
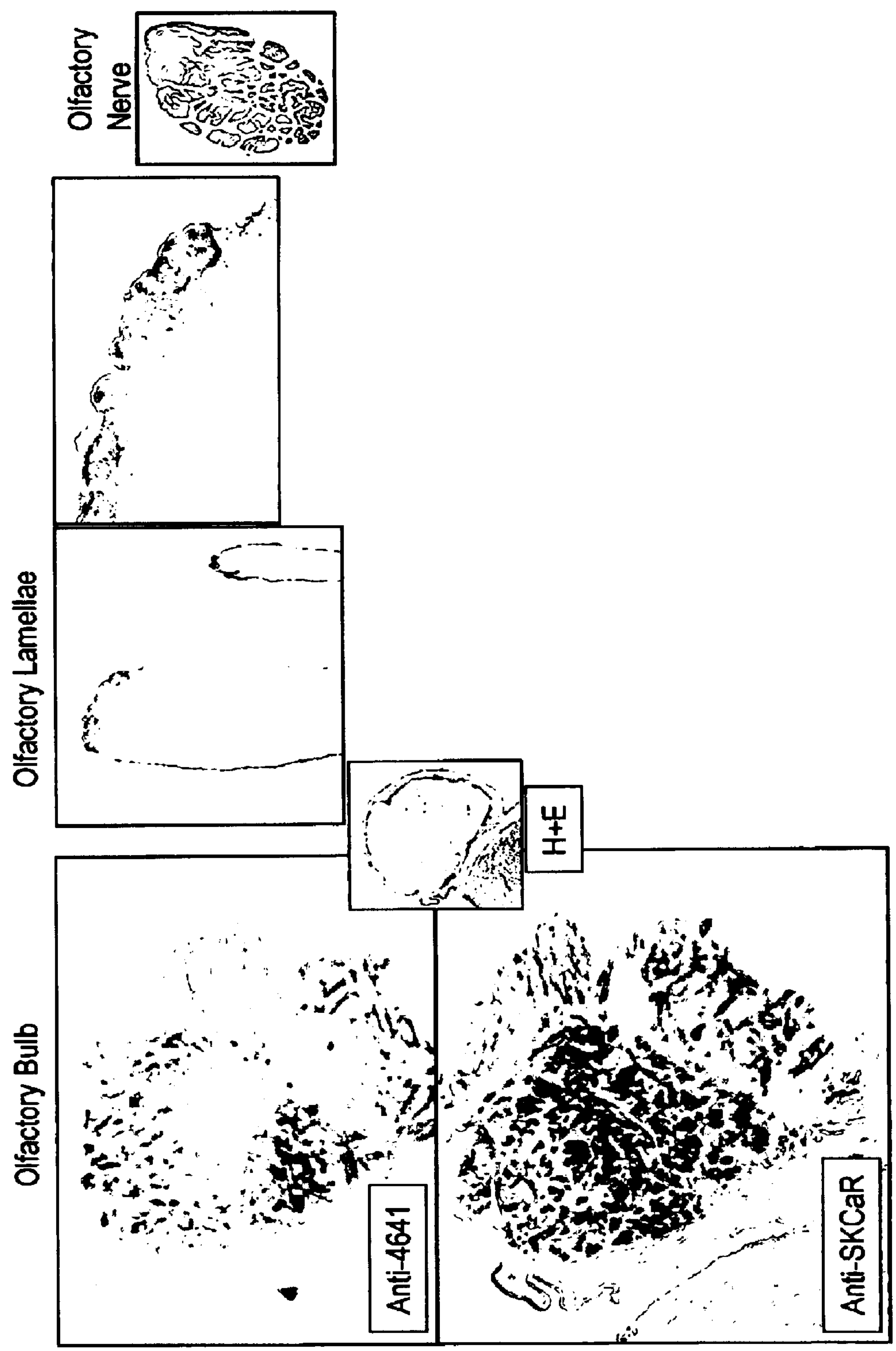
FIG. 5 is a series of photographs of immunocytochemistry showing the PVCR localization of Atlantic Salmon Olfactory Bulb Nerve and Lamellae using an anti-PVCR antibody.

PVCR protein and mRNA are localized to the olfactory lamellae, olfactory nerve and olfactory bulb of freshwater adapted larval, juvenile and adult Atlantic salmon as well as the olfactory lamellae of dogfish shark:

FIG. 5 show representative immunocytochemistry photographs of PVCR protein localization in olfactory bulb and nerve as well as olfactory lamellae in juvenile Atlantic salmon. The specificity of staining for PVCR protein is verified by the use of 2 distinct antisera each directed to a different region of the PVCR protein. Thus, antiserum anti-4641 (recognizing an extracellular domain PVCR region) and antiserum anti-SKCaR (recognizing an intracellular domain PVCR region) exhibit similar staining patterns that include various glomeruli on serial sections of olfactory bulb. Using anti-SKCaR antiserum, specific staining of PVCR proteins is observed in discrete regions of the olfactory nerve as well as epithelial cells in the nasal lamellae that are exposed to the external ionic environment.

Figure 6:
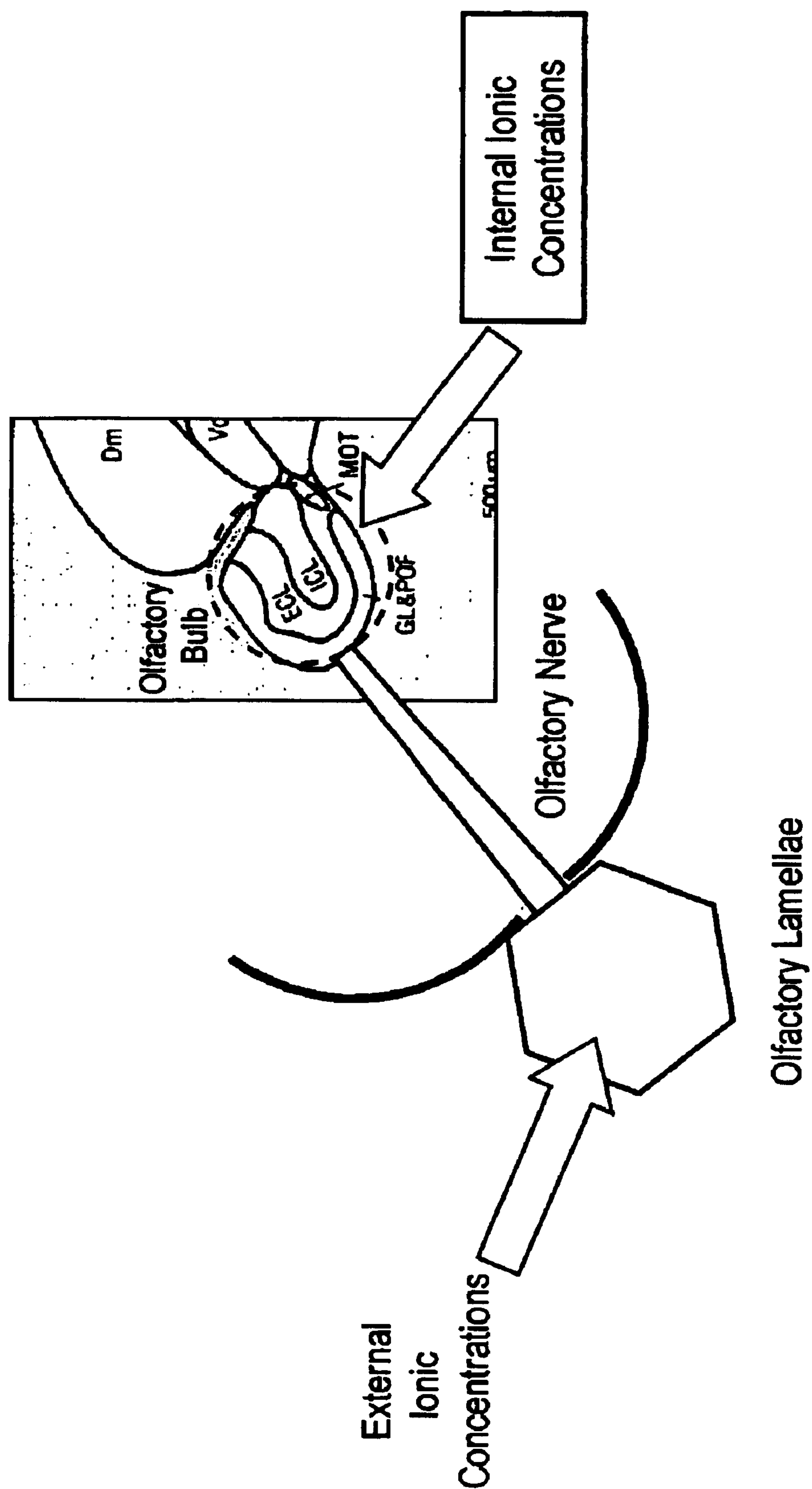
FIG. 6 is a schematic illustrating the effect of external and internal ionic concentrations on the olfactory lamellae in response to PVCR modulators. The system "senses" external $Ca^{2+}$, $Mg^{2+}$ and $Na^{+}$ with reference to internal standards.

The presence of PVCR protein in both nasal lamellae cells as well as olfactory bulb and nerve shows that these respective PVCR proteins would be able to sense both the internal and external ionic environments of the salmon. For this purpose, cells containing internally-exposed PVCRs are connected to externally-exposed PVCRs via electrical connections within the nervous system. As shown schematically in FIG. 6, these data suggest that externally and internally-exposed PVCRs function together to provide for the ability to sense the ionic concentrations of the surrounding ionic environment using as a reference the ionic concentration of the salmon's body fluids. Changes in the expression and/or sensitivity of the external set of PVCRs vs internal PVCRs would then provide a long term "memory" of the adaptational state of the fish as it travels through ionic environments of different composition. FIG. 7 shows immunocytochemistry using anti-SKCaR antiserum that reveals the presence of PVCR protein in both the developing nasal lamellae cells and olfactory bulb of larval Atlantic salmon only days after hatching (yolk sac stage). As described herein, imprinting of salmon early in development as well as during smoltification have been shown to be key intervals in the successful return of wild salmon to their natal stream. The presence of PVCR proteins at these developmental stages of salmon lifecycle indicate that PVCRs participate in this process.

Figure 8:
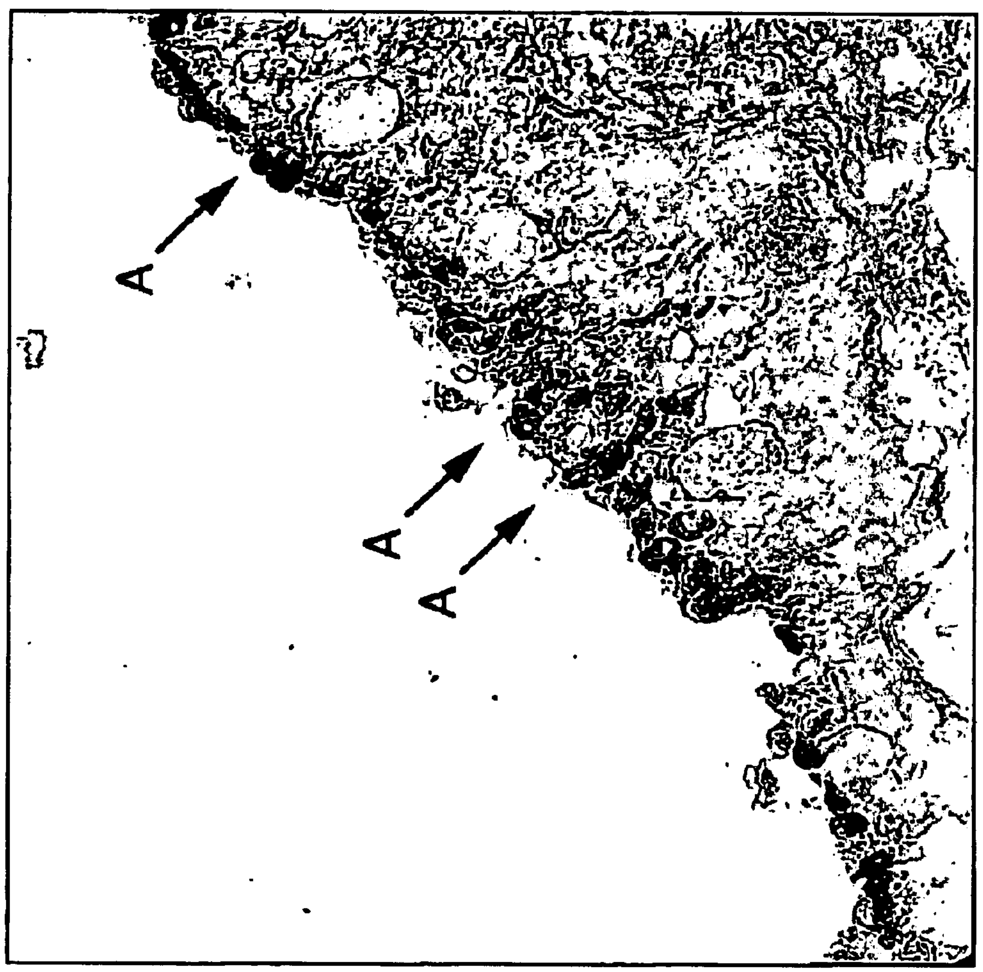
FIG. 8 is a photograph of immunocytochemistry showing the PVCR localization in nasal lamellae of dogfish shark using an anti-PVCR antibody.
Figure 9:
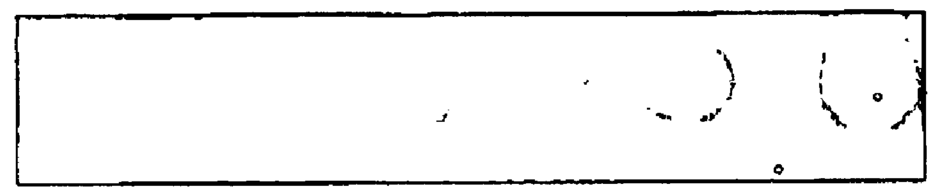
FIG. 9 is a photograph of a Southern blot of RT-PCR analyses of tissues (Lanes: 1. Gill, 2. Nasal Lamellae, 3. Urinary Bladder, 4. Kidney, 5, Intestine, 6. Stomach, 7. Liver, 8. Brain, 9. Water Blank, 10. Positive Control) from Atlantic Salmon showing the presence of PVCR mRNA in nasal lamellae of freshwater adapted.
Figure 10:
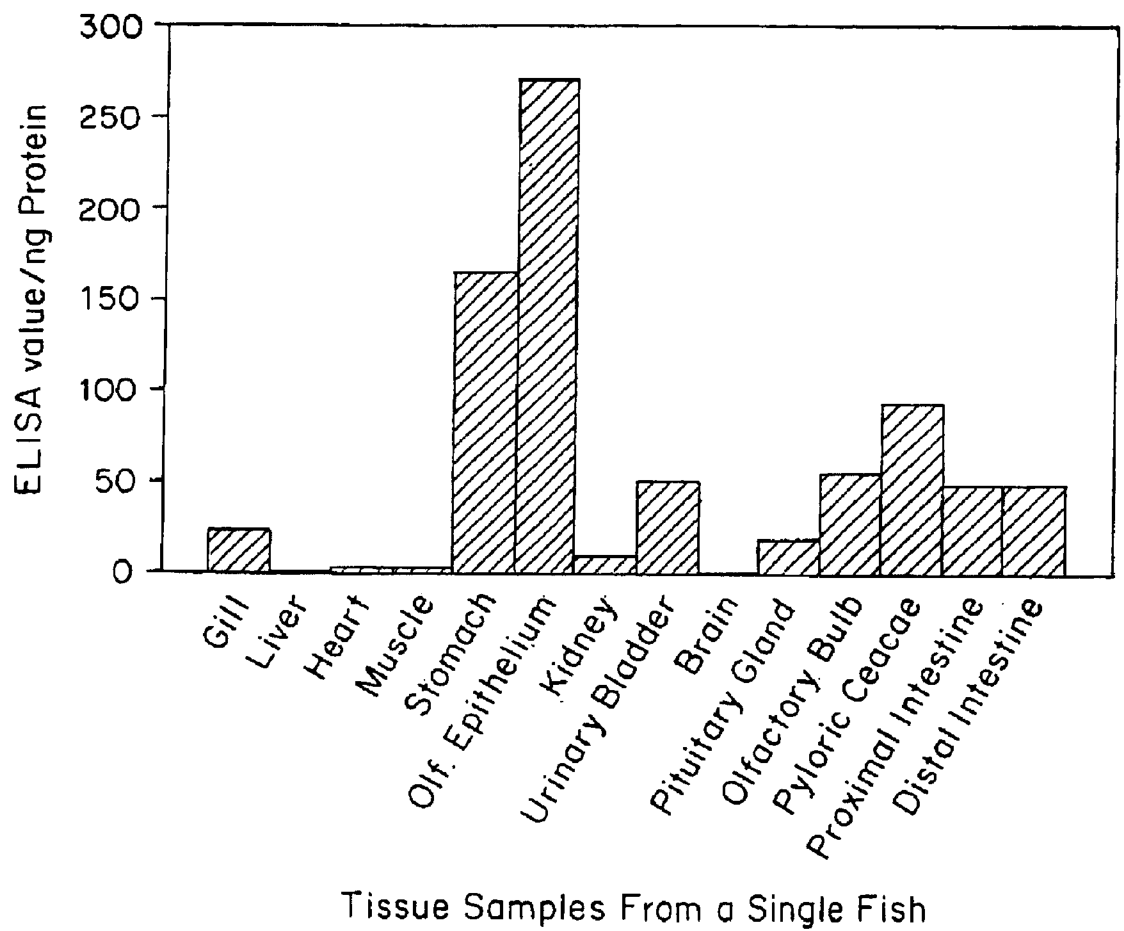
FIG. 10 is a histogram illustrating the amount of PVCR protein, as determined by an ELISA (ng) for various tissue samples (gill, liver, heart, muscle, stomach, olfactory epithelium, kidney, urinary bladder, brain, pituitary gland, olfactory bulb, pyloric ceacae, proximal intestine, and distal intestine).

Data obtained from using anti-SKCaR antiserum from other fish species including elasmobranchs display similar staining of PVCR protein in cells (marked A) their nasal lamellae (FIG. 8). Use of other methodology including RT-PCR using specific degenerate primers (FIG. 9) and ELISA methods (FIG. 10) detects the presence of PVCR proteins and mRNA in nasal lamellae of fish. While neither of these 2 techniques provide quantitative measurements as described, both sets of data are consistent and show abundant PVCR protein present in this tissue.

Figure 11:
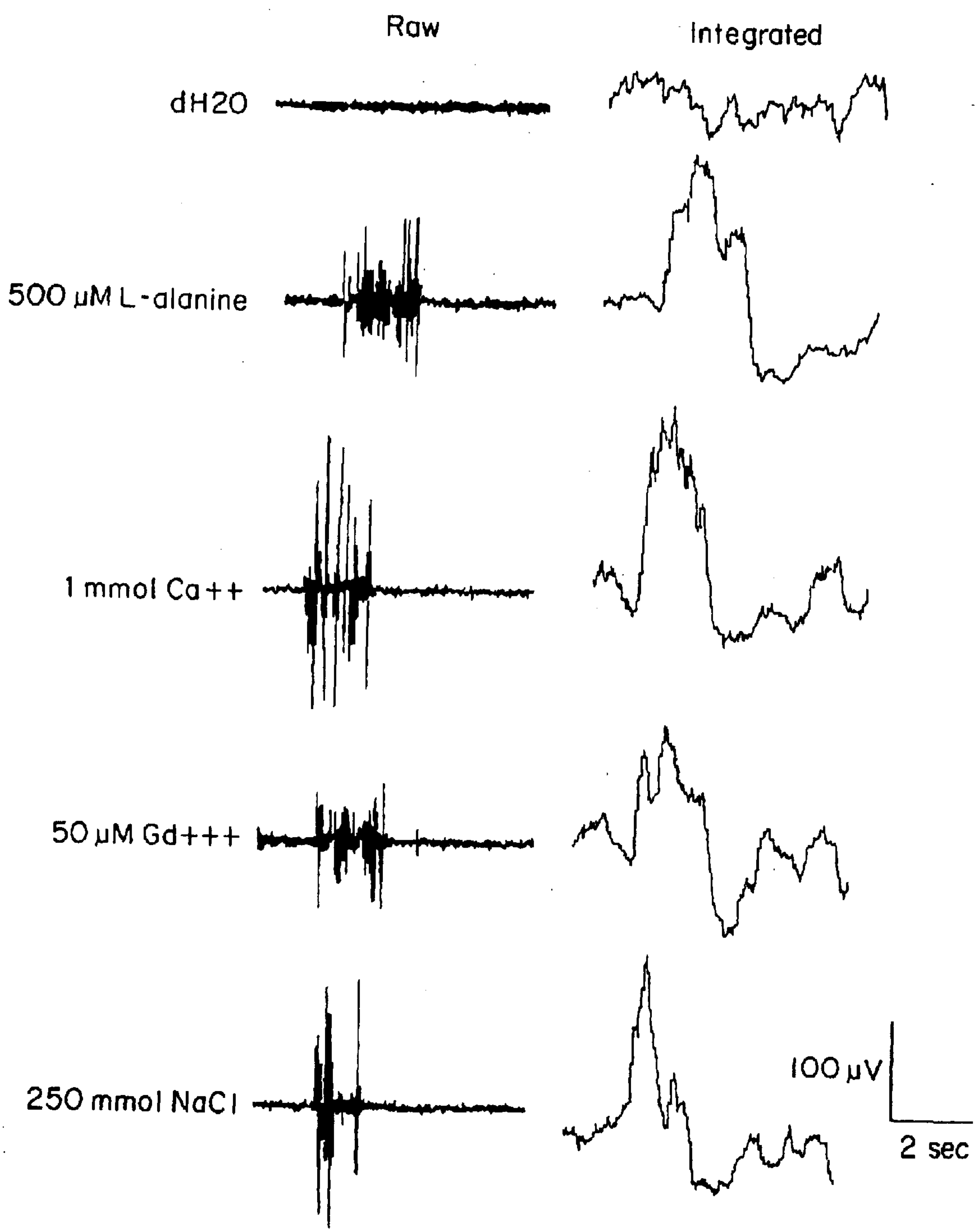
FIG. 11 shows the raw and integrated recordings from high resistance electrodes of freshwater adapted Atlantic Salmon when exposed to 500 $\mu$M L-alanine, 1 mmol calcium, 50 $\mu$M Gadolinium, and 250 mmol of NaCl. The figures shows the existence of an olfactory recording in response to L-alanine, calcium, gadolinium, and NaCl.

Measurement of extracellular electrical potentials (EEG's) from olfactory nerve from freshwater adapted Atlantic salmon reveals the presence of functional PVCR proteins:

FIG. 11 displays representative recordings obtained from 6 fish freshwater adapted juvenile Atlantic salmon (approximately 300–400 gm) using methods similar to those described in Bodznick, D. J Calcium ion: an odorant for natural water discriminations and the migratory behavior of sockeye salmon, *Comp. Physiol. A* 127:157–166 (1975), and *Hubbard, PC*, et al., Olfactory sensitivity to changes in environmental Ca2+ in the marine teleost Sparus Aurata, *J. Exp. Biol.* 203:3821–3829 (2000). After anaesthetizing the fish, it was placed in V-clamp apparatus where its gills were irrigated continuously with aerated seawater and its nasal lamellae bathed continuously by a stream of distilled water via a tube held in position in the inhalant olfactory opening. The olfactory nerves of the fish were exposed by removal of overlying bony structures. Stimuli were delivered as boluses to the olfactory epithelium via a 3 way valve where 1 cc of water containing the stimulus was rapidly injected into the tube containing a continuously stream of distilled water. Extracellular recordings were obtained using high resistance tungsten electrodes where the resultant amplified analog signals (Grass Amplifier Apparatus) were digitized, displayed and analyzed by computer using MacScope software. Using this experimental approach, stable and reproducible recordings could be obtained for up to 6 hr after the initial surgery on the fish.

Figure 12A:
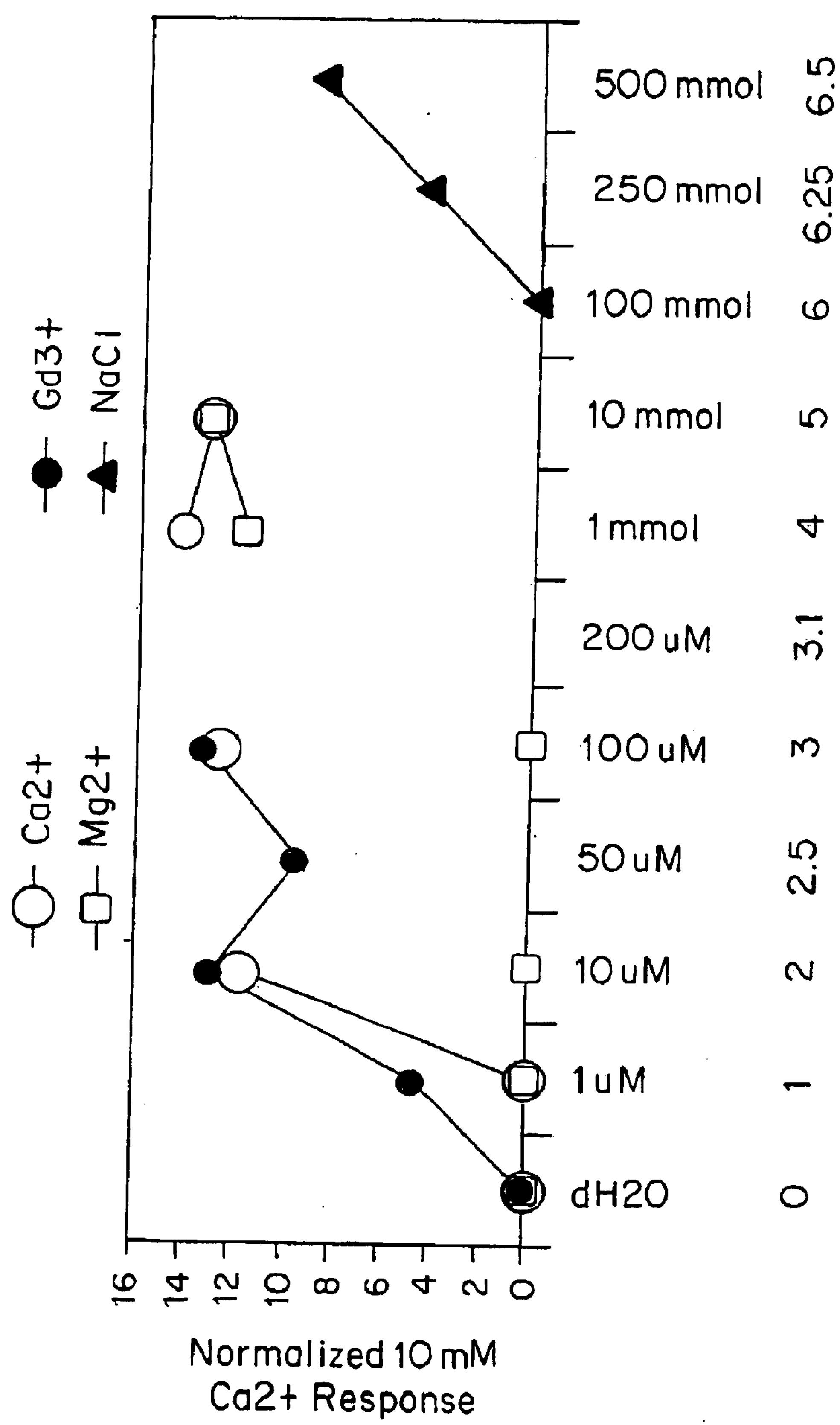
FIG. 12A is a graph showing the response data for freshwater adapted Atlantic salmon nasal lamellae of calcium, magnesium, gadolinium, and sodium chloride normalized to the signal obtained with 10 mM Calcium.

As shown in FIG. 11, irrigation of salmon olfactory epithelium with distilled water produces minimal generation of large signals in olfactory nerve. The data in FIG. 11 are displayed as both raw recordings (left column) and the corresponding integrated signals for each raw recording shown in the right column. Exposure to the olfactory epithelium to 500 micromolar L-alanine (a well known amino acid attractant for fish) produces large increases in both the firing frequency and amplitude in the olfactory nerve lasting approximately 2 seconds in duration. Similarly, application of either 1 mM $Ca^{2+}$ or 250 mM NaCl also produce responses in EEG activity. To test for the presence of functional PVCR protein, the olfactory epithelium was exposed to 50 micromolar gadolinium ($Gd^{3+}$-a PVCR agonist) and also obtained a response. FIG. 12A shows dose response data from multiple fish to various PVCR agonists or modulators where the relative magnitudes of individual olfactory nerve response were normalized relative to the response produced by the exposure of the olfactory epithelium to 10 mM $Ca^{2+}$. As shown in FIG. 12A, the olfactory epithelium of freshwater adapted juvenile salmon is very sensitive to $Ca^{2+}$ where the half maximal excitatory response ($EC_{50}$) is approximately 1–10 micromolar. Similarly, exposure of olfactory epithelium to the PVCR agonist $Gd^{3+}$ produces responses of a similar magnitude to those evoked by $Ca^{2+}$ in a concentration range of 1–10 micromolar. In contrast, olfactory epithelium responses to $Mg^{2+}$ do not occur until 10–100 micromolar solutions are applied. These dose response curves ($EC_{50}$ $Gd^{+3} \leqq Ca^{2+} < Mg^{2+}$) are similar to those obtained for PVCR modulated responses in other fish epithelium (flounder urinary bladder NaCl-mediated water transport-see SKCaR application).

In contrast, analysis of the olfactory epithelium responses to NaCl exposure shows that it is unresponsive until a concentration of 250 millimolar NaCl is applied. Since NaCl does not directly activate PVCRs in a manner such as $Gd^{+3}$ $Ca^{2+}$ or $Mg^{2+}$ but rather reduces the sensitivity of PVCRs to these agonists, these data are also consistent with the presence of an olfactory epithelium PVCR. The response evoked by exposure of the epithelium to significant concentrations of NaCl likely occurs via other PVCR independent mechanisms.

These data suggest that PVCR proteins present in olfactory epithelium are capable of sensing and generating corresponding olfactory nerve signals in response to PVCR agonists at appropriate concentrations in distilled water.

Figure 12B:
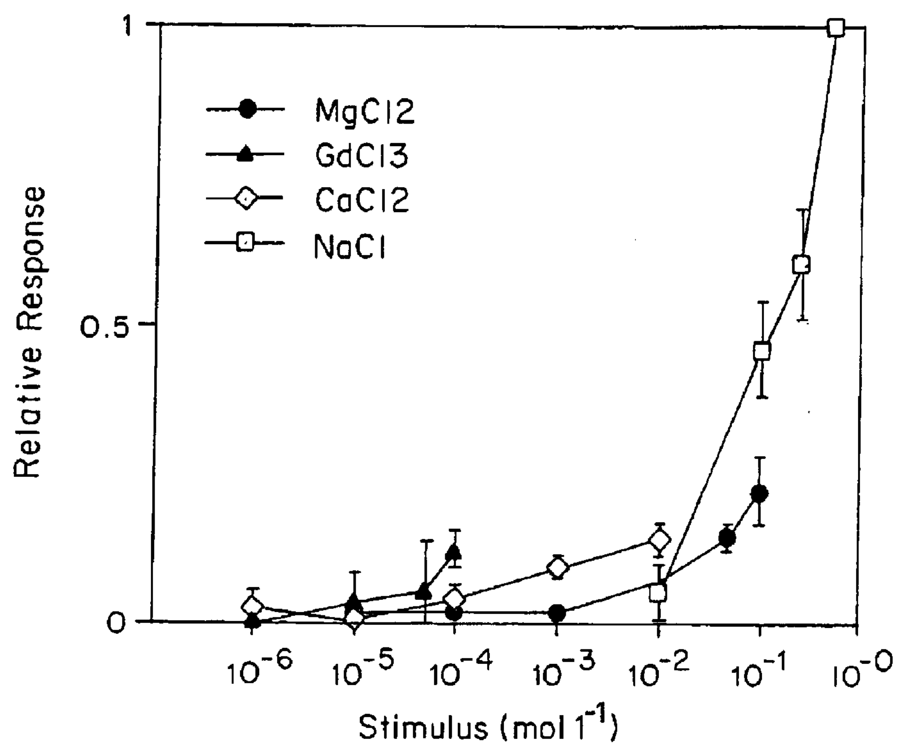
FIG. 12B is a graph showing the response data for freshwater adapted Atlantic salmon nasal lamellae of calcium, magnesium, gadolinium, and sodium chloride at various concentrations ($10^{-6}$ $mol^{-1}$, $10^{-5}$ $mol^{-1}$, $10^{-4}$ $mol^{-1}$, $10^{-3}$ $mol^{-1}$, $10^{-2}$ $mol^{-1}$, $10^{-1}$ $mol^{-1}$, $10^{0}$ $mol^{-1}$).
Figure 12C:
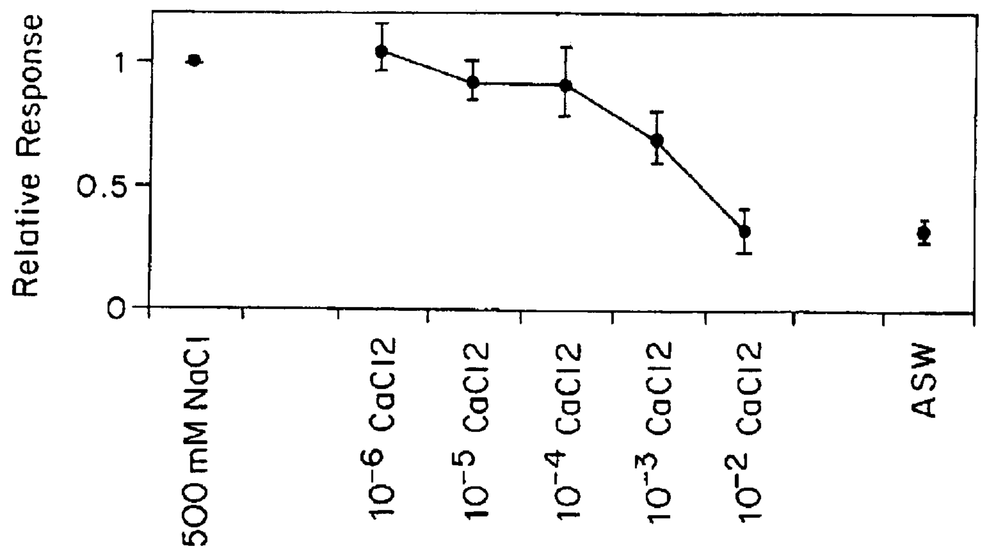
FIG. 12C is a graph showing the response data for freshwater adapted Atlantic salmon nasal lamellae of calcium at various concentrations ($10^{-6}$ $mol^{-1}$, $10^{-5}$ $mol^{-1}$, $10^{-4}$ $mol^{-1}$, $10^{-3}$ $mol^{-1}$, $10^{-2}$ $mol^{-1}$) and Artificial Seawater (ASW) in the presence of 500 mM sodium chloride.
Figure 12D:
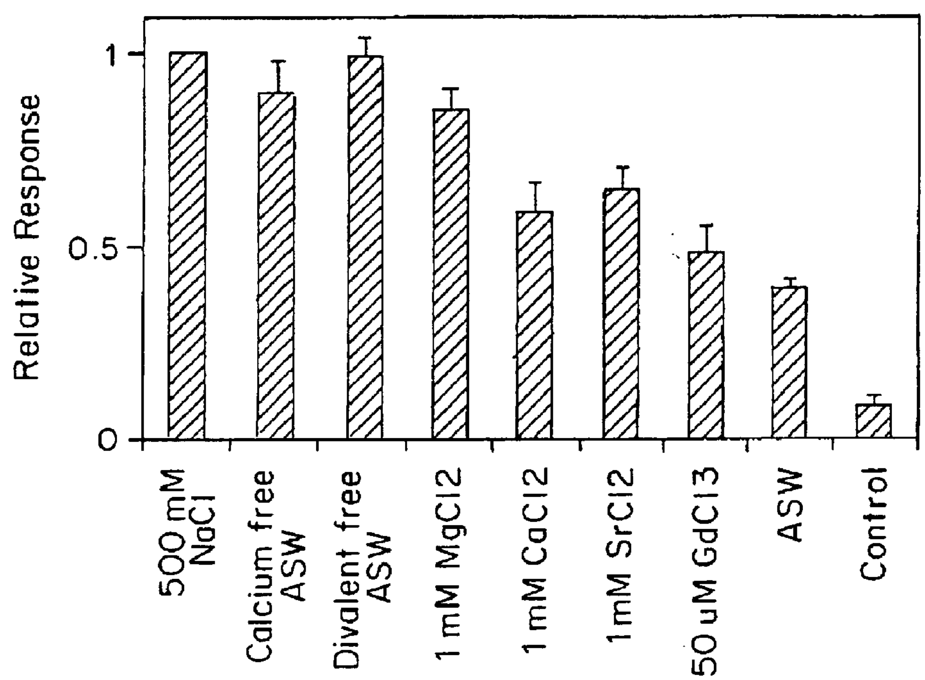
FIG. 12D is a histogram showing the response data for freshwater adapted Atlantic salmon nasal lamellae of 500 mM sodium chloride, calcium free ASW, divalent free ASW, ASW, distilled water (control); and the following PVCR agonists in combination with 500 mM sodium chloride: 1 mM magnesium, 1 mM calcium, 1 mM strontium, and 50 $\mu$M gadolinium.

Additional data, shown in FIGS. 12B–12D provide support for the presence of a functional PVCR protein(s) in the nasal lamellae of Atlantic salmon with a sensitivity profile similar to that displayed by mammalian CaR proteins. FIG. 12B shows a more complete characterization of the response of freshwater adapted Atlantic salmon smolt olfactory responses to various PVCR agonists (Mg2+, Gd3+ and Ca2+) and a single antagonist (NaCl). These data extend the data described above.

FIG. 12C shows how the PVCR agonist (Ca2+) reduces the olfactory response produced by exposure of Atlantic salmon olfactory epithelia to 500 mM NaCl. Note that the presence of 10 mM Ca2+ in a 500 mM NaCl solution produces a response that is identical to that produced by artificial seawater (ASW) exposure.

FIG. 12D shows the quantitative responses of various PVCR agonists to reduce the large response produced by irrigation of the nasal lamellae with 500 mM NaCl. Note that Ca2+ free and divalent free seawater produce a response that is similar in magnitude to that displayed after exposure to 500 mM NaCl alone. By contrast, inclusion of one PVCR agonist including 1 mM Mg2+, 1 mM Ca2+, 1 mM Sr2+ or 50 micromolar Gd3+ all significantly reduce the olfactory response to 500 mM NaCl similar to that elicited by irrigation of the nasal lamellae with artificial seawater (ASW). All of these responses are greater than that elicited by irrigation of the nasal lamellae with distilled water.

These data demonstrate that PVCR agonists are capable of modulating the olfactory response of Atlantic salmon.

Method for Stimuli and Stimulus Delivery: used to obtain the data described in FIGS. 12B–12D were obtained as follows:

Stimuli were delivered to the olfactory epithelium via a glass capillary tube placed in the inhalant olfactory opening. This tube was connected to a gravity fed tubing system allowing for switching from a background perfusion (charcoal filtered freshwater) to an experimental stimulus while maintaining a flow rate of 6–8 ml/min. Verification of the location of the stimulus delivery tubes and electrode was made by observing responses to a 'search stimulus' of 1 mL £-alanine.

Stimuli consisted of CaR agonists ($CaCl_2$, $MgCl_2$, $GdCl_3$, $SrCl_2$ and NaCl (Sigma-Aldrich), control freshwater stimulus (charcoal filtered tap water) and control seawater stimuli (ASW, Ca-free ASW, Divalent free ASW). Stimuli were presented alone or in combination with 500 mM NaCl. Ringers and artificial seawater recipes were obtained from the Biological Bulletin Compendia (all concentrations are in mM) ASW (nAcl 423, KCl 9.0, $CaCl_2$ 22.94, $MgSO_4$ 25.50, $NaHCO_3$ 2.14, pH 8.0); Ca-free ASW (NaCl 436.71, KCl 9.0, $MgCl_2$ 22.94, $MgSO_4$, 25.5, $NaHCO_3$ 2.14, pH 8.0);

Divalent free ASW (NaCl 461.85, KCl 10.73, $NAHCO_3$ 2.14, Na2SO$_4$ 7.04, pH 8.0); FW Teleost Ringer's (NaCl 111.0, KCl 5.37, $Cacl_2$ 1.0, $MgSO_4$, 0.6, HEPES 5.0, pH 7.3).

Addition of PVCR agonists such as Ca2+ or Gd3+ to distilled water containing well known salmon repellants reversibly ablates the response of the olfactory epithelium to these stimuli:

FIG. 13 shows representative data obtained from a single continuous recording where the olfactory epithelium was first exposed to a well-known repellant, mammalian finger rinse. Finger rinse is obtained by simply rinsing human fingers of adherent oils and fatty acids using distilled water and has been shown previously to be a powerful repellant stimulus both in EEG recordings as well as behavioral avoidance assays (Royce-Malmgren and W. H Watson *J. Chem. Ecology* 13:533–546 (1987)). Note however that inclusion of the PVCR agonists 5 mM $Ca^{2+}$ or 50 micromolar $Gd^{3+}$ reversibly ablated the response by the olfactory epithelium to mammalian finger rinse. These data show that PVCR agonists modulated the response of the olfactory epithelium to an odorant such as mammalian finger rinse. The ablation of responses to both the PVCR agonists as shown in FIG. 12A as well as mammalian finger rinse indicate that there are some complex interactions between PVCR proteins and other odorant receptors. It is also extremely unlikely that inclusion of PVCR agonists removed all the stimulatory components of mammalian finger rinse from solution such that they were not able to stimulate the epithelium.

Addition of PVCR agonists such as Ca2+ or Gd3+ but not NaCl to distilled water containing the well known salmon attractant L-alanine reversibly ablates the response of the olfactory epithelium to these stimuli:

FIG. 14 shows a time series of stimuli (2 min between each stimulus in a single fish) similar to that displayed on FIG. 13 except that 500 micromolar L-Alanine (a salmon attractant) was used to produce a signal in the olfactory nerve. Note that the addition of either 5 mM $Ca^{2+}$ (recording #2) or 50 micromolar $Gd^{3+}$ (recording #7) to 500 micromolar L-alanine resulted in the complete loss of the corresponding response from the olfactory nerve after injection of this mixture. In both cases, this was not due to a permanent alteration of the olfactory epithelium by either of these PVCR agonists because a subsequent identical stimulus without the PVCR agonist (recordings #3 and #8) caused a return of the signal. It is noteworthy that in the case of $Gd^{3+}$ addition, the magnitude of the subsequent L-alanine signal was decreased as compared to control (compare recordings #6 vs #8) indicating that the olfactory epithelium prefers an interval of recovery from its exposure to this potent PVCR agonist. However, the alteration of response to the L-Alanine stimulus is not permanent or nonspecific since combining the same dose of L-Alanine with 250 mM NaCl resulted initially in a similar response (recordings #4 and #9) followed by an enhanced response to L-Alanine alone (recordings #5 and #10).

In summary, the data displayed in FIGS. 13 and 14 show that inclusion of a PVCR agonist in solutions containing either a repellant (finger rinse) or attractant (L-alanine) causes a dramatic reduction in the response of the olfactory epithelium to those odorants. For both repellants and attractants, some form of complex interactions occur within olfactory epithelial cells since mixing of PVCR agonists and odorants renders the epithelia temporary unresponsive to either stimulus. While the nature of such interactions are not known at the present time, such interactions do not occur at the level of the PVCR molecule itself as shown by data from experiments using recombinant PVCR protein SKCaR. As further described herein, inclusion of amino acids in the presence of $Ca^{2+}$ enhances the response of SKCaR to ambient $Ca^{2+}$ concentrations. Regardless of their nature, these negative modulatory effects of PVCR agonists including $Ca^{2+}$ is likely to produce major effects on how freshwater salmon smell objects in their environment after transfer from a low calcium to a high calcium environment. Use of this assay system would permit the identification and analyses of both specific classes of PVCR agonists and antagonists as well as the specific effects of each PVCR modulator on specific odorants including both repellants and attractants.

Recombinant PVCR protein SKCaR possesses the capability to sense concentrations of amino acids after its expression in human embryonic kidney (HEK) cells:

Full length recombinant dogfish (*Squalus acanthias*) shark kidney calcium receptor (SKCaR) was expressed in human embryonic kidney cells using methods described herein. The ability of SKCaR to respond to individual amino acids as well as various mixtures was quantified using FURA-2 ratio imaging fluorescence.

FIG. 15 shows a comparison of fluorescence tracings of FURA2-loaded cells stably expressing SKCaR that were bathed in physiological saline (125 mM NaCl, 4 mM KCl, 0.5 mM $CaCl_2$, 0.5 $MgCl_2$, 20 mM HEPES (NaOH), 0.1% D-glucose pH 7.4) in the presence or absence of 10 mM L-Isoleucine (L-Ile) before being placed into the fluorimeter. Baseline extracellular $Ca^{2+}$ concentration was 0.5 mM. Aliquots of $Ca^{2+}$ were added to produce final extracellular concentrations of 2.5 mM, 5 mM, 7.5 mM, 10 mM and 20 mM $Ca^{2+}$ with changes in the fluorescence recorded. Note that increases in cell fluorescence were greater in the presence of 10 mM Phe for extracellular $Ca^{2+}$ concentrations less than 10 mM.

FIG. 16 shows data plotted from multiple experiments as described in FIG. 15 where the effects of 10 mM Phe, 10 mM Ile or an amino acid mixture (AA Mixture) containing all L-isomers in the following concentrations in micromoles/liter: 50 Phe, 50 Trp, 80 His, 60 Tyr, 30 Cys, 300 Ala, 200 Thr, 50 Asn, 600 Gln, 125 Ser, 30 Glu, 250 Gly, 180 Pro, 250 Val, 30 Met, 10 Asp, 200 Lys, 100 Arg, 75 Ile, 150 Leu. Note that both 10 mM Phe and 10 mM Ile as well as the mixture of amino acids increase SKCaR's response to a given $Ca^{2+}$ concentration. Thus, these data show that presence of amino acids either alone or in combination increase the apparent sensitivity to $Ca^{2+}$ permitting SKCaR to "sense" amino acids in the presence of physiological concentrations of $Ca^{2+}$. These data obtained for SKCaR are comparable to those obtained for the human CaR.

The significance of these data for aquatic organisms stand in marked contrast to the roles of human CaRs amino acid sensing capabilities. FIG. 15 shows that SKCaR's maximal capability to sense amino acids is confined to a range of $Ca^{2+}$ that is present both in aquatic external environments as well as the body fluids of various fish. The following physiological processes occur: 1) Sensing of amino acids in the proximal intestine and pyloric caeca of fish: The PVCR present on the apical surface of intestinal epithelial cells is capable of responding to amino acids such as tryptophan as part of the Process II. Inclusion of tryptophan in the feed of fish interacts with the intestinal PVCR to improve the development of juvenile anadromous fish to tolerate seawater transfer. 2) In both adult, juvenile and larval fish, PVCR localized to the apical membrane of stomach and intestinal epithelial cells could "sense" the presence of amino acids produced by the proteolysis of proteins into amino acids. This mechanism could be used to inform both epithelial and neuroendocrine cells of the intestine of the presence of nutrients (proteins) and trigger a multitude of responses including growth and differentiation of intestinal epithelia as well as their accompanying transport proteins, secretion or reabsorption of ions such as gastric acid. The apical PVCR also regulates the secretion of intestinal hormones such as cholecystokin (CCK) and others. 3) PVCR proteins present in cells of the nasal lamellae of fish to "smell" both water salinity (via $Ca^{2+}$, $Mg^{2+}$ and NaCl) and amino acids which is an example of an attractant. At the present time, it is unclear whether the amino acid sensing capabilities of PVCRs are utilized by the olfactory epithelium to enable fish to smell various amino acid attractants.

These data show that PVCR sensing of amino acids occurs in a range of extracellular calcium that is present in various concentrations of seawater present in estuaries and fish migration routes as well as various compartments of a fish's body including serum and body cavities including intestine, pyloric caeca and kidney, where transepithelial amino acid absorption occurs. These data constitute the first report showing the amino acid sensitivity of a PVCR in fish.

EXAMPLE 4

Olfactory Nerve Recordings of Freshwater Adapted Atlantic Salmon Under Conditions that Simulate Freshwater to Seawater Transfer FIG. 17 shows a representative recording obtained from a single freshwater adapted Atlantic salmon smolt. The upper left hand panel shows a recording of electrical impulses obtained from the olfactory nerve of these fish during an interval when distilled water is used to irrigate their nasal lamellae. Note that because these fish are freshwater-adapted, only rare large deflections (indicated by 2 dashed arrows) of the recording record are observed after irrigation of the nasal lamellae with distilled water (larger downward arrow). By contrast, if the nasal lamellae of the same fish is now irrigated with artificial seawater (lower panel-arrow), there is now the onset of multiple large scale electrical impulses that prevent the detection of specific odorants such as L-Ala (shown at upper right during perfusion with distilled water). These data show what occurs to freshwater adapted Atlantic salmon smolt when they are transferred from freshwater directly to seawater, and are not subject to the methods of the present invention. As disclosed herein, these data show that there is a temporary interval where freshwater adapted fish are unable to optimally smell or detect food in seawater due to the dramatic change in their surrounding ionic environment. This phenomenon likely is responsible for the significantly decreased feeding exhibited by such fish during the interval following seawater transfer. In contrast, anadromous fish that are transferred from freshwater directly to seawater after exposure to Process I or Process II in freshwater begin feeding 48 hours after seawater transfer. The observed difference in food consumption between control vs. fish treated with the methods of the present invention during the interval immediately after seawater transfer is modulation of the expression and/or sensitivity of at least PVCR in the olfactory organs of these fish.

Companion patent application Ser. No. 09/687,373, entitled "Growing Marine Fish in Fresh Water," filed on Oct. 12, 2000; patent application Ser. No. 09/687,476, entitled "Methods for Raising Pre-adult Anadromous Fish," filed on Oct. 12, 2000; patent application Ser. No. 09/687,372, entitled "Methods for Raising Pre-adult Anadromous Fish," filed on Oct. 12, 2000; patent application Ser. No. 09/687,477, entitled "Methods for Raising Pre-adult Anadromous Fish," filed on Oct. 12, 2000 Provisional Patent Application No. 60/240,392, entitled "Polyvalent Cation Sensing Receptor Proteins in Aquatic Species," filed on Oct. 12, 2000; Provisional Patent Application No. 60/240,003, entitled "Polyvalent Cation Sensing Receptor Proteins in Aquatic Species," filed on Oct. 12, 2000; patent application Ser. No. 09/975,553, entitled "Methods for Raising Pre-adult Anadromous Fish," filed Oct. 11, 2001; PCT Patent Application No.: PCT/US01/31562, entitled "Polyvalent Cation Sensing Receptor in Aquatic Species," filed Oct. 11, 2001; Patent Application No.: PCT/US01/31625, entitled "Growing Marine Fish in Fresh Water," filed Oct. 11, 2001; are all hereby incorporated by reference in their entirety.

Additionally, application Ser. No. 09/162,021, filed on Sep. 28, 1998, International PCT application No. PCT/US97/05031, filed on Mar. 27, 1997, and application Ser. No. 08/622,738 filed Mar. 27, 1996, all entitled, "Polycation Sensing Receptor in Aquatic Species and Methods of Use Thereof" are all hereby incorporated by reference in their entirety.

Nearing, J. et al., "Polyvalent Cation Receptor Proteins (CaRs) are salinity Sensors in Fish," PNAS 99(14): 9231–9236 (2002) is incorporated by referenced in its entirety.

All relevant portions of literature articles, references, patent applications, patent publications, and patents cited herein are hereby incorporated by referenced in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of imprinting fish in freshwater with at least one odorant for said fish and causing the imprinted fish to react to said odorant in seawater, wherein the fish are maintained in freshwater prior to transfer to seawater, comprising:

a. adding at least one Polyvalent Cation Sensing Receptor (PVCR) modulator to the freshwater in an amount sufficient to modulate expression and/or sensitivity of at least one PVCR, said PVCR modulator being one which alters olfactory sensing of the fish to the odorant;

b. adding feed for fish consumption to the freshwater, said feed containing said odorant and an amount of NaCl sufficient to contribute to a significantly increased level of said PVCR modulator in serum of the fish upon consumption of the feed, whereby the fish are imprinted with the odorant;

c. transferring the imprinted fish to seawater, and d. providing a source of said odorant in the seawater to which the imprinted fish are transferred, thereby causing the imprinted fish to react to said odorant.

2. The method of claim 1, wherein increased expression of at least one PVCR is maintained until the fish are transferred to seawater.

3. The method of claim 2, wherein altering olfactory sensing of fish to the odorant further includes generating an olfactory nerve impulse after binding of the odorant to the olfactory lamellae in the fish.

4. The method of claim 3, wherein the PVCR modulator is selected from the group consisting of a divalent cation, a trivalent cation, an aminoglycoside, an organic polycation, an amino acid, a Type I Calcimimetic, a Type II Calcimimetic, 1,25 dihydroxyvitamin D, a cytokine, and macrophage chemotatic peptide-1.

5. The method of claim 4, wherein the divalent cation is calcium, magnesium, or both.

6. The method of claim 4, wherein the organic polycation is putrescine, spermine, spermidine, or combination thereof.

7. The method of claim 4, further including exposing the fish to a photoperiod.

8. The method of claim 7, further including adding a PVCR modulator to the feed.

9. The method of claim 1, wherein the source of said odorant in the seawater is a feed for fish consumption.

10. A method of imprinting fish in freshwater with at least one odorant for said fish and causing the imprinted fish to react to said odorant in seawater, wherein the fish are maintained in freshwater prior to transfer to seawater, comprising:

a. adding at least one Polyvalent Cation Sensing Receptor (PVCR) modulator to the freshwater in an amount sufficient to modulate expression and/or sensitivity of at least one PVCR, said PVCR modulator being one which alters olfactory sensing of the fish to the odorant;

b. adding feed for fish consumption to the freshwater, said feed containing an amount of NaCl sufficient to contribute to a significantly increased level of said PVCR modulator in serum of the fish upon consumption of the feed;

c. adding said odorant to the freshwater, whereby the fish are imprinted with the odorant;

d. transferring the imprinted fish to seawater; and e. providing a source of said odorant in the seawater to which the imprinted fish are transferred, thereby causing the imprinted fish to react to said odorant.

11. The method of claim 10, wherein the odorant is a fish attractant.

12. The method of claim 11, wherein the attractant is an amino acid, a nucleotide, organic compound, or combination thereof.

13. The method of claim 10, wherein the odorant is a fish repellant.

14. The method of claim 13, where the repellant is derived from a mammalian finger rinse.

15. A method for growing anadromous fish by feeding in seawater with at least one attractant for said anadromous fish, wherein the anadromous fish are imprinted in freshwater with the attractant and wherein the anadromous fish are maintained in freshwater prior to transfer to seawater, comprising:

a. transferring the imprinted anadromous fish to seawater; and b. adding feed for fish consumption to the seawater, said feed containing said attractant and a source of nutrition, thereby causing the imprinted anadromous fish to react to the attractant and consume the feed.

16. The method of claim 15, wherein the anadromous fish are imprinted with the attractant by:

a. adding at least one Polyvalent Cation Sensing Receptor (PVCR) modulator to the freshwater in an amount sufficient to modulate expression and/or sensitivity of at least one PVCR, said PVCR modulator being one which alters olfactory sensing of fish to the odorant; and b. adding feed for fish consumption to the freshwater, said feed containing said odorant and an amount of NaCl sufficient to contribute to a significantly increased level of said PVCR modulator in serum of the anadromous fish upon consumption of the feed, whereby the anadromous fish are imprinted with the attractant.

17. A feed for consumption by anadromous fish in freshwater, wherein the feed comprises:

a. one or more sources of nutrition;

b. an amount of NaCl between about 10,000 mg/kg and about 100,000 mg/kg;

c. at least one attractant for said fish; and d. an amount of tryptophan between about 1 and about 10 gm/kg.

18. A method of attracting or homing anadromous fish that have been imprinted in freshwater with at least one attractant for said fish, wherein the anadromous fish are maintained in freshwater prior to transfer to seawater, comprising:

a. transferring imprinted anadromous fish to seawater; and b. exposing the imprinted anadromous fish to a source of said attractant in the seawater in a sufficient amount to attract or home the anadromous fish.

19. The method of claim 18, wherein exposing the fish to said attractant further includes adhering the attractant to an object and placing said object having the attractant adhered thereto in the seawater.

20. The method of claim 19, wherein the object is netting or fish lure.

21. A method of repelling anadromous fish in seawater that have been imprinted in freshwater with at least one repellant for said fish, wherein the anadromous fish are maintained in freshwater prior to transfer to seawater, comprising:

a. transferring imprinted anadromous fish to seawater; and b. exposing the imprinted anadromous fish to a source of the repellant in seawater in a sufficient amount to repel the anadromous fish.

22. The method of claim 21, wherein exposing the fish to the repellant further includes adhering the repellant to an object and placing said object having the repellant adhered thereto in the seawater.

23. A method of identifying a fish odorant, comprising:

a. exposing to at least one fish odorant to be tested to tissue of fish, wherein at least one Polyvalent Cation Sensing Receptor (PVCR) is present in the tissue; and b. assessing the magnitude or characteristics of an olfactory nerve response, wherein the presence or increase of the olfactory nerve impulse indicates the presence of the odorant, and the absence of a olfactory nerve impulse indicates the absence of the odorant.

24. The method of claim 23, further including determining whether the odorant is an attractant or repellant by performing a behavioral attractant assay, a behavioral avoidance assay, or both.

25. A method of increasing food consumption of anadromous fish, wherein the anadromous fish are maintained in freshwater prior to transfer to seawater, comprising:

a. subjecting the anadromous fish to at least one Polyvalent Cation Sensing Receptor (PVCR) modulator in the freshwater in an amount sufficient to modulate expression and/or sensitivity of at least one PVCR, said PVCR modulator being one which alters olfactory sensing of fish to at least one attractant;

b. adding feed for fish consumption to the freshwater, said feed containing the attractant and an amount of NaCl sufficient to contribute to a significantly increased level of said PVCR modulator in serum of the anadromous fish upon consumption of the feed, whereby the anadromous fish are imprinted with the odorant;

c. transferring the imprinted anadromous fish to seawater; and d. adding feed for fish consumption to the seawater, wherein the feed contains a source of nutrition and the attractant used in step b), whereby the attractant causes the imprinted anadromous fish to consume the feed.

26. A method of increasing the growth rate of one or more anadromous fish, wherein the anadromous fish are maintained in freshwater prior to transfer to seawater, comprising:

a. subjecting the anadromous fish to at least one Polyvalent Cation Sensing Receptor (PVCR) modulator in the freshwater in an amount sufficient to modulate expression and/or sensitivity of at least one PVCR, said PVCR modulator being one which alters olfactory sensing of fish to at least one attractant;

b. adding feed for fish consumption to the freshwater, said feed containing the attractant and an amount of NaCl sufficient to contribute to a significantly increased level of said PVCR modulator in serum of the anadromous fish upon consumption of the feed, whereby the anadromous fish are imprinted with the attractant;

c. transferring the imprinted anadromous fish to seawater; and d. adding feed for fish consumption to the seawater, wherein the feed contains a source of nutrition and the attractant used in step b), whereby the attractant causes the imprinted anadromous fish to consume the feed.

27. A method of increasing survival of anadromous fish after their transfer to seawater, wherein the fish undergo smoltification in freshwater, comprising:

a. subjecting the anadromous fish to at least one Polyvalent Cation Sensing Receptor (PVCR) modulator in the freshwater in an amount sufficient to modulate expression and/or sensitivity of at least one PVCR, said PVCR modulator being one which alters olfactory sensing of fish to at least one attractant;

b. adding feed for fish consumption to the freshwater, said feed containing the attractant and an amount of NaCl sufficient to contribute to a significantly increased level of said PVCR modulator in serum of the anadromous fish upon consumption of the feed, whereby the anadromous fish are imprinted with the attractant;

c. transferring the imprinted anadromous fish to seawater; and d. adding feed for fish consumption to the seawater, wherein the feed contains a source of nutrition and the attractant used in step b), whereby the attractant causes the imprinted anadromous fish to consume the feed.

28. A method for improving the feed conversion ratio (FCR) for anadromous fish, wherein the pre-adult anadromous fish are maintained in freshwater prior to transfer to seawater, comprising:

a. subjecting the anadromous fish to at least one Polyvalent Cation Sensing Receptor (PVCR) modulator in the freshwater in an amount sufficient to modulate expression and/or sensitivity of at least one PVCR, said PVCR modulator being one which alters olfactory sensing of fish to at least one attractant;

b. adding feed for fish consumption to the freshwater, said feed containing the attractant and an amount of NaCl sufficient to contribute to a significantly increased level of said PVCR modulator in serum of the anadromous fish upon consumption of the feed, whereby the anadromous fish are imprinted with the attractant;

c. transferring the imprinted anadromous fish to seawater; and d. adding feed for fish consumption to the seawater, wherein the feed contains a source of nutrition and the attractant used in step b), whereby the attractant causes the imprinted anadromous fish to consume the feed.

29. A method of imprinting anadromous fish in freshwater with at least one odorant for said fish and causing the imprinted fish to react to said odorant in seawater, wherein the anadromous fish are maintained in freshwater prior to transfer to seawater, comprising:

a. adding magnesium and calcium to the freshwater in an amount sufficient to modulate expression and/or sensitivity of at least one Polyvalent Cation Sensing Receptor (PVCR), said PVCR being modulated to alter olfactory sensing of the fish to the odorant;

b. adding feed for fish consumption to the freshwater, said feed containing said odorant and an amount of NaCl sufficient to contribute to a significantly increased level of calcium and/or magnesium in serum of the pre-adult anadromous fish upon consumption of the feed, whereby the anadromous fish are imprinted with the odorant;

c. transferring the imprinted anadromous fish to seawater; and d. providing a source of said odorant in the seawater to which the imprinted fish are transferred, thereby causing the imprinted anadromous fish to react to said odorant.

30. The method of claim 29, wherein altering olfactory sensing of fish to the odorant further includes generating an olfactory nerve impulse after binding of the odorant to the olfactory lamellae in the fish.

31. A method of imprinting anadromous fish in freshwater with at least one odorant for said fish and causing the imprinted anadromous fish to react to said odorant in seawater, wherein the anadromous fish are maintained in freshwater prior to transfer to seawater, comprising:

a. adding magnesium and calcium to the freshwater in an amount sufficient to modulate expression and/or sensitivity of at least one Polyvalent Cation Sensing Receptor (PVCR);

b. adding said odorant to the freshwater, wherein said magnesium and calcium alters olfactory sensing of the fish to the odorant;

c. adding feed for fish consumption to the freshwater, said feed containing an amount of NaCl sufficient to contribute to a significantly increased level of calcium and/or magnesium in serum of the pre-adult anadromous fish upon consumption of the feed, whereby the anadromous fish are imprinted with the odorant;

c. transferring the imprinted anadromous fish to seawater; and d. providing a source of said odorant in the seawater to which the imprinted anadromous fish are transferred, thereby causing the imprinted anadromous fish to react to said odorant.

32. A method of imprinting marine fish in freshwater to at least one odorant for said fish and causing the imprinted marine fish to react to said odorant in seawater, comprising:

a. transferring the marine fish to freshwater having at least one Polyvalent Cation Sensing Receptor (PVCR) modulator in an amount sufficient to modulate expression and/or sensitivity of at least one PVCR, said PVCR modulator being one which alters olfactory sensing of the fish to the odorant;

b. adding feed for fish consumption to the freshwater, said feed containing said odorant and an amount of NaCl sufficient to contribute to a significantly increased level of said PVCR modulator in serum of the marine fish upon consumption of the feed, whereby the marine fish are imprinted with the odorant;

c. transferring the imprinted marine fish to seawater; and d. providing a source of said odorant in the seawater to which the imprinted marine fish are transferred, thereby causing the imprinted marine fish to react to said odorant.

33. A method of imprinting fish to at least one odorant for said fish and causing the imprinted fish to react to said odorant, wherein the fish are maintained in freshwater, comprising:

a. adding at least one Polyvalent Cation Sensing Receptor (PVCR) modulator to the freshwater in an amount sufficient to modulate expression and/or sensitivity of at least one PVCR, said PVCR modulator being one which alters olfactory sensing of the fish to the odorant;

b. adding feed for fish consumption to the freshwater, said feed containing said odorant and an amount of NaCl sufficient to contribute to a significantly increased level of said PVCR modulator in serum of the fish upon consumption of the feed, whereby the fish are imprinted with the odorant; and c. providing a source of said odorant to the imprinted fish, thereby causing the fish to react to the odorant.

34. A method of imprinting fish to at least one odorant for said fish and causing the imprinted fish to react to said odorant, wherein the fish are maintained in a first body of water, comprising:

a. adding at least one Polyvalent Cation Sensing Receptor (PVCR) modulator to the first body of water in an amount sufficient to modulate expression and/or sensitivity of at least one PVCR, said PVCR modulator being one which alters olfactory sensing of the fish to the odorant;

b. adding feed for fish consumption to the first body of water, said feed containing said odorant and an amount of NaCl sufficient to contribute to a significantly increased level of said PVCR modulator in serum of the fish upon consumption of the feed, whereby the fish are imprinted with the odorant;

c. transferring the imprinted fish to a second body of water; and d. providing a source of said odorant in the second body of water to which the imprinted fish are transferred, thereby causing the imprinted fish to react to said odorant.

35. A method of imprinting fish to at least one odorant for said fish and causing the imprinted fish to react to said odorant, wherein the fish are maintained in a first body of water, comprising:

a. adding at least one Polyvalent Cation Sensing Receptor (PVCR) modulator to a first body of water in an amount sufficient to modulate expression and/or sensitivity of at least one PVCR, said PVCR modulator being one which alters olfactory sensing of the fish to the odorant;

b. adding feed for fish consumption to the water, said feed containing an amount of NaCl sufficient to contribute to a significantly increased level of said PVCR modulator in serum of the fish upon consumption of the feed;

c. adding said odorant to the water, whereby the fish are imprinted with the odorant; and d. transferring the imprinted fish to a second body of water; and e. providing a source of said odorant in the second body of water to which the imprinted fish are transferred, thereby causing the imprinted fish to react to said odorant.

36. A method of imprinting fish in freshwater with at least one repellant for said fish, wherein the fish are maintained in freshwater prior to transfer to seawater, comprising:

a. adding at least one Polyvalent Cation Sensing Receptor (PVCR) modulator to the freshwater in an amount sufficient to modulate expression and/or sensitivity of at least one PVCR, said PVCR modulator being one which alters olfactory sensing of the fish to the repellant;

b. adding feed for fish consumption to the freshwater, the feed containing an amount of NaCl sufficient to contribute to a significantly increased level of said PVCR modulator in serum of the fish upon consumption of the feed; and c. adding a source of the repellant to the freshwater, whereby the fish are imprinted with the repellant.

* * * * *

SEQUENCE LISTING

```
<160> NUMBER OF SEQ ID NOS: 13

<210> SEQ ID NO 1
<211> LENGTH: 594
<212> TYPE: DNA
<213> ORGANISM: Salmo salar
<220> FEATURE:
<221> NAME/KEY: misc_feature
<223> OTHER INFORMATION: R=A or G

<400> SEQUENCE: 1
```

-continued

```
cttggcatta tgctctgtgc tgggggtatt cttgacagca ttcgtgatgg gagtgtttat     60

caaatttcgc aacaccccaa ttgttaaggc cacaaacaga gagctatcct acctcctcct    120

gttctcactc atctgctgtt tctccagttc cctcatcttc attggtgaac cccaggactg    180

gacatgccgt ctacgccagc ctgcattcgg gataagtttt gttctctgca tctcctgcat    240

cctggtaaaa actaaccgag tacttctagt gttcgaagcc aagatcccca ccagtctcca    300

tcgtaagtgg tgggggctaa acttgcagtt cctgttagtg ttcctgttca catttgtgca    360

agtgatgata tgtgtggtct ggctttacaa tgctcctccg gcgagctaca ggaaccatga    420

cattgatgag ataattttca ttacatgcaa tgagggctct atgatggcgc ttggcttcct    480

aattgggtac acatgcctgc tggcagccat atrcttcttc tttgcattta aatcacgaaa    540

actgccagag aactttactg aggctaagtt catcaccttc agcatgctca tctt          594


<210> SEQ ID NO 2
<211> LENGTH: 197
<212> TYPE: PRT
<213> ORGANISM: Salmo salar
<220> FEATURE:
<221> NAME/KEY: misc_feature
<222> LOCATION: (171)..(171)
<223> OTHER INFORMATION: Xaa = Any amino acid

<400> SEQUENCE: 2

Leu Ala Leu Cys Ser Val Leu Gly Val Phe Leu Thr Ala Phe Val Met
1               5                   10                  15

Gly Val Phe Ile Lys Phe Arg Asn Thr Pro Ile Val Lys Ala Thr Asn
            20                  25                  30

Arg Glu Leu Ser Tyr Leu Leu Leu Phe Ser Leu Ile Cys Cys Phe Ser
        35                  40                  45

Ser Ser Leu Ile Phe Ile Gly Glu Pro Gln Asp Trp Thr Cys Arg Leu
    50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Trp Gly Leu Asn Leu Gln Phe Leu Leu
            100                 105                 110

Val Phe Leu Phe Thr Phe Val Gln Val Met Ile Cys Val Val Trp Leu
        115                 120                 125

Tyr Asn Ala Pro Pro Ala Ser Tyr Arg Asn His Asp Ile Asp Glu Ile
    130                 135                 140

Ile Phe Ile Thr Cys Asn Glu Gly Ser Met Met Ala Leu Gly Phe Leu
145                 150                 155                 160

Ile Gly Tyr Thr Cys Leu Leu Ala Ala Ile Xaa Phe Phe Phe Ala Phe
                165                 170                 175

Lys Ser Arg Lys Leu Pro Glu Asn Phe Thr Glu Ala Lys Phe Ile Thr
            180                 185                 190

Phe Ser Met Leu Ile
        195


<210> SEQ ID NO 3
<211> LENGTH: 594
<212> TYPE: DNA
<213> ORGANISM: Salvelinus alpinus

<400> SEQUENCE: 3
```

-continued

```
cttggcatta tgctctgtgc tgggggtatt cttgacagca ttcgtgatgg gagtgtttat     60

cagatttcgc aacaccccaa ttgttaaggc cacaaacaga gagctatcct acctcctcct    120

gttctcactc atctgctgtt tctccagctc cctcatcttc attggtgaac cccaggactg    180

gacatgccgt ctacgccagc ctgcattcgg gataagtttt gttctctgca tctcctgcat    240

cctggtcaaa actaaccgag tacttctagt gttcgaagcc aagatcccca ccagtctcca    300

tcgtaagtgg tgggggctaa acttgcagtt cctgttggtg ttcctgttca catttgtgca    360

agtgatgata tgtgtggtct ggctttacaa tgctcctccg gcgagctaca ggaaccatga    420

cattgatgag ataattttca ttacatgcaa tgagggctct atgatggcgc tcggcttcct    480

aattgggtac acatgcctgc tggcagccat atgcttcttc tttgcattta aatcacgaaa    540

actgccagag aactttaccg aggctaagtt catcaccttc agcatgctca tctt          594


<210> SEQ ID NO 4
<211> LENGTH: 197
<212> TYPE: PRT
<213> ORGANISM: Salvelinus alpinus
<220> FEATURE:
<221> NAME/KEY: misc_feature
<223> OTHER INFORMATION: Xaa = Any amino acid

<400> SEQUENCE: 4

Leu Ala Leu Cys Ser Val Leu Gly Val Phe Leu Thr Ala Phe Val Met
1               5                   10                  15

Gly Val Phe Ile Arg Phe Arg Asn Thr Pro Ile Val Lys Ala Thr Asn
            20                  25                  30

Arg Glu Leu Ser Tyr Leu Leu Leu Phe Ser Leu Ile Cys Cys Phe Ser
        35                  40                  45

Ser Ser Leu Ile Phe Ile Gly Glu Pro Gln Asp Trp Thr Cys Arg Leu
    50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Trp Gly Leu Asn Leu Gln Phe Leu Leu
            100                 105                 110

Val Phe Leu Phe Thr Phe Val Gln Val Met Ile Cys Val Val Trp Leu
        115                 120                 125

Tyr Asn Ala Pro Pro Ala Ser Tyr Arg Asn His Asp Ile Asp Glu Ile
    130                 135                 140

Ile Phe Ile Thr Cys Asn Glu Gly Ser Met Met Ala Leu Gly Phe Leu
145                 150                 155                 160

Ile Gly Tyr Thr Cys Leu Leu Ala Ala Ile Cys Phe Phe Phe Ala Phe
                165                 170                 175

Lys Ser Arg Lys Leu Pro Glu Asn Phe Thr Glu Ala Lys Phe Ile Thr
            180                 185                 190

Phe Ser Met Leu Ile
        195


<210> SEQ ID NO 5
<211> LENGTH: 593
<212> TYPE: DNA
<213> ORGANISM: Oncorhynchus mykiss

<400> SEQUENCE: 5

ttggcattat gctctgtgct gggggtattc ttgacagtat tcgtgatggg agtgtttatc     60
```

-continued

```
agatttcgca acaccccaat tgttaaggcc acaaacagag agctatccta cctcctcctg    120

ttctcactta tctgctgttt ctccagctcc ctcatcttca ttggtgaacc ccaggactgg    180

acatgccgtc tacgccagcc tgcattcggg ataagttttg ttctctgcat ctcctgcatc    240

ctggtcaaaa ctaaccgagt acttctagtg ttcgaagcaa agatccccac cagtctccat    300

cgtaagtggt gggggctaaa cttgcagttc ctgttggtgt tcctgttcac atttgtgcaa    360

gtgatgatat gtgtggtctg gctttacaat gctcctccgg cgagctacag gaaccatgac    420

attgatgaga tcattttcat tacatgcaat gagggctcta tgatggcgct tggcttccta    480

attgggtaca catgcctgct ggcagccata tgcttcttct ttgcatttaa atcacgaaaa    540

ctgccagaga attttaccga ggctaagttc atcaccttca gcatgctcat ctt           593
```

```
<210> SEQ ID NO 6
<211> LENGTH: 197
<212> TYPE: PRT
<213> ORGANISM: Oncorhynchus mykiss
<220> FEATURE:
<221> NAME/KEY: misc_feature
<223> OTHER INFORMATION: Xaa = Any amino acid

<400> SEQUENCE: 6

Leu Ala Leu Cys Ser Val Leu Gly Val Phe Leu Thr Val Phe Val Met
1               5                   10                  15

Gly Val Phe Ile Arg Phe Arg Asn Thr Pro Ile Val Lys Ala Thr Asn
            20                  25                  30

Arg Glu Leu Ser Tyr Leu Leu Leu Phe Ser Leu Ile Cys Cys Phe Ser
        35                  40                  45

Ser Ser Leu Ile Phe Ile Gly Glu Pro Gln Asp Trp Thr Cys Arg Leu
    50                  55                  60

Arg Gln Pro Ala Phe Gly Ile Ser Phe Val Leu Cys Ile Ser Cys Ile
65                  70                  75                  80

Leu Val Lys Thr Asn Arg Val Leu Leu Val Phe Glu Ala Lys Ile Pro
                85                  90                  95

Thr Ser Leu His Arg Lys Trp Trp Gly Leu Asn Leu Gln Phe Leu Leu
            100                 105                 110

Val Phe Leu Phe Thr Phe Val Gln Val Met Ile Cys Val Val Trp Leu
        115                 120                 125

Tyr Asn Ala Pro Pro Ala Ser Tyr Arg Asn His Asp Ile Asp Glu Ile
    130                 135                 140

Ile Phe Ile Thr Cys Asn Glu Gly Ser Met Met Ala Leu Gly Phe Leu
145                 150                 155                 160

Ile Gly Tyr Thr Cys Leu Leu Ala Ala Ile Cys Phe Phe Phe Ala Phe
                165                 170                 175

Lys Ser Arg Lys Leu Pro Glu Asn Phe Thr Glu Ala Lys Phe Ile Thr
            180                 185                 190

Phe Ser Met Leu Ile
        195
```

```
<210> SEQ ID NO 7
<211> LENGTH: 4134
<212> TYPE: DNA
<213> ORGANISM: Squalus acanthias

<400> SEQUENCE: 7

aattccgttg ctgtcggttc agtccaagtc tcctccagtg caaaatgaga aatggtggtc     60
```

-continued

```
gccattacag gaacatgcac tacatctgtg ttaatgaaat attgtcagtt atctgaaggt    120
tattaaaatg tttctgcaag gatggcttca cgagaaatca attctgcacg ttttcccatt    180
gtcattgtat gaataactga ccaaagggat gtaacaaaat ggaacaaagc tgaggaccac    240
gttcaccctt tcttggagca tacgatcaac cctgaaggag atggaagact tgaggaggaa    300
atggggattg atcttccagg agttctgctg taaagcgatc cctcaccatt acaaagataa    360
gcagaaatcc tccaggcatc ctctgtaaac gggctggcgt agtgtggctt ggtcaaggaa    420
cagagacagg gctgcacaat ggctcagctt cactgccaac tcttattctt gggatttaca    480
ctcctacagt cgtacaatgt ctcagggtat ggtccaaacc aaagggccca gaagaaagga    540
gacatcatac tgggaggtct cttcccaata cactttggag tagccgccaa ggatcaggac    600
ttaaaatcga gaccggaggc gacaaaatgt attcggtaca attttcgagg cttccgatgg    660
ctccaggcga tgatattcgc aattgaagag attaacaaca gtatgacttt cctgcccaat    720
atcaccctgg gatatcgcat atttgacacg tgtaacaccg tgtccaaggc gctagaggca    780
acactcagct ttgtggccca gaacaaaatc gactcgctga acttagatga gttctgtaac    840
tgctctgacc atatcccatc cacaatagca gtggtcgggg caaccgggtc aggaatctcc    900
acggctgtgg ccaatctatt gggattattt tacattccac aggtcagcta tgcctcctcg    960
agcaggctgc tcagcaacaa gaatgagtac aaggccttcc tgaggaccat ccccaatgat   1020
gagcaacagg ccacggccat ggccgagatc atcgagcact tccagtggaa ctgggtggga   1080
accctggcag ccgacgatga ctatggccgc ccaggcattg acaagttccg ggaggaggcc   1140
gttaagaggg acatctgtat tgacttcagt gagatgatct ctcagtacta cacccagaag   1200
cagttggagt tcatcgccga cgtcatccag aactcctcgg ccaaggtcat cgtggtcttc   1260
tccaatggcc ccgacctgga gccgctcatc caggagatag ttcggagaaa catcaccgat   1320
cggatctggc tggccagcga ggcttgggcc agctcttcgc tcattgccaa gccagagtac   1380
ttccacgtgg tcggcggcac catcggcttc gctctcaggg cggggcgtat cccagggttc   1440
aacaagttcc tgaaggaggt ccaccccagc aggtcctcgg acaatgggtt tgtcaaggag   1500
ttctgggagg agaccttcaa ctgctacttc accgagaaga ccctgacgca gctgaagaat   1560
tccaaggtgc cctcgcacgg accggcggct caaggggacg gctccaaggc ggggaactcc   1620
agacggacag ccctacgcca cccctgcact ggggaggaga acatcaccag cgtggagacc   1680
ccctacctgg attatacaca cctgaggatc tcctacaatg tatacgtggc cgtctactcc   1740
attgctcacg ccctgcaaga catccactct tgcaaacccg gcacgggcat ctttgcaaac   1800
ggatcttgtg cagatattaa aaaagttgag gcctggcagg tcctcaacca tctgctgcat   1860
ctgaagttta ccaacagcat gggtgagcag gttgactttg acgatcaagg tgacctcaag   1920
gggaactaca ccattatcaa ctggcagctc tccgcagagg atgaatcggt gttgttccat   1980
gaggtgggca actacaacgc ctacgctaag cccagtgacc gactcaacat caacgaaaag   2040
aaaatcctct ggagtggctt ctccaaagtg gttcctttct ccaactgcag tcgagactgt   2100
gtgccgggca ccaggaaggg gatcatcgag ggggagccca cctgctgctt tgaatgcatg   2160
gcatgtgcag agggagagtt cagtgatgaa aacgatgcaa gtgcgtgtac aaagtgcccg   2220
aatgatttct ggtcgaatga gaaccacacg tcgtgcatcg ccaaggagat cgagtacctg   2280
tcgtggacgg agcccttcgg gatcgctctg accatcttcg ccgtactggg catcctgatc   2340
acctccttcg tgctgggggt cttcatcaag ttcaggaaca ctcccatcgt gaaggccacc   2400
aaccgggagt tgtcctacct gctgctcttc tccctcatct gctgcttctc cagctcgctc   2460
```

-continued

```
atcttcatcg gcgagcccag ggactggacc tgtcggctcc gccaaccggc ctttggcatc   2520

agcttcgtcc tgtgcatctc ctgcatcctg gtgaagacca accgggtgct gctggtcttc   2580

gaggccaaga tccccaccag cctccaccgc aagtgggtgg gcctcaacct gcagttcctc   2640

ctggtcttcc tctgcatcct ggtgcaaatc gtcacctgca tcatctggct ctacaccgcg   2700

cctccctcca gctacaggaa ccatgagctg gaggacgagg tcatcttcat cacctgcgac   2760

gagggctcgc tcatggcgct gggcttcctc atcggctaca cctgcctcct cgccgccatc   2820

tgcttcttct tcgccttcaa gtcccgtaag ctgccggaga acttcaacga ggctaagttc   2880

atcaccttca gcatgttgat cttcttcatc gtctggatct ccttcatccc cgcctatgtc   2940

agcacctacg gcaagtttgt gtcggccgtg gaggtgattg ccatcctggc ctccagcttc   3000

gggctgctgg gctgcattta cttcaacaag tgttacatca tcctgttcaa gccgtgccgt   3060

aacaccatcg aggaggtgcg ctgcagcacg gcggcccacg ccttcaaggt ggcggcccgg   3120

gccaccctcc ggcgcagcgc cgcgtctcgc aagcgctcca gcagcctgtg cggctccacc   3180

atctcctcgc ccgcctcgtc cacctgcggg ccgggcctca ccatggagat gcagcgctgc   3240

agcacgcaga aggtcagctt cggcagcggc accgtcaccc tgtcgctcag cttcgaggag   3300

acaggccgat acgccaccct cagccgcacg gcccgcagca ggaactcggc ggatggccgc   3360

agcggcgacg acctgccatc tagacaccac gaccagggcc cgcctcagaa atgcgagccc   3420

cagcccgcca acgatgcccg atacaaggcg gcgccgacca agggcaccct agagtcgccg   3480

ggcggcagca aggagcgccc cacaactatg gaggaaacct aatccaactc ctccatcaac   3540

cccaagaaca tcctccacgg cagcaccgtc gacaactgac atcaactcct aaccggtggc   3600

tgcccaacct ctcccctctc cggcactttg cgttttgctg aagattgcag catctgcagt   3660

tccttttatc cctgattttc tgacttggat atttactagt gtgcgatgga atatcacaac   3720

ataatgagtt gcacaattag gtgagcagag ttgtgtcaaa gtatctgaac tatctgaagt   3780

atctgaacta ctttattctc tcgaattgta ttacaaacat ttgaagtatt tttagtgaca   3840

ttatgttcta acattgtcaa gataatttgt tacaacatat aaggtaccac ctgaagcagt   3900

gactgagatt gccactgtga tgacagaact gttttataac atttatcatt gaaacctgga   3960

ttgcaacagg aatataatga ctgtaacaaa aaaattgttg attatcttaa aaatgcaaat   4020

tgtaatcaga tgtgtaaaat tggtaattac ttctgtacat taaatgcata tttcttgata   4080

aaaaaaaaaa aaaaaaaaaa aaaaaaaaaa aaaaaagcgg cccgacagca acgg         4134


<210> SEQ ID NO 8
<211> LENGTH: 1027
<212> TYPE: PRT
<213> ORGANISM: Squalus acanthias

<400> SEQUENCE: 8

Met Ala Gln Leu His Cys Gln Leu Leu Phe Leu Gly Phe Thr Leu Leu
1               5                   10                  15

Gln Ser Tyr Asn Val Ser Gly Tyr Gly Pro Asn Gln Arg Ala Gln Lys
            20                  25                  30

Lys Gly Asp Ile Ile Leu Gly Gly Leu Phe Pro Ile His Phe Gly Val
        35                  40                  45

Ala Ala Lys Asp Gln Asp Leu Lys Ser Arg Pro Glu Ala Thr Lys Cys
    50                  55                  60

Ile Arg Tyr Asn Phe Arg Gly Phe Arg Trp Leu Gln Ala Met Ile Phe
65                  70                  75                  80
```

-continued

```
Ala Ile Glu Glu Ile Asn Asn Ser Met Thr Phe Leu Pro Asn Ile Thr
                85                  90                  95

Leu Gly Tyr Arg Ile Phe Asp Thr Cys Asn Thr Val Ser Lys Ala Leu
            100                 105                 110

Glu Ala Thr Leu Ser Phe Val Ala Gln Asn Lys Ile Asp Ser Leu Asn
        115                 120                 125

Leu Asp Glu Phe Cys Asn Cys Ser Asp His Ile Pro Ser Thr Ile Ala
    130                 135                 140

Val Val Gly Ala Thr Gly Ser Gly Ile Ser Thr Ala Val Ala Asn Leu
145                 150                 155                 160

Leu Gly Leu Phe Tyr Ile Pro Gln Val Ser Tyr Ala Ser Ser Ser Arg
                165                 170                 175

Leu Leu Ser Asn Lys Asn Glu Tyr Lys Ala Phe Leu Arg Thr Ile Pro
            180                 185                 190

Asn Asp Glu Gln Gln Ala Thr Ala Met Ala Glu Ile Ile Glu His Phe
        195                 200                 205

Gln Trp Asn Trp Val Gly Thr Leu Ala Ala Asp Asp Asp Tyr Gly Arg
    210                 215                 220

Pro Gly Ile Asp Lys Phe Arg Glu Glu Ala Val Lys Arg Asp Ile Cys
225                 230                 235                 240

Ile Asp Phe Ser Glu Met Ile Ser Gln Tyr Tyr Thr Gln Lys Gln Leu
                245                 250                 255

Glu Phe Ile Ala Asp Val Ile Gln Asn Ser Ser Ala Lys Val Ile Val
            260                 265                 270

Val Phe Ser Asn Gly Pro Asp Leu Glu Pro Leu Ile Gln Glu Ile Val
        275                 280                 285

Arg Arg Asn Ile Thr Asp Arg Ile Trp Leu Ala Ser Glu Ala Trp Ala
    290                 295                 300

Ser Ser Ser Leu Ile Ala Lys Pro Glu Tyr Phe His Val Val Gly Gly
305                 310                 315                 320

Thr Ile Gly Phe Ala Leu Arg Ala Gly Arg Ile Pro Gly Phe Asn Lys
                325                 330                 335

Phe Leu Lys Glu Val His Pro Ser Arg Ser Ser Asp Asn Gly Phe Val
            340                 345                 350

Lys Glu Phe Trp Glu Glu Thr Phe Asn Cys Tyr Phe Thr Glu Lys Thr
        355                 360                 365

Leu Thr Gln Leu Lys Asn Ser Lys Val Pro Ser His Gly Pro Ala Ala
    370                 375                 380

Gln Gly Asp Gly Ser Lys Ala Gly Asn Ser Arg Arg Thr Ala Leu Arg
385                 390                 395                 400

His Pro Cys Thr Gly Glu Glu Asn Ile Thr Ser Val Glu Thr Pro Tyr
                405                 410                 415

Leu Asp Tyr Thr His Leu Arg Ile Ser Tyr Asn Val Tyr Val Ala Val
            420                 425                 430

Tyr Ser Ile Ala His Ala Leu Gln Asp Ile His Ser Cys Lys Pro Gly
        435                 440                 445

Thr Gly Ile Phe Ala Asn Gly Ser Cys Ala Asp Ile Lys Lys Val Glu
    450                 455                 460

Ala Trp Gln Val Leu Asn His Leu Leu His Leu Lys Phe Thr Asn Ser
465                 470                 475                 480

Met Gly Glu Gln Val Asp Phe Asp Asp Gln Gly Asp Leu Lys Gly Asn
                485                 490                 495
```

-continued

```
Tyr Thr Ile Ile Asn Trp Gln Leu Ser Ala Glu Asp Glu Ser Val Leu
            500                 505                 510

Phe His Glu Val Gly Asn Tyr Asn Ala Tyr Ala Lys Pro Ser Asp Arg
        515                 520                 525

Leu Asn Ile Asn Glu Lys Lys Ile Leu Trp Ser Gly Phe Ser Lys Val
    530                 535                 540

Val Pro Phe Ser Asn Cys Ser Arg Asp Cys Val Pro Gly Thr Arg Lys
545                 550                 555                 560

Gly Ile Ile Glu Gly Glu Pro Thr Cys Cys Phe Glu Cys Met Ala Cys
                565                 570                 575

Ala Glu Gly Glu Phe Ser Asp Glu Asn Asp Ala Ser Ala Cys Thr Lys
            580                 585                 590

Cys Pro Asn Asp Phe Trp Ser Asn Glu Asn His Thr Ser Cys Ile Ala
        595                 600                 605

Lys Glu Ile Glu Tyr Leu Ser Trp Thr Glu Pro Phe Gly Ile Ala Leu
    610                 615                 620

Thr Ile Phe Ala Val Leu Gly Ile Leu Ile Thr Ser Phe Val Leu Gly
625                 630                 635                 640

Val Phe Ile Lys Phe Arg Asn Thr Pro Ile Val Lys Ala Thr Asn Arg
                645                 650                 655

Glu Leu Ser Tyr Leu Leu Leu Phe Ser Leu Ile Cys Cys Phe Ser Ser
            660                 665                 670

Ser Leu Ile Phe Ile Gly Glu Pro Arg Asp Trp Thr Cys Arg Leu Arg
        675                 680                 685

Gln Pro Ala Phe Gly Ile Ser Phe Val Leu Cys Ile Ser Cys Ile Leu
    690                 695                 700

Val Lys Thr Asn Arg Val Leu Leu Val Phe Glu Ala Lys Ile Pro Thr
705                 710                 715                 720

Ser Leu His Arg Lys Trp Val Gly Leu Asn Leu Gln Phe Leu Leu Val
                725                 730                 735

Phe Leu Cys Ile Leu Val Gln Ile Val Thr Cys Ile Ile Trp Leu Tyr
            740                 745                 750

Thr Ala Pro Pro Ser Ser Tyr Arg Asn His Glu Leu Glu Asp Glu Val
        755                 760                 765

Ile Phe Ile Thr Cys Asp Glu Gly Ser Leu Met Ala Leu Gly Phe Leu
    770                 775                 780

Ile Gly Tyr Thr Cys Leu Leu Ala Ala Ile Cys Phe Phe Phe Ala Phe
785                 790                 795                 800

Lys Ser Arg Lys Leu Pro Glu Asn Phe Asn Glu Ala Lys Phe Ile Thr
                805                 810                 815

Phe Ser Met Leu Ile Phe Phe Ile Val Trp Ile Ser Phe Ile Pro Ala
            820                 825                 830

Tyr Val Ser Thr Tyr Gly Lys Phe Val Ser Ala Val Glu Val Ile Ala
        835                 840                 845

Ile Leu Ala Ser Ser Phe Gly Leu Leu Gly Cys Ile Tyr Phe Asn Lys
    850                 855                 860

Cys Tyr Ile Ile Leu Phe Lys Pro Cys Arg Asn Thr Ile Glu Glu Val
865                 870                 875                 880

Arg Cys Ser Thr Ala Ala His Ala Phe Lys Val Ala Ala Arg Ala Thr
                885                 890                 895

Leu Arg Arg Ser Ala Ala Ser Arg Lys Arg Ser Ser Ser Leu Cys Gly
            900                 905                 910

Ser Thr Ile Ser Ser Pro Ala Ser Ser Thr Cys Gly Pro Gly Leu Thr
```

```
        915                 920                 925

Met Glu Met Gln Arg Cys Ser Thr Gln Lys Val Ser Phe Gly Ser Gly
    930                 935                 940

Thr Val Thr Leu Ser Leu Ser Phe Glu Glu Thr Gly Arg Tyr Ala Thr
945                 950                 955                 960

Leu Ser Arg Thr Ala Arg Ser Arg Asn Ser Ala Asp Gly Arg Ser Gly
                965                 970                 975

Asp Asp Leu Pro Ser Arg His His Asp Gln Gly Pro Pro Gln Lys Cys
            980                 985                 990

Glu Pro Gln Pro Ala Asn Asp Ala  Arg Tyr Lys Ala Ala  Pro Thr Lys
        995                 1000                1005

Gly Thr  Leu Glu Ser Pro Gly  Gly Ser Lys Glu Arg  Pro Thr Thr
    1010                1015                1020

Met Glu  Glu Thr
    1025


<210> SEQ ID NO 9
<211> LENGTH: 23
<212> TYPE: PRT
<213> ORGANISM: Artificial Sequence
<220> FEATURE:
<223> OTHER INFORMATION: Peptide for antibody production

<400> SEQUENCE: 9

Ala Asp Asp Asp Tyr Gly Arg Pro Gly Ile Glu Lys Phe Arg Glu Glu
1               5                   10                  15

Ala Glu Glu Arg Asp Ile Cys
            20


<210> SEQ ID NO 10
<211> LENGTH: 22
<212> TYPE: PRT
<213> ORGANISM: Artificial Sequence
<220> FEATURE:
<223> OTHER INFORMATION: Peptide for antibody production

<400> SEQUENCE: 10

Asp Asp Tyr Gly Arg Pro Gly Ile Glu Lys Phe Arg Glu Glu Ala Glu
1               5                   10                  15

Glu Arg Asp Ile Cys Ile
            20


<210> SEQ ID NO 11
<211> LENGTH: 17
<212> TYPE: PRT
<213> ORGANISM: Artificial Sequence
<220> FEATURE:
<223> OTHER INFORMATION: Peptide for antibody production

<400> SEQUENCE: 11

Ala Arg Ser Arg Asn Ser Ala Asp Gly Arg Ser Gly Asp Asp Leu Pro
1               5                   10                  15

Cys


<210> SEQ ID NO 12
<211> LENGTH: 28
<212> TYPE: DNA
<213> ORGANISM: Artificial Sequence
<220> FEATURE:
<223> OTHER INFORMATION: Primer for PCR
<220> FEATURE:
<221> NAME/KEY: misc_feature
```

-continued

```
<223> OTHER INFORMATION: K=T or G
      Y=C or T
      R=A or G

<400> SEQUENCE: 12

tgtcktggac ggagccctty ggratcgc                                  28


<210> SEQ ID NO 13
<211> LENGTH: 31
<212> TYPE: DNA
<213> ORGANISM: Artificial Sequence
<220> FEATURE:
<223> OTHER INFORMATION: Primer for PCR
<220> FEATURE:
<221> NAME/KEY: misc_feature
<223> OTHER INFORMATION: K=T or G
      R=A or G

<400> SEQUENCE: 13

ggckggratg aargakatcc aracratgaa g                              31
```